(12) United States Patent
Hyde et al.

(10) Patent No.: US 8,816,814 B2
(45) Date of Patent: Aug. 26, 2014

(54) SYSTEMATIC DISTILLATION OF STATUS DATA RESPONSIVE TO WHETHER OR NOT A WIRELESS SIGNAL HAS BEEN RECEIVED AND RELATING TO REGIMEN COMPLIANCE

(75) Inventors: Roderick A. Hyde, Redmond, WA (US); Edward K. Y. Jung, Bellevue, WA (US); Jordin T. Kare, Seattle, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 296 days.

(21) Appl. No.: 13/199,051

(22) Filed: Aug. 16, 2011

(65) Prior Publication Data

US 2013/0043975 A1 Feb. 21, 2013

Related U.S. Application Data

(63) Continuation-in-part of application No. 13/199,053, filed on Aug. 16, 2011, now Pat. No. 8,514,067, and a continuation-in-part of application No. 13/199,052, filed on Aug. 16, 2011, now Pat. No. 8,723,640, and a continuation-in-part of application No. 13/199,045, filed on Aug. 16, 2011, now Pat. No. 8,599,009, and a continuation-in-part of application No. 13/199,049, filed on Aug. 16, 2011, and a continuation-in-part of application No. 13/199,042, filed on Aug. 16, 2011.

(51) Int. Cl.
*G08B 29/00* (2006.01)

(52) U.S. Cl.
USPC .................................. 340/5.64; 340/539.12

(58) Field of Classification Search
USPC .............. 340/5.61, 5.64, 539.1–539.13, 540, 340/573.1; 424/9.2; 434/262; 600/200, 300, 600/301–302; 601/2; 607/60; 700/231; 702/19; 705/2, 3
See application file for complete search history.

(56) References Cited

U.S. PATENT DOCUMENTS 4,601,896 A 7/1986 Nugent
4,785,969 A 11/1988 McLaughlin
(Continued)

FOREIGN PATENT DOCUMENTS

EP 1 685 871 A1 8/2006
EP 1 698 267 A1 9/2006
(Continued)

OTHER PUBLICATIONS

Corfield, Anthony P. et al.; "Mucins in the Gastrointestinal Tract in Health and Disease"; Frontiers in Bioscience; vol. 6; pp. 1321-1357; Oct. 1, 2001.

(Continued)

*Primary Examiner* — Benjamin C Lee
*Assistant Examiner* — Stephen Burgdorf

(57) ABSTRACT

Configuration technologies for cost-effectively monitoring indicia of regimen compliance or noncompliance in response to one or more indications of symptoms or actions or other data on data-bearing media or in wireless transmissions, such as implementing techniques for providing or preventing access or otherwise acting on or communicating incremental or definitive indicia of compliance or noncompliance.

43 Claims, 24 Drawing Sheets

(56) References Cited

U.S. PATENT DOCUMENTS

| | | |
|---|---|---|
| 5,119,829 A | 6/1992 | Saito et al. |
| 5,148,701 A | 9/1992 | Brown |
| 5,198,192 A | 3/1993 | Saito et al. |
| 5,217,449 A | 6/1993 | Yuda et al. |
| 5,318,024 A | 6/1994 | Kittrell et al. |
| 5,338,625 A | 8/1994 | Bates et al. |
| 5,401,059 A | 3/1995 | Ferrario |
| 5,562,231 A | 10/1996 | Lambelet, Jr. et al. |
| 5,601,811 A | 2/1997 | Gallagher et al. |
| 5,694,919 A | 12/1997 | Rubsamen et al. |
| 5,721,383 A | 2/1998 | Franklin et al. |
| 5,755,741 A | 5/1998 | Vogel |
| 5,790,409 A | 8/1998 | Fedor et al. |
| 5,842,976 A | 12/1998 | Williamson |
| 5,853,005 A | 12/1998 | Scanlon |
| 5,853,292 A | 12/1998 | Eggert et al. |
| 5,891,178 A | 4/1999 | Mann et al. |
| 5,899,877 A | 5/1999 | Leibitzki et al. |
| 5,945,651 A | 8/1999 | Chorosinski et al. |
| 5,978,976 A | 11/1999 | Chai |
| 6,007,986 A | 12/1999 | Sadée |
| 6,016,576 A | 1/2000 | Happe |
| 6,028,520 A | 2/2000 | Maehre |
| 6,029,286 A | 2/2000 | Funk |
| 6,032,155 A | 2/2000 | de la Huerga |
| 6,049,281 A | 4/2000 | Osterweil |
| 6,068,118 A | 5/2000 | Calloway |
| 6,071,254 A | 6/2000 | Augustine |
| 6,076,197 A | 6/2000 | Yeung |
| 6,081,936 A | 7/2000 | Bargman et al. |
| 6,085,752 A | 7/2000 | Kehr et al. |
| 6,096,291 A | 8/2000 | Betbeder et al. |
| 6,102,246 A | 8/2000 | Goulet et al. |
| 6,126,600 A | 10/2000 | Oxaal et al. |
| 6,136,801 A | 10/2000 | Kell |
| 6,138,679 A | 10/2000 | Renders et al. |
| 6,144,852 A | 11/2000 | Orosz |
| 6,151,586 A | 11/2000 | Brown |
| 6,168,563 B1 | 1/2001 | Brown |
| 6,175,811 B1 | 1/2001 | Tekinay |
| 6,198,383 B1 | 3/2001 | Sekura et al. |
| 6,198,695 B1 | 3/2001 | Kirton et al. |
| 6,210,427 B1 | 4/2001 | Augustine et al. |
| 6,219,587 B1 | 4/2001 | Ahlin et al. |
| 6,230,336 B1 | 5/2001 | Knoll et al. |
| 6,250,307 B1 | 6/2001 | Conrad et al. |
| 6,265,963 B1 | 7/2001 | Wood, Jr. |
| 6,273,859 B1 | 8/2001 | Remmers et al. |
| 6,279,173 B1 | 8/2001 | Denzin et al. |
| 6,282,549 B1 | 8/2001 | Hoffert et al. |
| 6,286,508 B1 | 9/2001 | Remmers et al. |
| 6,319,510 B1 | 11/2001 | Yates |
| 6,327,994 B1 | 12/2001 | Labrador |
| 6,329,153 B1 | 12/2001 | Stein et al. |
| 6,336,048 B1 | 1/2002 | Bonnet |
| 6,347,239 B1 | 2/2002 | Arnold et al. |
| 6,365,187 B2 | 4/2002 | Mathiowitz et al. |
| 6,371,931 B1 | 4/2002 | Guillen |
| 6,375,038 B1 | 4/2002 | Daansen et al. |
| 6,411,939 B1 | 6/2002 | Parsons |
| 6,416,471 B1 | 7/2002 | Kumar et al. |
| 6,424,864 B1 | 7/2002 | Matsuura |
| 6,427,839 B1 | 8/2002 | Helfer-Grand |
| 6,428,518 B1 | 8/2002 | Brengle et al. |
| 6,438,399 B1 | 8/2002 | Kurth |
| 6,442,422 B1 | 8/2002 | Duckert |
| 6,454,700 B1 | 9/2002 | Forsell |
| 6,462,684 B1 | 10/2002 | Medelius et al. |
| 6,478,737 B2 | 11/2002 | Bardy |
| 6,494,579 B1 | 12/2002 | Weiss |
| 6,505,059 B1 | 1/2003 | Kollias et al. |
| 6,506,177 B2 | 1/2003 | Landau |
| 6,525,660 B1 | 2/2003 | Surintrspanont |
| 6,527,729 B1 | 3/2003 | Turcott |
| 6,535,131 B1 | 3/2003 | Bar-Shalom et al. |
| 6,539,101 B1 | 3/2003 | Black |
| 6,551,252 B2 | 4/2003 | Sackner et al. |
| 6,553,249 B1 | 4/2003 | Potthoff |
| 6,575,169 B2 | 6/2003 | McMichael |
| 6,577,893 B1 | 6/2003 | Besson et al. |
| 6,581,036 B1 | 6/2003 | Varney, Jr. |
| 6,581,606 B2 | 6/2003 | Kutzko et al. |
| 6,581,607 B2 | 6/2003 | Kutzko et al. |
| 6,581,797 B2 | 6/2003 | McKinney, Jr. et al. |
| 6,587,829 B1 | 7/2003 | Camarda et al. |
| 6,588,670 B2 | 7/2003 | Bukowski |
| 6,601,585 B1 | 8/2003 | Conrad et al. |
| 6,613,573 B1 | 9/2003 | Cohen |
| 6,618,864 B2 | 9/2003 | Veal |
| 6,623,972 B2 | 9/2003 | Malin et al. |
| 6,626,181 B2 | 9/2003 | Knudson et al. |
| 6,626,358 B1 | 9/2003 | Breimesser et al. |
| 6,632,216 B2 | 10/2003 | Houzego et al. |
| 6,645,142 B2 | 11/2003 | Braig et al. |
| 6,655,583 B2 | 12/2003 | Walsh et al. |
| 6,656,159 B2 | 12/2003 | Flaherty |
| 6,658,297 B2 | 12/2003 | Loeb |
| 6,659,959 B2 | 12/2003 | Brockway et al. |
| 6,663,846 B1 | 12/2003 | McCombs et al. |
| 6,671,548 B1 | 12/2003 | Mouchawar et al. |
| 6,678,561 B2 | 1/2004 | Forsell |
| 6,684,418 B2 | 2/2004 | Choi |
| 6,696,924 B1 | 2/2004 | Socinski |
| 6,718,007 B1 | 4/2004 | James |
| 6,723,086 B2 | 4/2004 | Bassuk et al. |
| 6,726,655 B1 | 4/2004 | Lieberman et al. |
| 6,728,679 B1 | 4/2004 | Strubbe et al. |
| 6,731,307 B1 | 5/2004 | Strubbe et al. |
| 6,733,662 B2 | 5/2004 | Pollock |
| 6,740,500 B1 | 5/2004 | Davis et al. |
| 6,745,417 B2 | 6/2004 | Sumino |
| 6,750,053 B1 | 6/2004 | Widrig Opalsky et al. |
| 6,753,781 B2 | 6/2004 | Radomsky et al. |
| 6,755,783 B2 | 6/2004 | Cosentino et al. |
| 6,757,917 B2 | 7/2004 | Kamysz et al. |
| 6,770,029 B2 | 8/2004 | Iliff |
| 6,782,208 B1 | 8/2004 | Lundholm et al. |
| 6,800,060 B2 | 10/2004 | Marshall |
| 6,806,808 B1 | 10/2004 | Watters et al. |
| 6,817,980 B2 | 11/2004 | Iliff |
| 6,818,181 B2 | 11/2004 | Lee |
| 6,819,248 B2 | 11/2004 | Gotfried |
| 6,819,867 B2 | 11/2004 | Mayer, Jr. et al. |
| 6,821,258 B2 | 11/2004 | Reed et al. |
| 6,821,514 B2 | 11/2004 | Houston |
| 6,824,052 B2 | 11/2004 | Walsh |
| 6,830,046 B2 | 12/2004 | Blakley et al. |
| 6,834,775 B1 | 12/2004 | Collins |
| 6,843,766 B1 | 1/2005 | Nemir et al. |
| 6,860,282 B2 | 3/2005 | Guler |
| 6,866,873 B2 | 3/2005 | Stern |
| 6,877,170 B1 | 4/2005 | Quintana et al. |
| 6,881,192 B1 | 4/2005 | Park |
| 6,882,278 B2 | 4/2005 | Winings et al. |
| 6,884,223 B2 | 4/2005 | Kleibohmer et al. |
| 6,893,396 B2 | 5/2005 | Schulze et al. |
| 6,893,879 B2 | 5/2005 | Petersen et al. |
| 6,907,291 B1 | 6/2005 | Snell et al. |
| 6,908,591 B2 | 6/2005 | MacPhee et al. |
| 6,910,050 B2 | 6/2005 | Pawlick |
| 6,910,628 B1 | 6/2005 | Sehr |
| 6,926,667 B2 | 8/2005 | Khouri |
| 6,926,668 B2 | 8/2005 | Bardy |
| 6,934,976 B2 | 8/2005 | Parsons et al. |
| 6,934,977 B1 | 8/2005 | Quintana et al. |
| 6,936,029 B2 | 8/2005 | Mann et al. |
| 6,940,410 B2 | 9/2005 | Deacy |
| 6,941,168 B2 | 9/2005 | Girouard |
| 6,942,619 B2 | 9/2005 | Toda |
| 6,948,194 B2 | 9/2005 | Todoroki et al. |
| 6,951,536 B2 | 10/2005 | Yokoi et al. |
| 6,954,737 B2 | 10/2005 | Kalantar et al. |
| 6,968,294 B2 | 11/2005 | Gutta et al. |
| 6,968,375 B1 | 11/2005 | Brown |

(56) References Cited

U.S. PATENT DOCUMENTS

| | | | |
|---|---|---|---|
| 6,971,383 B2 | 12/2005 | Hickey et al. | |
| 6,971,993 B2 | 12/2005 | Fletcher | |
| 6,972,677 B2 | 12/2005 | Coulthard | |
| 6,973,346 B2 | 12/2005 | Hafer et al. | |
| 6,973,371 B1 | 12/2005 | Benouali | |
| 6,978,177 B1 | 12/2005 | Chen et al. | |
| 6,980,958 B1 | 12/2005 | Surwit et al. | |
| 6,985,779 B2 | 1/2006 | Hsiung et al. | |
| 6,988,026 B2 | 1/2006 | Breed et al. | |
| 6,988,498 B2 | 1/2006 | Berthon-Jones et al. | |
| 6,989,891 B2 | 1/2006 | Braig et al. | |
| 6,995,675 B2 | 2/2006 | Curkendall et al. | |
| 6,997,920 B2 | 2/2006 | Mann et al. | |
| 6,998,230 B1 | 2/2006 | Schantz et al. | |
| 7,003,346 B2 | 2/2006 | Singer | |
| 7,004,907 B2 | 2/2006 | Banet et al. | |
| 7,011,814 B2 | 3/2006 | Suddarth et al. | |
| 7,012,504 B2 | 3/2006 | Tuttle | |
| 7,022,109 B1 | 4/2006 | Ditto | |
| 7,027,935 B2 | 4/2006 | Shimase et al. | |
| 7,032,256 B2 | 4/2006 | Contadini | |
| 7,032,816 B2 | 4/2006 | Markham et al. | |
| 7,035,684 B2 | 4/2006 | Lee | |
| 7,039,453 B2 | 5/2006 | Mullick et al. | |
| 7,041,941 B2 | 5/2006 | Faries, Jr. et al. | |
| 7,047,083 B2 | 5/2006 | Gunderson et al. | |
| 7,049,960 B2 | 5/2006 | Waltermann | |
| 7,054,688 B1 | 5/2006 | Uhrenius et al. | |
| 7,061,523 B2 * | 6/2006 | Fujita et al. | 348/77 |
| 7,062,312 B2 | 6/2006 | Gonzales et al. | |
| 7,063,782 B2 | 6/2006 | Wayment et al. | |
| 7,082,369 B1 | 7/2006 | Rubin et al. | |
| 7,086,269 B2 | 8/2006 | Sauder et al. | |
| 7,086,399 B2 | 8/2006 | Makinson et al. | |
| 7,103,542 B2 | 9/2006 | Doyle | |
| 7,107,095 B2 | 9/2006 | Manolas | |
| 7,107,122 B1 | 9/2006 | Whyte | |
| 7,117,653 B2 | 10/2006 | Yakushigawa et al. | |
| 7,118,531 B2 | 10/2006 | Krill | |
| 7,125,382 B2 | 10/2006 | Zhou et al. | |
| 7,132,238 B2 | 11/2006 | Danenberg | |
| 7,138,240 B2 | 11/2006 | Barak et al. | |
| 7,140,050 B2 | 11/2006 | Muderlak | |
| 7,141,016 B2 | 11/2006 | Lykke et al. | |
| 7,154,275 B2 | 12/2006 | Zank et al. | |
| 7,154,397 B2 | 12/2006 | Zerhusen et al. | |
| 7,166,063 B2 | 1/2007 | Rahman et al. | |
| 7,170,823 B2 | 1/2007 | Fabricius et al. | |
| 7,171,263 B2 | 1/2007 | Darvish et al. | |
| 7,177,684 B1 | 2/2007 | Kroll et al. | |
| 7,177,686 B1 | 2/2007 | Turcott | |
| 7,181,054 B2 | 2/2007 | Zaleski | |
| 7,185,650 B2 | 3/2007 | Huber et al. | |
| 7,187,960 B2 | 3/2007 | Abreu | |
| 7,188,767 B2 | 3/2007 | Panuela et al. | |
| 7,201,732 B2 | 4/2007 | Anderson et al. | |
| 7,203,245 B1 | 4/2007 | Murphy | |
| 7,220,240 B2 | 5/2007 | Struys et al. | |
| 7,223,237 B2 | 5/2007 | Shelchuk | |
| 7,223,246 B2 | 5/2007 | Don | |
| 7,226,442 B2 | 6/2007 | Sheppard, Jr. et al. | |
| 7,232,431 B1 | 6/2007 | Weimann | |
| 7,233,015 B2 | 6/2007 | Roberts | |
| 7,241,578 B2 | 7/2007 | Yugawa et al. | |
| 7,246,619 B2 | 7/2007 | Truschel et al. | |
| 7,248,231 B2 | 7/2007 | Hurley et al. | |
| 7,257,365 B2 | 8/2007 | He et al. | |
| 7,258,666 B2 | 8/2007 | Brown | |
| 7,269,476 B2 | 9/2007 | Ratnakar | |
| 7,271,728 B2 | 9/2007 | Taylor et al. | |
| 7,277,752 B2 | 10/2007 | Matos | |
| 7,280,858 B2 | 10/2007 | Al-Ali et al. | |
| 7,282,926 B1 | 10/2007 | Verspecht et al. | |
| 7,287,031 B1 | 10/2007 | Karpf et al. | |
| 7,293,645 B2 | 11/2007 | Harper et al. | |
| 7,294,105 B1 | 11/2007 | Islam | |
| 7,295,877 B2 | 11/2007 | Govari | |
| 7,295,890 B2 | 11/2007 | Jean-Pierre | |
| 7,297,108 B2 | 11/2007 | Iliff | |
| 7,297,119 B2 | 11/2007 | Westbrook et al. | |
| 7,299,944 B2 | 11/2007 | Roady et al. | |
| 7,305,262 B2 | 12/2007 | Brodnick et al. | |
| 7,308,292 B2 | 12/2007 | Colvin et al. | |
| 7,316,331 B2 | 1/2008 | Gabryszewski | |
| 7,319,639 B2 | 1/2008 | Heyman | |
| 7,327,231 B2 | 2/2008 | Jones et al. | |
| 7,329,238 B2 | 2/2008 | Halseth et al. | |
| 7,329,402 B2 | 2/2008 | Unger et al. | |
| 7,330,101 B2 | 2/2008 | Sekura | |
| 7,330,742 B2 | 2/2008 | Kang et al. | |
| 7,331,340 B2 | 2/2008 | Barney | |
| 7,335,106 B2 | 2/2008 | Johnson | |
| 7,340,296 B2 | 3/2008 | Stahmann et al. | |
| 7,340,381 B2 | 3/2008 | Soma et al. | |
| 7,343,036 B2 | 3/2008 | Kleen et al. | |
| 7,343,943 B2 | 3/2008 | Khan et al. | |
| 7,347,200 B2 | 3/2008 | Jones et al. | |
| 7,350,402 B2 | 4/2008 | Yakhno et al. | |
| 7,351,982 B2 | 4/2008 | Hofstetter et al. | |
| 7,356,364 B1 | 4/2008 | Bullock et al. | |
| 7,357,030 B2 | 4/2008 | Novascone et al. | |
| 7,366,571 B2 | 4/2008 | Armstrong | |
| 7,367,940 B2 | 5/2008 | Fujita et al. | |
| 7,369,476 B2 | 5/2008 | Kravtchenko et al. | |
| 7,369,919 B2 | 5/2008 | Vonk et al. | |
| 7,375,640 B1 | 5/2008 | Plost | |
| 7,378,975 B1 | 5/2008 | Smith et al. | |
| 7,379,885 B1 | 5/2008 | Zakim | |
| 7,382,263 B2 | 6/2008 | Danowski et al. | |
| 7,385,557 B2 | 6/2008 | Kim | |
| 7,394,353 B2 | 7/2008 | Schambeck et al. | |
| 7,395,214 B2 | 7/2008 | Shillingburg | |
| 7,395,216 B2 | 7/2008 | Rosenfeld et al. | |
| 7,396,511 B2 | 7/2008 | Fujii et al. | |
| 7,397,380 B1 | 7/2008 | Smolsky | |
| 7,400,257 B2 | 7/2008 | Rivas | |
| 7,404,796 B2 | 7/2008 | Ginsberg | |
| 7,414,534 B1 | 8/2008 | Kroll et al. | |
| 7,415,737 B2 | 8/2008 | Hung et al. | |
| 7,424,752 B2 | 9/2008 | Antoniou | |
| 7,426,756 B2 | 9/2008 | Clark | |
| 7,427,266 B2 | 9/2008 | Ayer et al. | |
| 7,427,747 B2 | 9/2008 | Ishihara et al. | |
| 7,430,450 B2 | 9/2008 | Imran | |
| 7,437,195 B2 | 10/2008 | Policker et al. | |
| 7,442,180 B2 | 10/2008 | Vitello et al. | |
| 7,451,852 B2 | 11/2008 | Stewart et al. | |
| 7,452,334 B2 | 11/2008 | Gianchandani et al. | |
| 7,455,973 B2 | 11/2008 | Fischer et al. | |
| 7,459,305 B2 | 12/2008 | Levy | |
| 7,460,020 B2 | 12/2008 | Reyes et al. | |
| 7,460,899 B2 | 12/2008 | Almen | |
| 7,460,904 B2 | 12/2008 | Deadwyler et al. | |
| 7,461,418 B2 | 12/2008 | Vlahos et al. | |
| 7,463,700 B2 | 12/2008 | Dabak et al. | |
| 7,465,273 B2 | 12/2008 | Friedman | |
| 7,465,551 B2 | 12/2008 | Blumenthal et al. | |
| 7,467,089 B2 | 12/2008 | Roth et al. | |
| 7,468,040 B2 | 12/2008 | Hartley et al. | |
| 7,468,132 B2 | 12/2008 | Zotter et al. | |
| 7,468,248 B2 | 12/2008 | DeNise et al. | |
| 7,479,877 B2 | 1/2009 | Mortenson et al. | |
| 7,480,032 B2 | 1/2009 | Braig et al. | |
| 7,480,543 B2 | 1/2009 | Bautista et al. | |
| 7,483,693 B2 | 1/2009 | Lueng et al. | |
| 7,484,129 B1 | 1/2009 | Varrichio | |
| 7,485,095 B2 | 2/2009 | Shusterman | |
| 7,485,472 B2 | 2/2009 | Nowak et al. | |
| 7,487,774 B2 | 2/2009 | Acker | |
| 7,488,291 B2 | 2/2009 | Cho et al. | |
| 7,491,493 B2 | 2/2009 | Czub et al. | |
| 7,494,470 B1 | 2/2009 | Turcott | |
| 7,500,951 B2 | 3/2009 | Kawano et al. | |
| 7,504,954 B2 | 3/2009 | Spaeder | |

(56) References Cited

U.S. PATENT DOCUMENTS

| | | |
|---|---|---|
| 7,507,207 B2 | 3/2009 | Sakai et al. |
| 7,510,525 B2 | 3/2009 | Kamo et al. |
| 7,515,556 B2 | 4/2009 | Hui et al. |
| 7,515,734 B2 | 4/2009 | Horovitz et al. |
| 7,517,334 B2 | 4/2009 | Jacobs et al. |
| 7,517,346 B2 | 4/2009 | Sloan et al. |
| 7,518,502 B2 | 4/2009 | Austin et al. |
| 7,525,426 B2 | 4/2009 | Edelstein et al. |
| 7,526,335 B2 | 4/2009 | Ferek-Petric |
| 7,530,948 B2 | 5/2009 | Seibel et al. |
| 7,536,188 B1 | 5/2009 | Fegan et al. |
| 7,536,217 B2 | 5/2009 | Minai et al. |
| 7,538,657 B2 | 5/2009 | Twitchell, Jr. |
| 7,543,766 B2 | 6/2009 | Dobson |
| 7,550,112 B2 | 6/2009 | Gou et al. |
| 7,552,101 B2 | 6/2009 | Bleines |
| 7,554,452 B2 | 6/2009 | Cole |
| 7,560,239 B2 | 7/2009 | Lin et al. |
| 7,564,990 B2 | 7/2009 | Kern et al. |
| 7,574,141 B2 | 8/2009 | Stevenson et al. |
| 7,577,569 B2 | 8/2009 | Roth et al. |
| 7,584,033 B2 | 9/2009 | Mittelsteadt et al. |
| 7,590,449 B2 | 9/2009 | Mann et al. |
| 7,593,768 B1 | 9/2009 | Vasiliev et al. |
| 7,593,952 B2 | 9/2009 | Soll et al. |
| 7,602,754 B2 | 10/2009 | Heinonen et al. |
| 7,611,483 B2 * | 11/2009 | Gerber et al. ............ 604/65 |
| 7,613,426 B2 | 11/2009 | Kuehnel et al. |
| 7,619,819 B2 | 11/2009 | Moon et al. |
| 7,620,817 B2 | 11/2009 | Friedli et al. |
| 7,621,863 B2 | 11/2009 | Forsell |
| 7,625,117 B2 | 12/2009 | Haslett et al. |
| 7,629,888 B2 | 12/2009 | Forster et al. |
| 7,630,736 B2 | 12/2009 | Wang |
| 7,636,470 B2 | 12/2009 | Chen et al. |
| 7,636,667 B2 | 12/2009 | Brown |
| 7,639,120 B2 | 12/2009 | Sekura |
| 7,642,895 B2 | 1/2010 | Fitzgibbon et al. |
| 7,645,581 B2 | 1/2010 | Knapp et al. |
| 7,647,090 B1 | 1/2010 | Frisch et al. |
| 7,650,888 B2 | 1/2010 | Maschke |
| 7,651,471 B2 | 1/2010 | Yokoi et al. |
| 7,658,155 B2 | 2/2010 | Chapman et al. |
| 7,658,727 B1 | 2/2010 | Fernandes et al. |
| 7,666,132 B2 | 2/2010 | Forsell |
| 7,667,609 B1 | 2/2010 | Roe |
| 7,668,710 B2 | 2/2010 | Doyle |
| 7,674,231 B2 | 3/2010 | McCombie et al. |
| 7,676,263 B2 | 3/2010 | Harris et al. |
| 7,679,355 B2 | 3/2010 | Allen et al. |
| 7,680,690 B1 | 3/2010 | Catalano |
| 7,690,378 B1 | 4/2010 | Turcott |
| 7,696,821 B2 | 4/2010 | Rofougaran |
| 7,697,966 B2 | 4/2010 | Monfre et al. |
| 7,699,863 B2 | 4/2010 | Marco et al. |
| 7,706,915 B2 | 4/2010 | Mohapatra et al. |
| 7,707,037 B2 | 4/2010 | Claudatos et al. |
| 7,712,288 B2 | 5/2010 | Ramasubramanian et al. |
| 7,712,674 B1 | 5/2010 | Warner et al. |
| 7,713,200 B1 | 5/2010 | Sarvazyan et al. |
| 7,714,802 B2 | 5/2010 | Hurley et al. |
| 7,715,277 B2 | 5/2010 | de la Huerga |
| 7,718,382 B2 | 5/2010 | Coull et al. |
| 7,720,488 B2 | 5/2010 | Feher |
| 7,722,521 B2 | 5/2010 | Heath |
| 7,725,327 B2 | 5/2010 | McGuigan et al. |
| 7,727,156 B2 | 6/2010 | Angelsen et al. |
| 7,733,224 B2 | 6/2010 | Tran |
| 7,734,928 B2 | 6/2010 | Dunn et al. |
| 7,741,103 B2 | 6/2010 | Guirguis |
| 7,744,640 B1 | 6/2010 | Faries, Jr. et al. |
| 7,745,115 B2 | 6/2010 | Caufield et al. |
| 7,747,454 B2 | 6/2010 | Bartfeld et al. |
| 7,752,056 B2 | 7/2010 | Brown |
| 7,756,723 B2 | 7/2010 | Rosow et al. |
| 7,756,747 B2 | 7/2010 | Agarwal et al. |
| 7,774,213 B2 | 8/2010 | Alexander et al. |
| 7,775,711 B2 | 8/2010 | Wang |
| 7,775,967 B2 | 8/2010 | Gertner |
| 7,777,610 B2 | 8/2010 | O'Toole et al. |
| 7,780,590 B2 | 8/2010 | Birk et al. |
| 7,781,170 B2 | 8/2010 | Tonelli et al. |
| 7,782,190 B1 | 8/2010 | Martin et al. |
| 7,783,442 B2 | 8/2010 | Mueller, Jr. et al. |
| 7,785,291 B2 | 8/2010 | Marco et al. |
| 7,785,772 B2 | 8/2010 | Ahlquist et al. |
| 7,786,845 B2 | 8/2010 | O'Toole et al. |
| 7,786,864 B1 | 8/2010 | Shostak et al. |
| 7,786,865 B2 | 8/2010 | Park |
| 7,789,834 B2 | 9/2010 | Nair et al. |
| 7,792,364 B2 | 9/2010 | Ishiguro |
| 7,793,221 B1 | 9/2010 | Bartholomew |
| 7,796,043 B2 | 9/2010 | Euliano et al. |
| 7,796,162 B2 | 9/2010 | Ortiz |
| 7,797,033 B2 | 9/2010 | D'Andrea et al. |
| 7,798,414 B2 | 9/2010 | Lewis |
| 7,798,907 B2 | 9/2010 | Piccionelli et al. |
| 7,801,745 B2 | 9/2010 | Walker et al. |
| 7,803,108 B2 | 9/2010 | Honda |
| 7,806,852 B1 | 10/2010 | Jurson |
| 7,808,090 B2 | 10/2010 | Shionoiri |
| 7,809,574 B2 | 10/2010 | Roth et al. |
| 7,809,857 B2 | 10/2010 | Anderson et al. |
| 7,818,083 B2 | 10/2010 | Glenn et al. |
| 7,819,311 B2 | 10/2010 | Rowe et al. |
| 7,819,578 B2 | 10/2010 | Coney et al. |
| 7,819,826 B2 | 10/2010 | Diederich et al. |
| 7,820,108 B2 | 10/2010 | Lampotang et al. |
| 7,821,404 B2 | 10/2010 | Walker et al. |
| 7,822,192 B2 | 10/2010 | Gierach et al. |
| 7,822,472 B1 | 10/2010 | Xi |
| 7,822,989 B2 | 10/2010 | Libin et al. |
| 7,825,815 B2 | 11/2010 | Shears et al. |
| 7,830,417 B2 | 11/2010 | Liu et al. |
| 7,830,962 B1 | 11/2010 | Fernandez et al. |
| 7,834,766 B2 | 11/2010 | Sawyer |
| 7,835,319 B2 | 11/2010 | Sugar |
| 7,836,850 B2 | 11/2010 | Pratt |
| 7,837,648 B2 | 11/2010 | Blair et al. |
| 7,837,939 B2 | 11/2010 | Tung et al. |
| 7,839,153 B2 | 11/2010 | Joy et al. |
| 7,839,432 B2 | 11/2010 | Fernandez et al. |
| 7,840,269 B2 | 11/2010 | Policker et al. |
| 7,844,505 B1 | 11/2010 | Arneson et al. |
| 7,844,687 B1 | 11/2010 | Gelvin et al. |
| 7,849,752 B2 | 12/2010 | Gregory et al. |
| 7,852,217 B2 | 12/2010 | Kondo et al. |
| 7,853,455 B2 | 12/2010 | Brown |
| 7,853,468 B2 | 12/2010 | Callahan et al. |
| 7,855,630 B2 | 12/2010 | Darr |
| 7,855,643 B2 | 12/2010 | Tuttle |
| 7,857,767 B2 | 12/2010 | Ferren et al. |
| 7,860,583 B2 | 12/2010 | Condurso et al. |
| 7,861,676 B2 | 1/2011 | Kates |
| 7,863,994 B2 | 1/2011 | Hung et al. |
| 7,869,853 B1 | 1/2011 | Say et al. |
| 7,870,249 B2 | 1/2011 | Brown |
| 7,876,228 B2 | 1/2011 | Kroll et al. |
| 7,877,120 B2 | 1/2011 | Jacobs et al. |
| 7,878,016 B2 | 2/2011 | Rotem et al. |
| 7,881,797 B2 | 2/2011 | Griffin et al. |
| 7,881,934 B2 | 2/2011 | Endo et al. |
| 7,885,713 B2 | 2/2011 | Campbell et al. |
| 7,887,599 B2 | 2/2011 | Casares et al. |
| 7,890,295 B2 | 2/2011 | Shin et al. |
| 7,891,866 B2 | 2/2011 | Rogers et al. |
| 7,894,849 B2 | 2/2011 | Kass et al. |
| 7,894,882 B2 | 2/2011 | Mullick et al. |
| 7,898,570 B2 | 3/2011 | Yokota et al. |
| 7,899,508 B2 | 3/2011 | DeArmond |
| 7,901,383 B2 | 3/2011 | Follman et al. |
| 7,905,230 B2 | 3/2011 | Schuler et al. |
| 7,910,031 B2 | 3/2011 | Yang et al. |
| 7,911,348 B2 | 3/2011 | Rodgers |

(56) References Cited

U.S. PATENT DOCUMENTS

| | | |
|---|---|---|
| 7,914,442 B1 | 3/2011 | Gazdzinski |
| 7,914,468 B2 | 3/2011 | Shalon et al. |
| 7,914,483 B2 | 3/2011 | Simmons |
| 7,914,514 B2 | 3/2011 | Calderon |
| 7,914,564 B2 | 3/2011 | Magers et al. |
| 7,916,013 B2 | 3/2011 | Stevenson |
| 7,917,377 B2 | 3/2011 | Rao et al. |
| 7,917,973 B2 | 4/2011 | Baumoel |
| 7,918,435 B2 | 4/2011 | Page |
| 7,918,779 B2 | 4/2011 | Haber et al. |
| 7,918,786 B2 | 4/2011 | Kawano et al. |
| 7,918,821 B2 | 4/2011 | Mahurkar |
| 7,918,843 B2 | 4/2011 | Genosar et al. |
| 7,920,312 B2 | 4/2011 | Rosman et al. |
| 7,920,732 B2 | 4/2011 | Shimizu et al. |
| 7,920,907 B2 | 4/2011 | McGarraugh et al. |
| 7,920,991 B2 | 4/2011 | Kodialam et al. |
| 7,925,519 B2 | 4/2011 | Greene |
| 7,926,491 B2 | 4/2011 | Wright et al. |
| 7,927,548 B2 | 4/2011 | Slowey et al. |
| 7,931,592 B2 | 4/2011 | Currie et al. |
| 7,933,642 B2 | 4/2011 | Istvan et al. |
| 7,933,720 B2 | 4/2011 | Park et al. |
| 7,934,836 B2 | 5/2011 | Ito |
| 7,936,713 B2 | 5/2011 | Kubler et al. |
| 7,937,319 B2 | 5/2011 | Kennis et al. |
| 7,937,461 B2 | 5/2011 | Kutzik et al. |
| 7,940,049 B2 | 5/2011 | Loubet |
| 7,940,914 B2 | 5/2011 | Petrushin |
| 7,941,095 B2 | 5/2011 | Twitchell, Jr. |
| 7,941,162 B2 | 5/2011 | Ioppe et al. |
| 7,941,323 B2 | 5/2011 | Brown |
| 7,941,534 B2 | 5/2011 | de la Huerga |
| 7,942,827 B2 | 5/2011 | Mir et al. |
| 7,942,916 B2 | 5/2011 | Altshuler et al. |
| 7,943,384 B2 | 5/2011 | Durack et al. |
| 7,944,342 B2 | 5/2011 | Sekura |
| 7,944,886 B2 | 5/2011 | Stephenson et al. |
| 7,945,393 B2 | 5/2011 | Treado et al. |
| 7,945,457 B2 | 5/2011 | Zaleski |
| 7,945,461 B2 | 5/2011 | Sekura |
| 7,948,381 B2 | 5/2011 | Lindsay et al. |
| 7,949,150 B2 | 5/2011 | Haering et al. |
| 7,951,046 B1 | 5/2011 | Barber, Jr. |
| 7,951,080 B2 | 5/2011 | Taub |
| 7,951,989 B2 | 5/2011 | McGrath et al. |
| 7,952,480 B1 | 5/2011 | Kuzma et al. |
| 7,954,994 B2 | 6/2011 | Warth et al. |
| 7,956,727 B2 | 6/2011 | Loncar |
| 7,956,734 B2 | 6/2011 | Oozawa et al. |
| 7,957,781 B2 | 6/2011 | Mannheimer et al. |
| 7,957,984 B1 | 6/2011 | Vallone |
| 7,959,540 B2 | 6/2011 | Jaquish et al. |
| 7,959,568 B2 | 6/2011 | Stahmann et al. |
| 7,961,936 B2 | 6/2011 | Liang et al. |
| 7,963,946 B2 | 6/2011 | Moubayed et al. |
| 7,965,180 B2 | 6/2011 | Koyama |
| 7,965,798 B2 | 6/2011 | Roh et al. |
| 7,966,263 B2 | 6/2011 | Beeson |
| 7,967,439 B2 | 6/2011 | Shelhamer et al. |
| 7,967,759 B2 | 6/2011 | Couvillon, Jr. |
| 7,969,307 B2 | 6/2011 | Peeters |
| 7,969,311 B2 | 6/2011 | Markhovsky et al. |
| 7,970,208 B2 | 6/2011 | Han |
| 7,970,470 B2 | 6/2011 | Hartley et al. |
| 7,972,296 B2 | 7/2011 | Braig et al. |
| 7,973,043 B2 | 7/2011 | Migaly |
| 7,973,664 B1 | 7/2011 | Lambert et al. |
| 7,975,543 B2 | 7/2011 | Clem et al. |
| 7,976,480 B2 | 7/2011 | Grajales et al. |
| 7,978,051 B2 | 7/2011 | Shimura |
| 7,978,062 B2 | 7/2011 | LaLonde et al. |
| 7,978,082 B2 | 7/2011 | Braunstein |
| 7,978,083 B2 | 7/2011 | Melker et al. |
| 7,978,494 B2 | 7/2011 | Kang |
| 7,978,564 B2 | 7/2011 | De La Huerga |
| 7,978,642 B2 | 7/2011 | Cave et al. |
| 7,978,657 B2 | 7/2011 | Choi et al. |
| 7,979,034 B2 | 7/2011 | Khannur et al. |
| 7,979,284 B2 | 7/2011 | Brown |
| 7,981,025 B2 | 7/2011 | Pool et al. |
| 7,981,046 B2 | 7/2011 | Yarden et al. |
| 7,981,058 B2 | 7/2011 | Akay |
| 7,981,102 B2 | 7/2011 | Patel et al. |
| 7,983,305 B2 | 7/2011 | Kim |
| 7,983,458 B2 | 7/2011 | Wang et al. |
| 7,983,682 B2 | 7/2011 | Halkka et al. |
| 7,983,759 B2 | 7/2011 | Stahmann et al. |
| 7,983,763 B2 | 7/2011 | Stevenson et al. |
| 7,983,817 B2 | 7/2011 | Breed |
| 7,983,933 B2 | 7/2011 | Karkanias et al. |
| 7,984,849 B2 | 7/2011 | Berghel et al. |
| 7,984,853 B2 | 7/2011 | Ali |
| 7,986,218 B2 | 7/2011 | Watters et al. |
| 7,986,220 B2 | 7/2011 | Kiyomasa et al. |
| 7,986,239 B2 | 7/2011 | Chang |
| 7,987,280 B1 | 7/2011 | Putnam et al. |
| 7,987,720 B2 | 8/2011 | Gayle |
| 7,988,038 B2 | 8/2011 | Beenau et al. |
| 7,988,055 B2 | 8/2011 | Garber et al. |
| 7,988,627 B2 | 8/2011 | Bagan |
| 7,988,917 B2 | 8/2011 | Roesicke et al. |
| 7,989,313 B2 | 8/2011 | Wang et al. |
| 7,991,213 B2 | 8/2011 | Tafas et al. |
| 7,991,485 B2 | 8/2011 | Zakim |
| 7,991,628 B2 | 8/2011 | Jung et al. |
| 8,165,893 B1* | 4/2012 | Goldberg et al. ............... 705/2 |
| 8,249,811 B2 | 8/2012 | Petrovic |
| 8,360,961 B2* | 1/2013 | Jung et al. .................. 600/109 |
| 8,564,432 B2 | 10/2013 | Covannon et al. |
| 2002/0016535 A1 | 2/2002 | Martin et al. |
| 2002/0143563 A1* | 10/2002 | Hufford et al. ............... 705/1 |
| 2003/0050542 A1 | 3/2003 | Reihl et al. |
| 2003/0135392 A1 | 7/2003 | Vrijens et al. |
| 2004/0175289 A1 | 9/2004 | Takizawa et al. |
| 2005/0043965 A1 | 2/2005 | Heller et al. |
| 2005/0143787 A1 | 6/2005 | Boveja et al. |
| 2005/0203773 A1 | 9/2005 | Soto et al. |
| 2006/0061472 A1 | 3/2006 | Lovoi et al. |
| 2006/0064037 A1* | 3/2006 | Shalon et al. ............... 600/586 |
| 2006/0210626 A1 | 9/2006 | Spaeder |
| 2006/0218011 A1 | 9/2006 | Walker et al. |
| 2006/0285441 A1 | 12/2006 | Walker et al. |
| 2006/0289640 A1 | 12/2006 | Mercure et al. |
| 2007/0008112 A1 | 1/2007 | Covannon et al. |
| 2007/0008113 A1 | 1/2007 | Spoonhower et al. |
| 2007/0061166 A1* | 3/2007 | Ramasubramanian et al. .. 705/2 |
| 2007/0097792 A1 | 5/2007 | Burrows et al. |
| 2007/0123772 A1 | 5/2007 | Euliano et al. |
| 2007/0126582 A1 | 6/2007 | Posamentier |
| 2007/0132597 A1* | 6/2007 | Rodgers .................. 340/573.1 |
| 2007/0156346 A1 | 7/2007 | Hyde et al. |
| 2007/0156347 A1 | 7/2007 | Hyde et al. |
| 2007/0237719 A1 | 10/2007 | Jones et al. |
| 2007/0276270 A1* | 11/2007 | Tran ........................ 600/508 |
| 2008/0004904 A1* | 1/2008 | Tran ........................ 705/2 |
| 2008/0059228 A1 | 3/2008 | Bossi et al. |
| 2008/0097188 A1 | 4/2008 | Pool et al. |
| 2008/0140451 A1* | 6/2008 | Karkanias et al. .......... 705/2 |
| 2008/0146871 A1 | 6/2008 | Arneson et al. |
| 2008/0175898 A1* | 7/2008 | Jones et al. ............... 424/452 |
| 2008/0306402 A1* | 12/2008 | Singer ...................... 600/547 |
| 2009/0192648 A1 | 7/2009 | Namineni et al. |
| 2009/0294521 A1* | 12/2009 | de la Huerga ............. 235/375 |
| 2010/0036036 A1* | 2/2010 | Ferren et al. .............. 600/301 |
| 2010/0052915 A1 | 3/2010 | Allen et al. |
| 2010/0139672 A1 | 6/2010 | Kroll et al. |
| 2010/0228082 A1* | 9/2010 | Zou et al. ................. 600/104 |
| 2010/0305975 A1* | 12/2010 | Daya et al. ............... 705/3 |
| 2011/0124983 A1* | 5/2011 | Kroll et al. ............... 600/302 |
| 2011/0133894 A1 | 6/2011 | Hennig et al. |
| 2011/0163871 A1 | 7/2011 | Einav et al. |

(56) References Cited

U.S. PATENT DOCUMENTS

2011/0225004 A1* 9/2011 Loncar ............................ 705/2
2012/0008714 A1   1/2012 Rizwan

FOREIGN PATENT DOCUMENTS

| WO | WO 2004/104957 A1 | 12/2004 |
| WO | WO 2006123346 A2 | 11/2006 |

OTHER PUBLICATIONS

Wanekaya, Adam K. et al.; "Nanowire-Based Electrochemical Biosensors"; Electroanalysis; vol. 18; No. 6; pp. 533-550; Jan. 17, 2006; Wiley-VCH.

Moore, Bert; "The Potential Use of Radio Frequency Identification Devices for Active Monitoring of Blood Glucose Levels"; Journal of Diabetes Science and Technology; vol. 3; No. 1; pp. 180-183; Jan. 2009; Diabetes Technology Society.

* cited by examiner

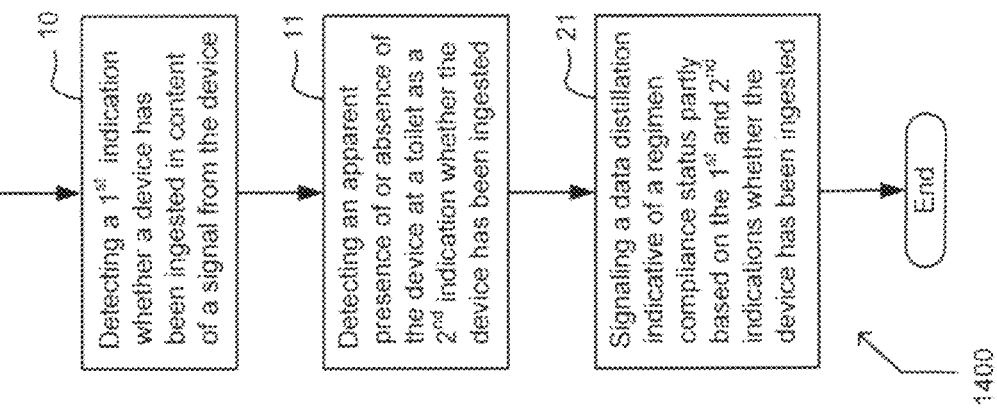
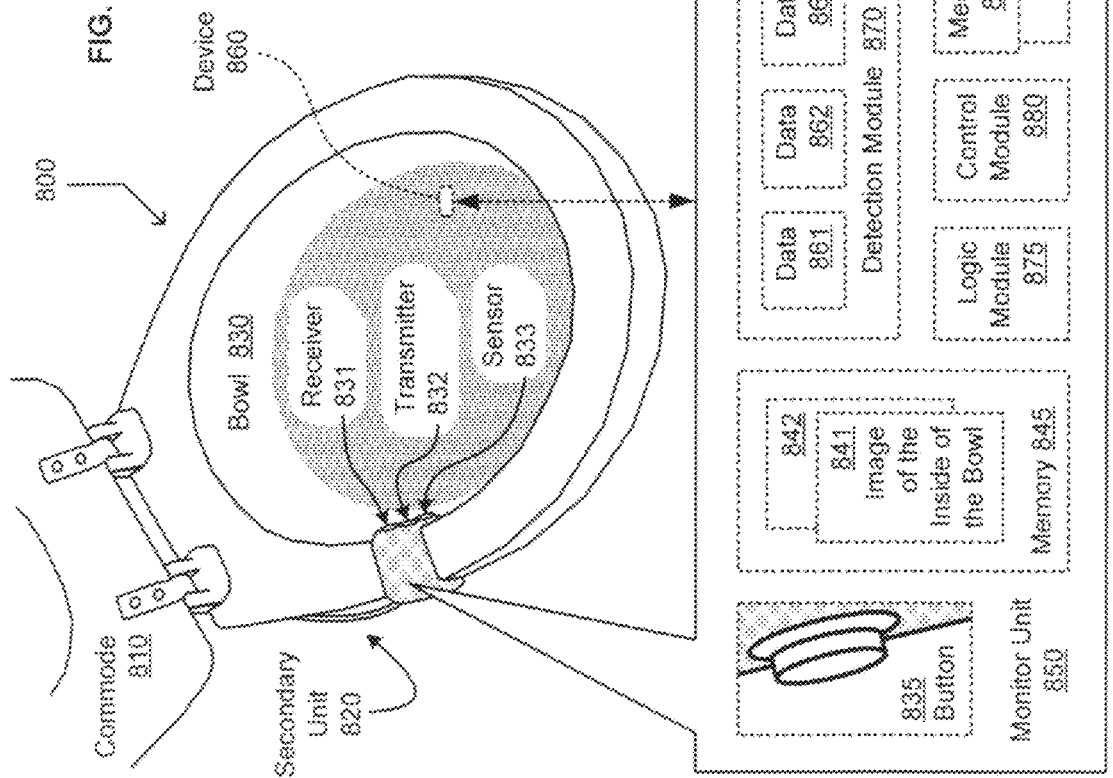

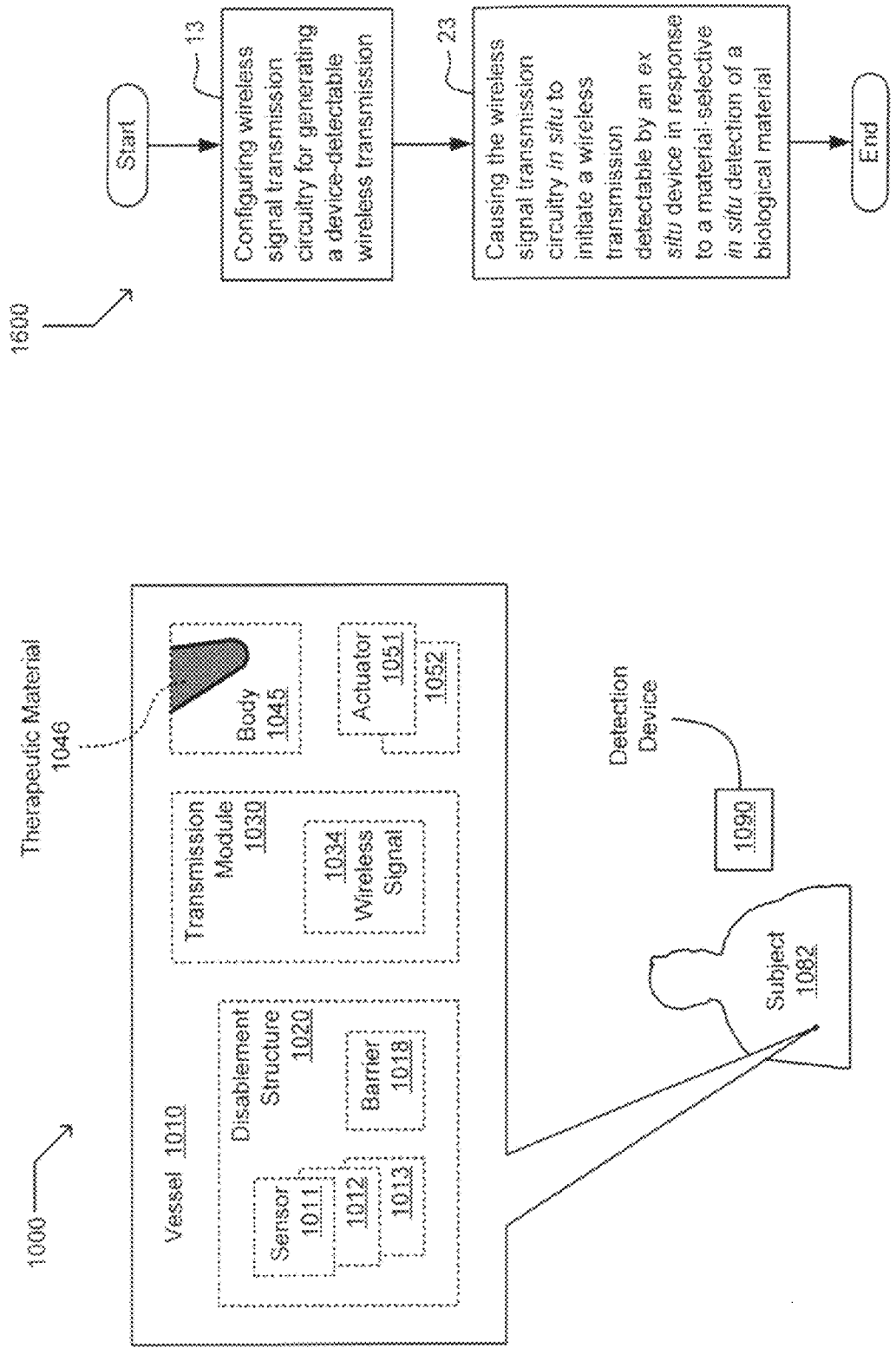

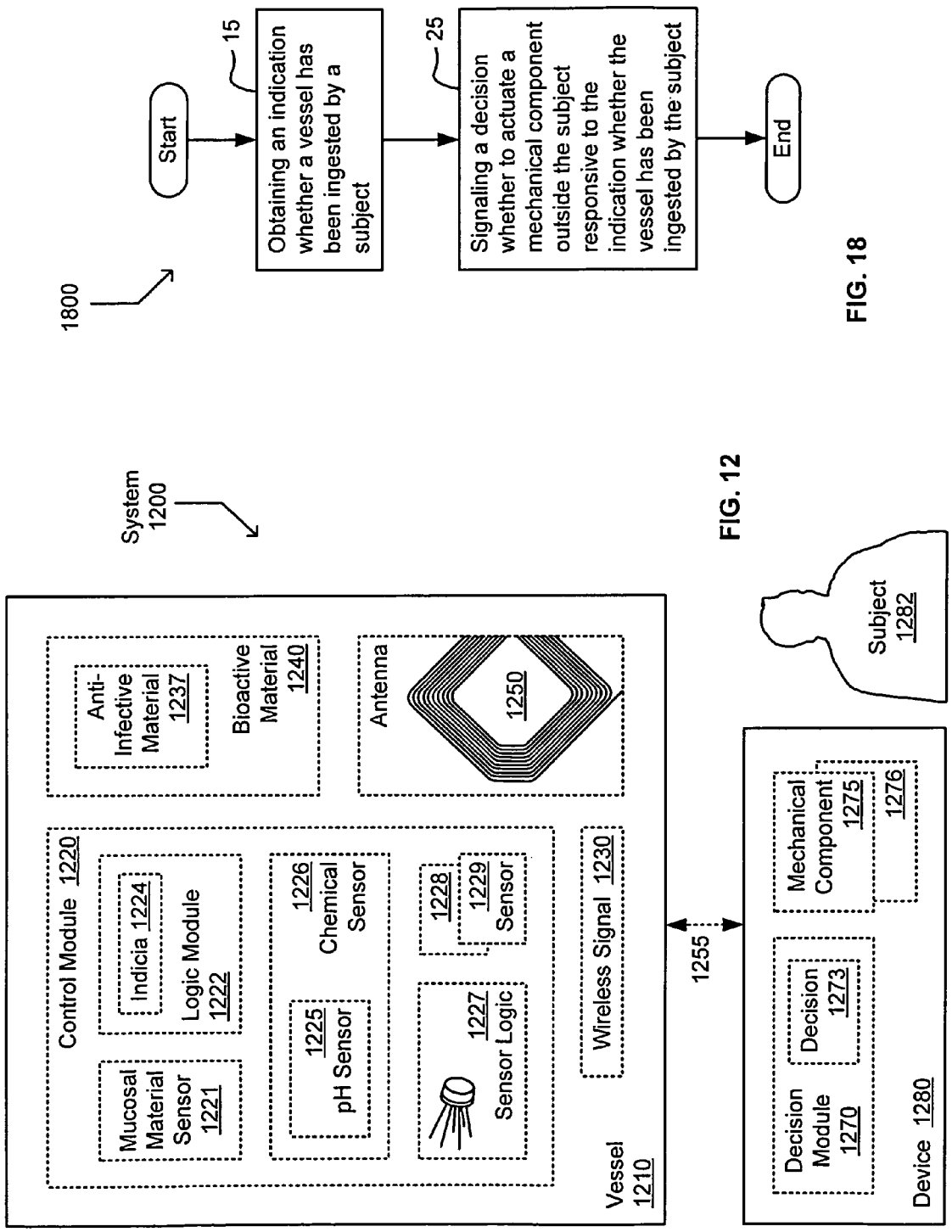

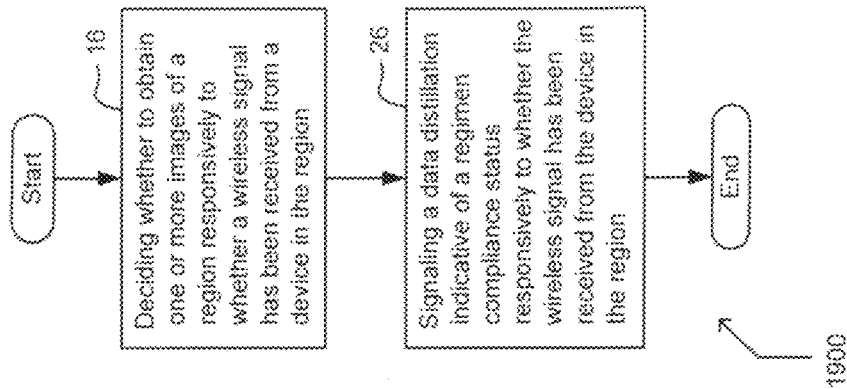
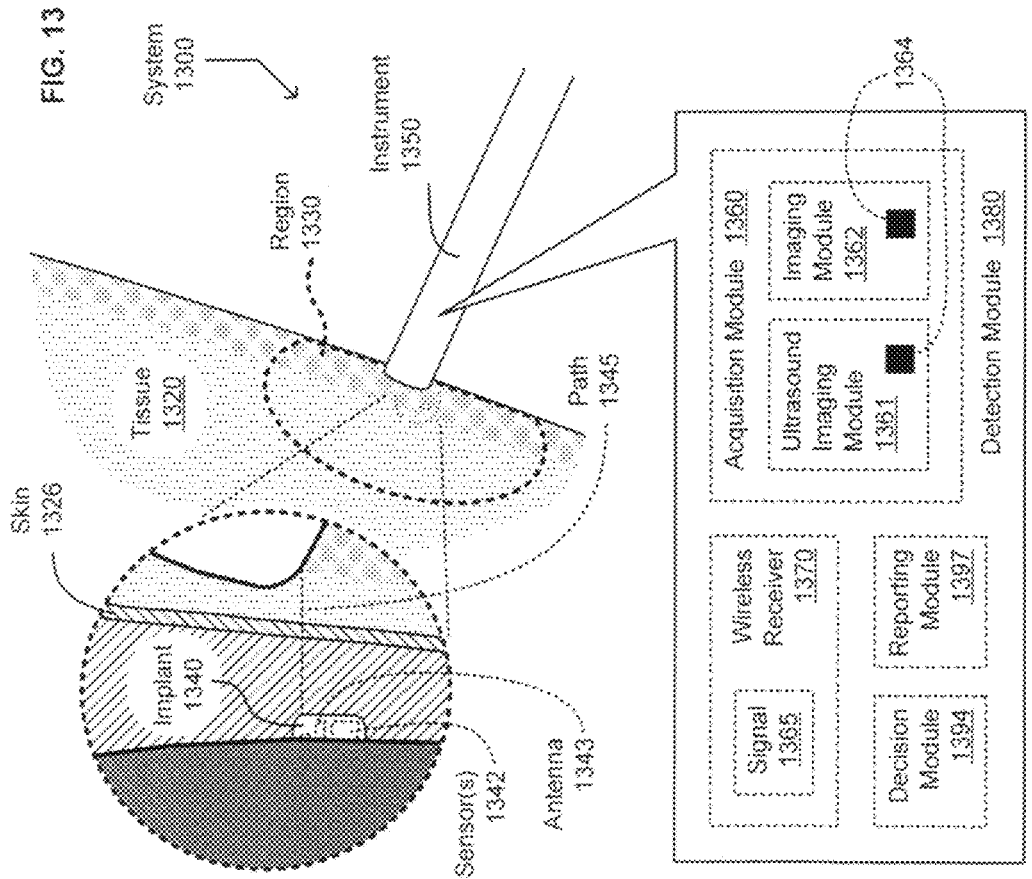

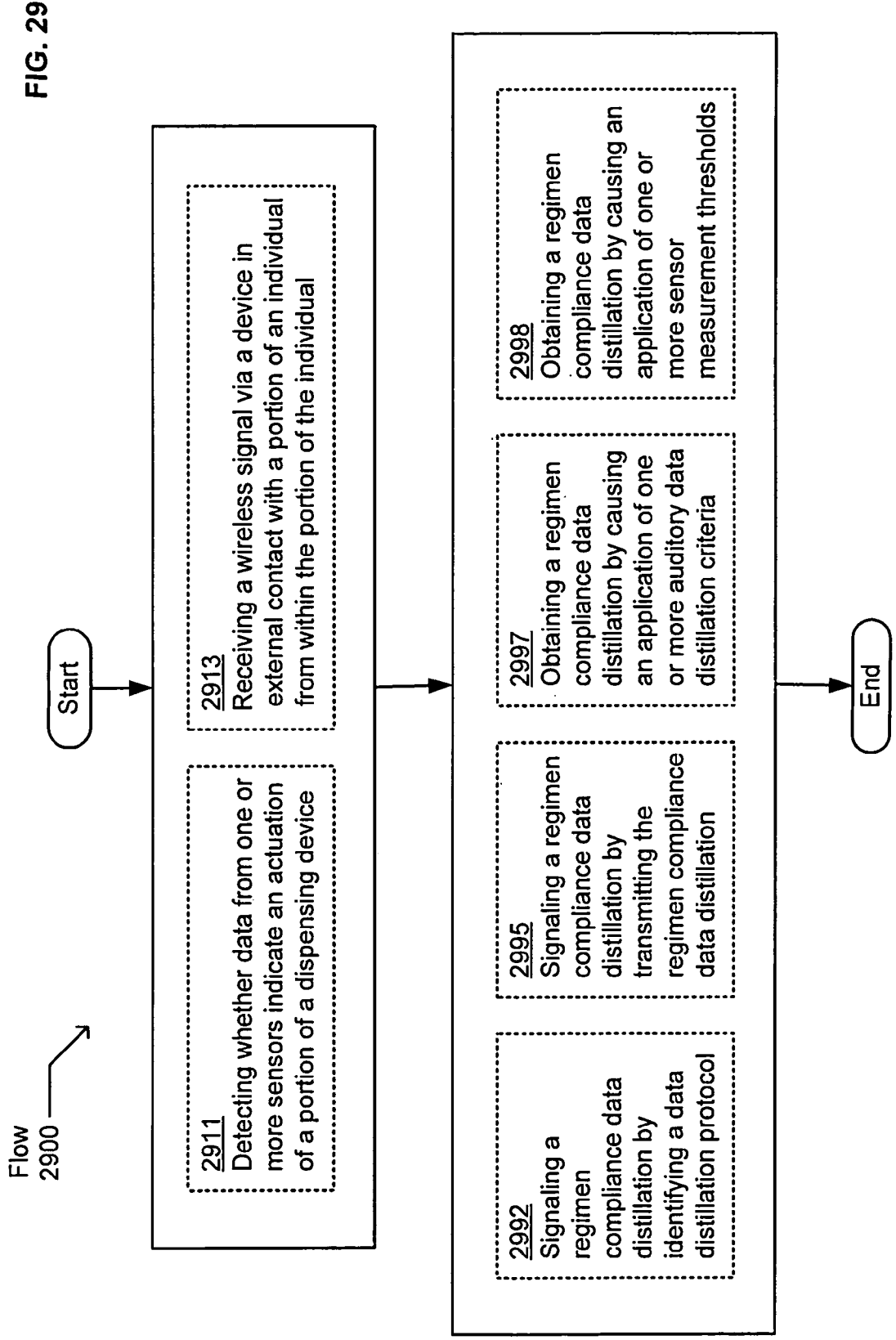

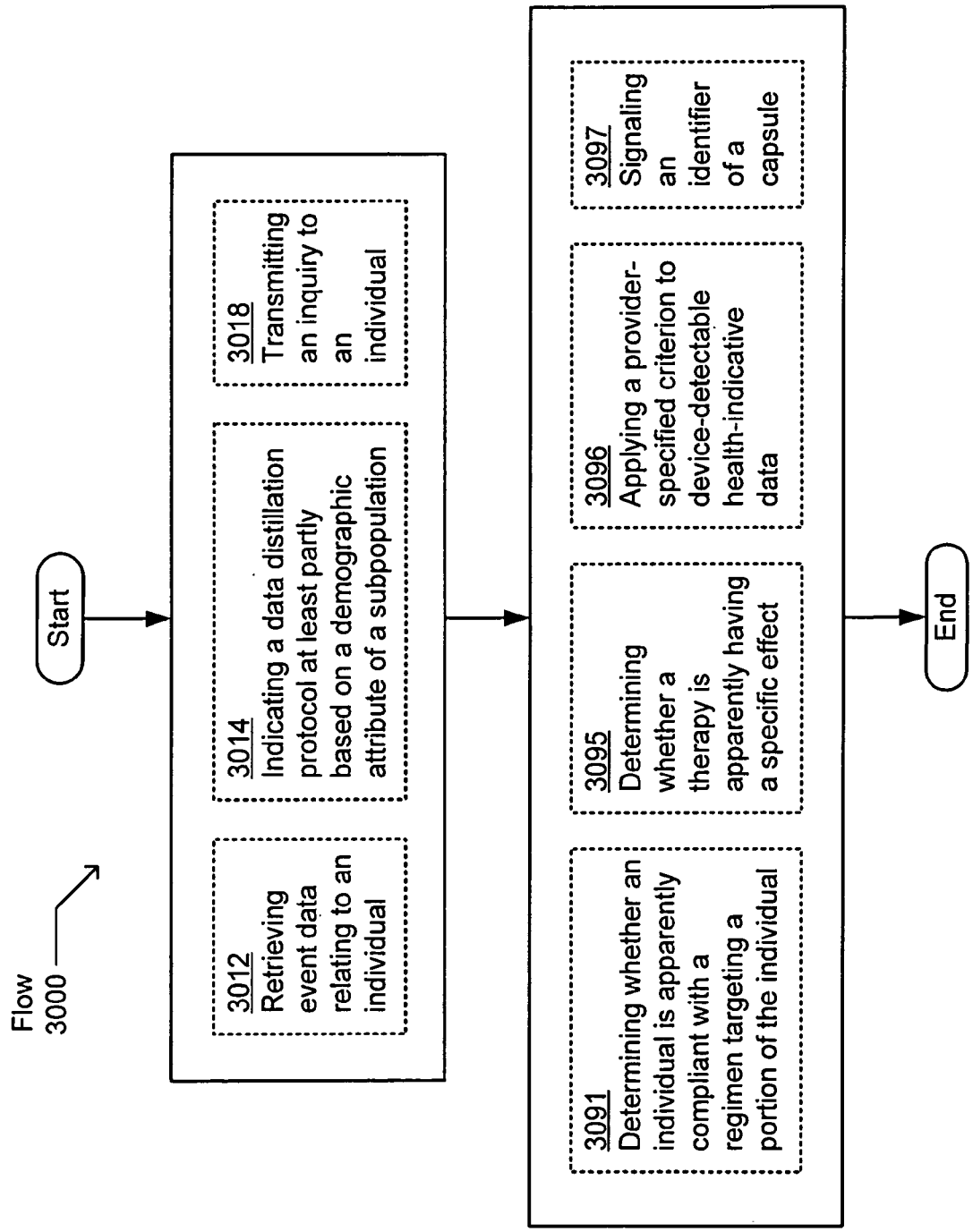

SYSTEMATIC DISTILLATION OF STATUS DATA RESPONSIVE TO WHETHER OR NOT A WIRELESS SIGNAL HAS BEEN RECEIVED AND RELATING TO REGIMEN COMPLIANCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/199,053, now U.S. Pat. No. 8,514,067 U.S. patent application Ser. No. 13/199,052, now U.S. Pat. No. 8,723,640 U.S. patent application Ser. No. 13/199,045, now U.S. Pat. No. 8,599,009 U.S. patent application Ser. No. 13/199,049, and U.S. patent application Ser. No. 13/199,042, each entitled SYSTEMATIC DISTILLATION OF STATUS DATA RELATING TO REGIMEN COMPLIANCE, naming Roderick A. Hyde, Edward K. Y. Jung, Jordin T. Kare, Royce A. Levien, Robert W. Lord, Mark A. Malamud, John D. Rinaldo, Jr., Elizabeth A. Sweeney, and Lowell L. Wood, Jr., as inventors, filed 16 Aug. 2011, each of which is currently co-pending or is an application of which a currently co-pending application is entitled to the benefit of the filing date.

For purposes of the USPTO extra-statutory requirements, the present application claims benefit of priority of U.S. patent application Ser. No. 13/199,053, U.S. patent application Ser. No. 13/199,052, U.S. patent application Ser. No. 13/199,045, U.S. patent application Ser. No. 13/199,049, and U.S. patent application Ser. No. 13/199,042, each entitled SYSTEMATIC DISTILLATION OF STATUS DATA RELATING TO REGIMEN COMPLIANCE, naming Roderick A. Hyde, Edward K. Y. Jung, Jordin T. Kare, Royce A. Levien, Robert W. Lord, Mark A. Malamud, John D. Rinaldo, Jr., Elizabeth A. Sweeney, and Lowell L. Wood, Jr., as inventors, filed 16 Aug. 2011, each of which was filed within the twelve months preceding the filing date of the present application or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

TECHNICAL FIELD

Configuration technologies for cost-effectively monitoring indicia of regimen compliance or noncompliance in response to one or more indications of symptoms or actions or other data on data-bearing media (user cards or similar articles in local interfaces, e.g.) or in wireless transmissions, and which may be classified inter alia in U.S. Class 235, Subclass 379 or 494.

SUMMARY

An embodiment provides a method. In one implementation, the method includes but is not limited to detecting a first indication whether a first device has been ingested in content of a signal from the first device; detecting an apparent presence of or absence of a first device at a toilet as a second indication whether the first device has been ingested; and signaling a data distillation indicative of a regimen compliance status partly based on the first indication whether the first device has been ingested in the content of the signal from the first device and partly based on the apparent presence of or absence of the first device at the toilet as the second indication whether the first device has been ingested. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for detecting a first indication whether a first device has been ingested in content of a signal from the first device; circuitry for detecting an apparent presence of or absence of a first device at a toilet as a second indication whether the first device has been ingested; and circuitry for signaling a data distillation indicative of a regimen compliance status partly based on the first indication whether the first device has been ingested in the content of the signal from the first device and partly based on the apparent presence of or absence of the first device at the toilet as the second indication whether the first device has been ingested. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to detecting a first indication whether a first device has been ingested in content of a signal from the first device; detecting an apparent presence of or absence of a first device at a toilet as a second indication whether the first device has been ingested; and signaling a data distillation indicative of a regimen compliance status partly based on the first indication whether the first device has been ingested in the content of the signal from the first device and partly based on the apparent presence of or absence of the first device at the toilet as the second indication whether the first device has been ingested. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for detecting a first indication whether a first device has been ingested in content of a signal from the first device; detecting an apparent presence of or absence of a first device at a toilet as a second indication whether the first device has been ingested; and signaling a data distillation indicative of a regimen compliance status partly based on the first indication whether the first device has been ingested in the content of the signal from the first device and partly based on the apparent presence of or absence of the first device at the toilet as the second indication whether the first device has been ingested. In addition to the foregoing, other system aspects are described in the claims, drawings, and text forming a part of the present disclosure.

An embodiment provides a method. In one implementation, the method includes but is not limited to determining whether a presence of a wireless signal in a first frequency range below a threshold frequency occurred contemporaneously with an absence of a wireless signal in a second frequency range above the threshold frequency and indicating a regimen compliance status of a subject in response to the circuitry for determining whether a presence of a wireless signal in a first frequency range below a threshold frequency occurred contemporaneously with an absence of a wireless signal in a second frequency range above the threshold frequency. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for determining whether a presence of a wireless signal in a first frequency range below a threshold frequency occurred contemporaneously with an absence of a wireless signal in a second frequency range above the threshold frequency and circuitry for indicating a regimen compliance status of a subject in response to the circuitry for determining whether a presence of a wireless signal in a first frequency range below a threshold frequency occurred contemporaneously with an absence of a wireless signal in a second frequency range above the threshold frequency. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to determining whether a presence of a wireless signal in a first frequency range below a threshold frequency occurred contemporaneously with an absence of a wireless signal in a second frequency range above the threshold frequency and indicating a regimen compliance status of a subject in response to the circuitry for determining whether a presence of a wireless signal in a first frequency range below a threshold frequency occurred contemporaneously with an absence of a wireless signal in a second frequency range above the threshold frequency. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for determining whether a presence of a wireless signal in a first frequency range below a threshold frequency occurred contemporaneously with an absence of a wireless signal in a second frequency range above the threshold frequency and indicating a regimen compliance status of a subject in response to the circuitry for determining whether a presence of a wireless signal in a first frequency range below a threshold frequency occurred contemporaneously with an absence of a wireless signal in a second frequency range above the threshold frequency. In addition to the foregoing, other system aspects are described in the claims, drawings, and text forming a part of the present disclosure.

An embodiment provides a method. In one implementation, the method includes but is not limited to generating a device-detectable wireless transmission and causing the wireless signal transmission circuitry in situ to initiate a wireless transmission detectable by an ex situ device in response to a material-selective in situ detection of a biological material. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for generating a device-detectable wireless transmission and circuitry for causing the wireless signal transmission circuitry in situ to initiate a wireless transmission detectable by an ex situ device in response to a material-selective in situ detection of a biological material. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to generating a device-detectable wireless transmission and causing the wireless signal transmission circuitry in situ to initiate a wireless transmission detectable by an ex situ device in response to a material-selective in situ detection of a biological material. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for generating a device-detectable wireless transmission and causing the wireless signal transmission circuitry in situ to initiate a wireless transmission detectable by an ex situ device in response to a material-selective in situ detection of a biological material. In addition to the foregoing, other system aspects are described in the claims, drawings, and text forming a part of the present disclosure.

An embodiment provides a method. In one implementation, the method includes but is not limited to obtaining first data indicating that at least a portion of a container moved, the first data signaling that a therapeutic material has been administered to a portion of a subject and signaling second data corroborating or contraindicating that the therapeutic material has been administered to the portion of the subject responsive to the first data indicating that at least the portion of the container moved. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for obtaining first data indicating that at least a portion of a container moved, the first data signaling that a therapeutic material has been administered to a portion of a subject and circuitry for signaling second data corroborating or contraindicating that the therapeutic material has been administered to the portion of the subject responsive to the first data indicating that at least the portion of the container moved. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining first data indicating that at least a portion of a container moved, the first data signaling that a therapeutic material has been administered to a portion of a subject and signaling second data corroborating or contraindicating that the therapeutic material has been administered to the portion of the subject responsive to the first data indicating that at least the portion of the container moved. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining first data indicating that at least a portion of a container moved, the first data signaling that a therapeutic material has been administered to a portion of a subject and signaling second data corroborating or contraindicating that the therapeutic material has been administered to the portion of the subject responsive to the first data indicating that at least the portion of the container moved. In addition to the foregoing, other system aspects are described in the claims, drawings, and text forming a part of the present disclosure.

An embodiment provides a method. In one implementation, the method includes but is not limited to obtaining an indication whether a vessel has been ingested by a subject and signaling a decision whether to actuate a mechanical component outside the subject responsive to the indication whether the vessel has been ingested by the subject. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for obtaining an indication whether a vessel has been ingested by a subject and circuitry for signaling a decision whether to actuate a mechanical component outside the subject responsive to the indication whether the vessel has been ingested by the subject. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication whether a vessel has been ingested by a subject and signaling a decision whether to actuate a mechanical component outside the subject responsive to the indication whether the vessel has been ingested by the subject. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication whether a vessel has been ingested by a subject and signaling a decision whether to actuate a mechanical component outside the subject responsive to the indication whether the vessel has been ingested by the subject. In addition to the foregoing, other system aspects are described in the claims, drawings, and text forming a part of the present disclosure.

An embodiment provides a method. In one implementation, the method includes but is not limited to deciding whether to obtain one or more images of a region responsively to whether a wireless signal has been received from a device in the region and signaling a data distillation indicative of a regimen compliance status responsively to whether the wireless signal has been received from the device in the region. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for deciding whether to obtain one or more images of a region responsively to whether a wireless signal has been received from a device in the region and circuitry for signaling a data distillation indicative of a regimen compliance status responsively to whether the wireless signal has been received from the device in the region. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to deciding whether to obtain one or more images of a region responsively to whether a wireless signal has been received from a device in the region and signaling a data distillation indicative of a regimen compliance status responsively to whether the wireless signal has been received from the device in the region. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for deciding whether to obtain one or more images of a region responsively to whether a wireless signal has been received from a device in the region and signaling a data distillation indicative of a regimen compliance status responsively to whether the wireless signal has been received from the device in the region. In addition to the foregoing, other system aspects are described in the claims, drawings, and text forming a part of the present disclosure.

In some variants, implementations described herein may apply in one or more contexts of treating communicable disease (tuberculosis, e.g.) or of neurological, psychiatric, psychological, or physiological regimens (including one or more anti-addiction, anti-psychotic, or other psychoactive therapeutic components, e.g.). Such regimens may likewise include various therapy (pharmaceutical, nutraceutical, physical, or sleep therapy, e.g.) or access management or selective notifications or other responsive protocols described herein. Such implementations may also occur in one or more contexts of brain/mind system pathologies, therapies, and related monitoring or management thereof. In some contexts, such monitoring may include messages or other signals distilled into signals for invoking one or more mechanisms or notifying third parties (insurance providers or employers or consultants, e.g.) or by invoking other suitable responses as described herein (via a separate network, e.g.).

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth below.

BRIEF DESCRIPTION OF THE FIGURES

FIG. 8 depicts an exemplary environment featuring a commode.

FIG. 10 depicts an exemplary environment featuring a vessel in or on a subject.

FIG. 12 depicts an exemplary environment featuring a vessel operable for wireless communication.

FIG. 13 depicts an exemplary environment featuring a device that can be detected by another device.

FIG. 14 depicts a high-level logic flow of an operational process described with reference to FIG. 8.

FIG. 16 depicts a high-level logic flow of an operational process described with reference to FIG. 10.

FIG. 18 depicts a high-level logic flow of an operational process described with reference to FIG. 12.

FIG. 19 depicts a high-level logic flow of an operational process described with reference to FIG. 13.

FIG. 27-30 each depicts additional variants of earlier-presented flows.

DETAILED DESCRIPTION

Figure 1:
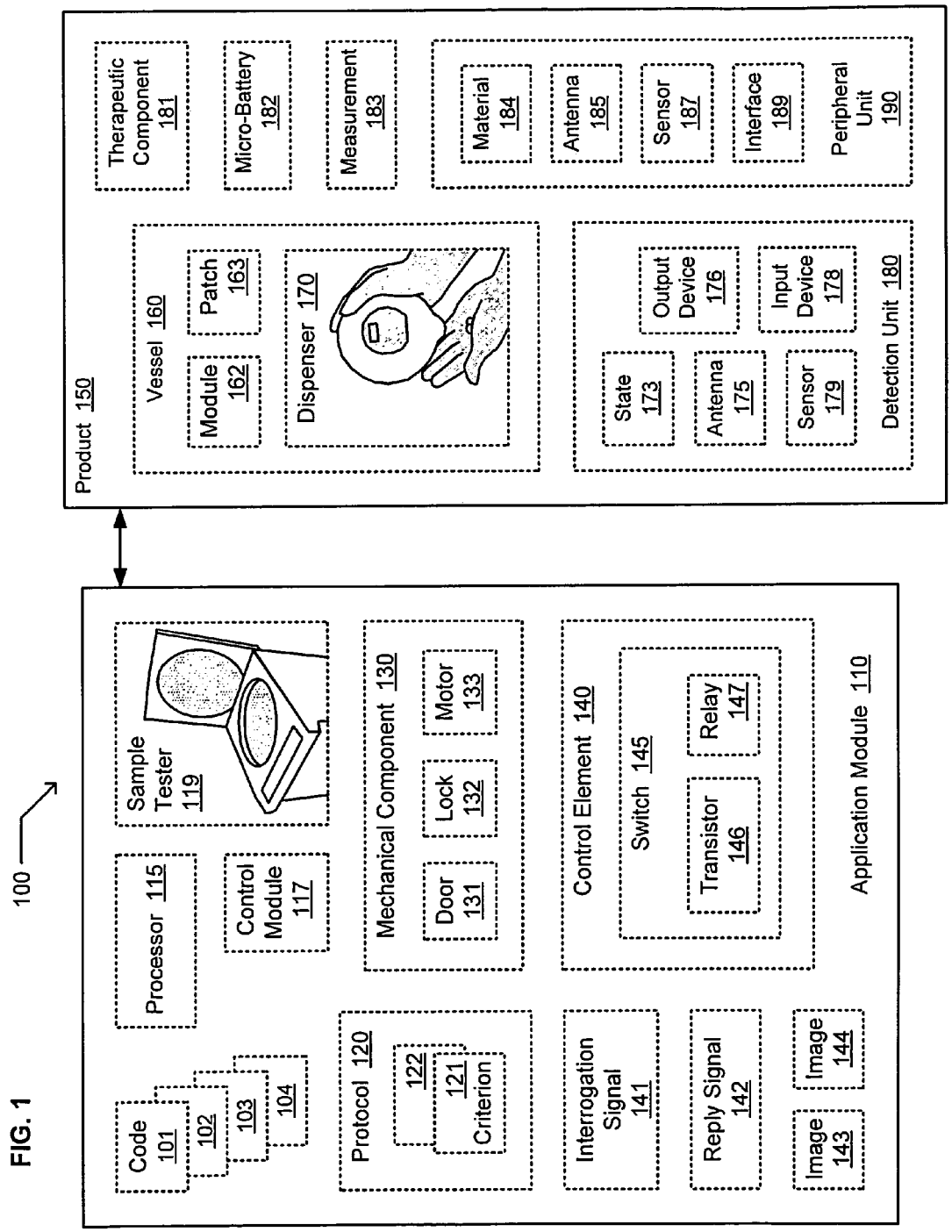
FIG. 1 depicts an exemplary environment in which one or more technologies may be implemented in one or more application modules or other products.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Referring now to FIG. 1, there is shown a system 100 in which one or more technologies may be implemented. An application module 110 is operable to receive information from (and in some variants to interact with) one or more instances of a product 150 (a patch 163, station, pillbox, dispenser 170, capsule, or other such vessel 160 containing one or more operational modules 162 (software or circuitry, e.g.) as described below. Application module 110 may include one or more instances of device-executable code 101, 102, 103, 104 executable by one or more processors 115 or control modules 117. In some variants, application module 110 may include a sample tester 119 or may implement a security protocol 120 that applies one or more criteria 121, 122 in deciding whether to open, close, engage, disengage, or otherwise actuate one or more doors 131, locks 132, motors 133, or other mechanical components 130. In some contexts, for example, such operations may involve controlling one or more switches 145 (transistors 146 or relays 147 operably coupled with such mechanical components 130, e.g.) or other control elements 140. Alternatively or additionally, code 101-104 may include one or more instructions for transmitting one or more queries or other interrogation signals 141 or awaiting or otherwise responding to one or more reply signals 142 or other incoming messages, images 143, 144, or other data as described below.

Alternatively or additionally, product 150 may include one or more detection units 180 comprising one or more sensors 179 or antennas 175, 185 or other output devices 176 or input devices 178 that can communicate or transition between respective states 173 as described below. In some variants a patch 163, capsule or other health-related product 150 may further include one or more bioactive materials 184 or other therapeutic components 181. Product 150 may likewise include one or more powered components (sensors 187 or interfaces 189 in a peripheral unit 190, e.g.) powered by a micro-battery 182 and operable for taking or communicating one or more measurements 183 as described below.

Figure 2:
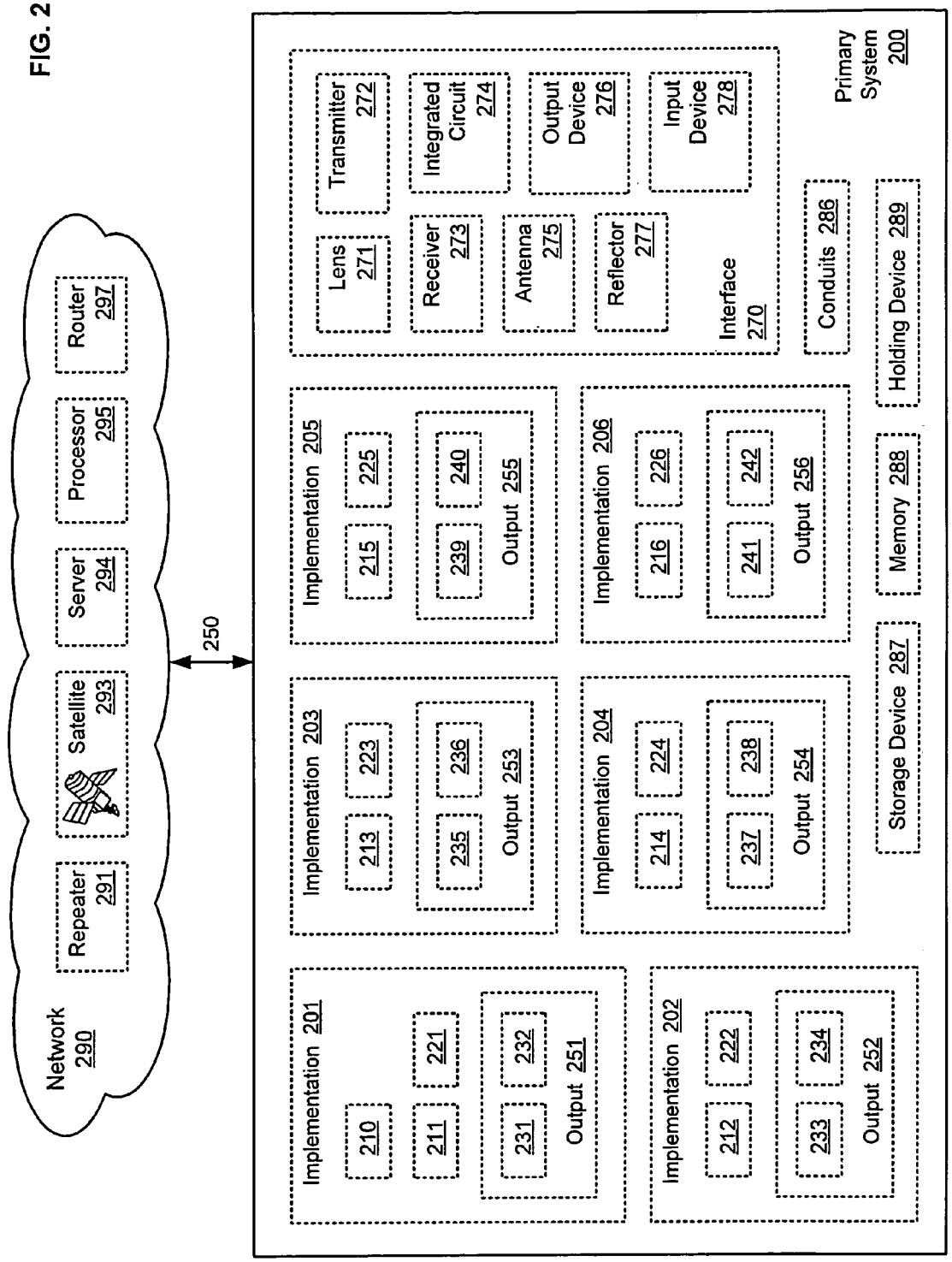
FIG. 2 depicts a context for introducing one or more processes, systems, or other articles described herein.

With reference now to FIG. 2, shown is an example of a system that may serve as a context for introducing one or more processes, systems or other articles described herein. Primary system 200 may include one or more instances of data outputs 251, 252, 253, 254, 255, 256 or other implementations 201, 202, 203, 204, 205, 206 of machines, articles of manufacture, or compositions of matter that include circuitry or other logic as described herein. In some contexts, implementations 201-206 may be held or transmitted by interfaces 270, conduits 286, storage devices 287, memories 288, other holding devices 289, or other circuitry for handling data or software as described herein. In various embodiments, one or more instances of implementation components 210, 211, 212, 213, 214, 215, 216, 221, 222, 223, 224, 225, 226 or implementation output data 231, 232, 233, 234, 235, 236, 237, 238, 239, 240, 241, 242 may each be expressed within any aspect or combination of software, firmware, or hardware as signals, data, designs, logic, instructions, or the like. The interface(s) 270 may include one or more instances of lenses 271, transmitters 272, receivers 273, integrated circuits 274, antennas 275, output devices 276, reflectors 277, or input devices 278 for handling data or communicating with local users or with network 290 via linkage 250, for example. Several variants of primary system 200 are described below with reference to one or more instances of repeaters 291, communication satellites 293, servers 294, processors 295, routers 297, or other elements of network 290.

Those skilled in the art will recognize that some list items may also function as other list items. In the above-listed types of media, for example, some instances of interface(s) 270 may include conduits 286, or may also function as storage devices that are also holding devices 289. One or more transmitters 272 may likewise include input devices or bidirectional user interfaces, in many implementations of interface(s) 270. Each such listed term should not be narrowed by any implication from other terms in the same list but should instead be understood in its broadest reasonable interpretation as understood by those skilled in the art.

Figure 3:
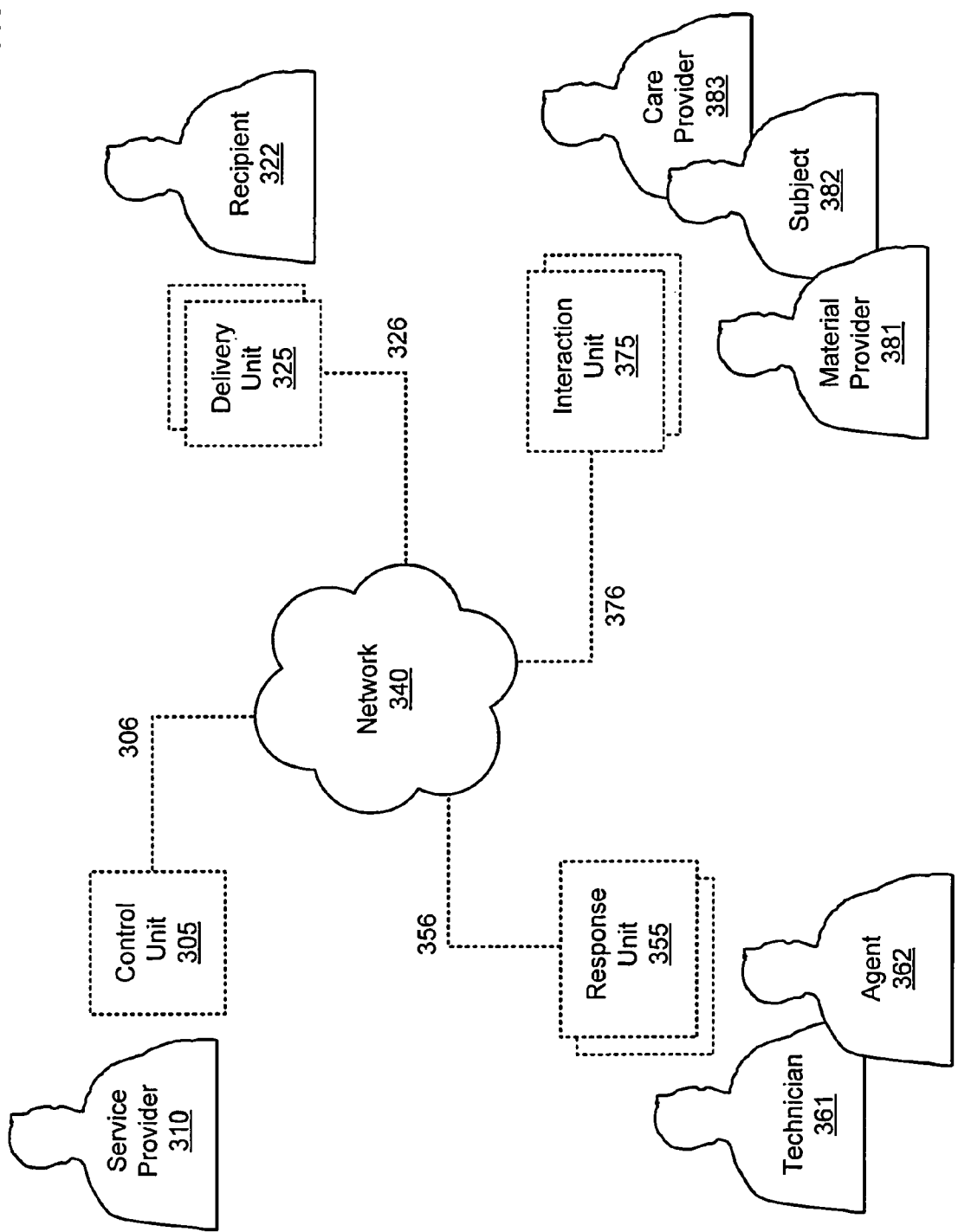
FIG. 3 depicts a network having wireless signal paths or other suitable linkages providing access among several parties.

With reference now to FIG. 3, shown is an example of a network 340 and several linkages 306, 326, 356, 376 through which mutually remote service providers 310, technicians 361, and recipients 322 can interact. In some variants one or more control units 305, delivery units 325, response units 355, or interaction units 375 may each comprise a tablet computer, handheld device, wearable communication device, portable digital device, or workstation. In some contexts one or more technicians 361 or other agents 362 may each have a response unit 355 as described below. In general one or more subjects 382 may be remote from a service provider 310, technician 361, or agent 362 but available locally to one or more pharmacists or other material providers 381 or to one or more nurses, parents, or other care providers 383 (via one or more application modules 110, products 150, or other interaction units 375 as shown, e.g.).

Figure 4:
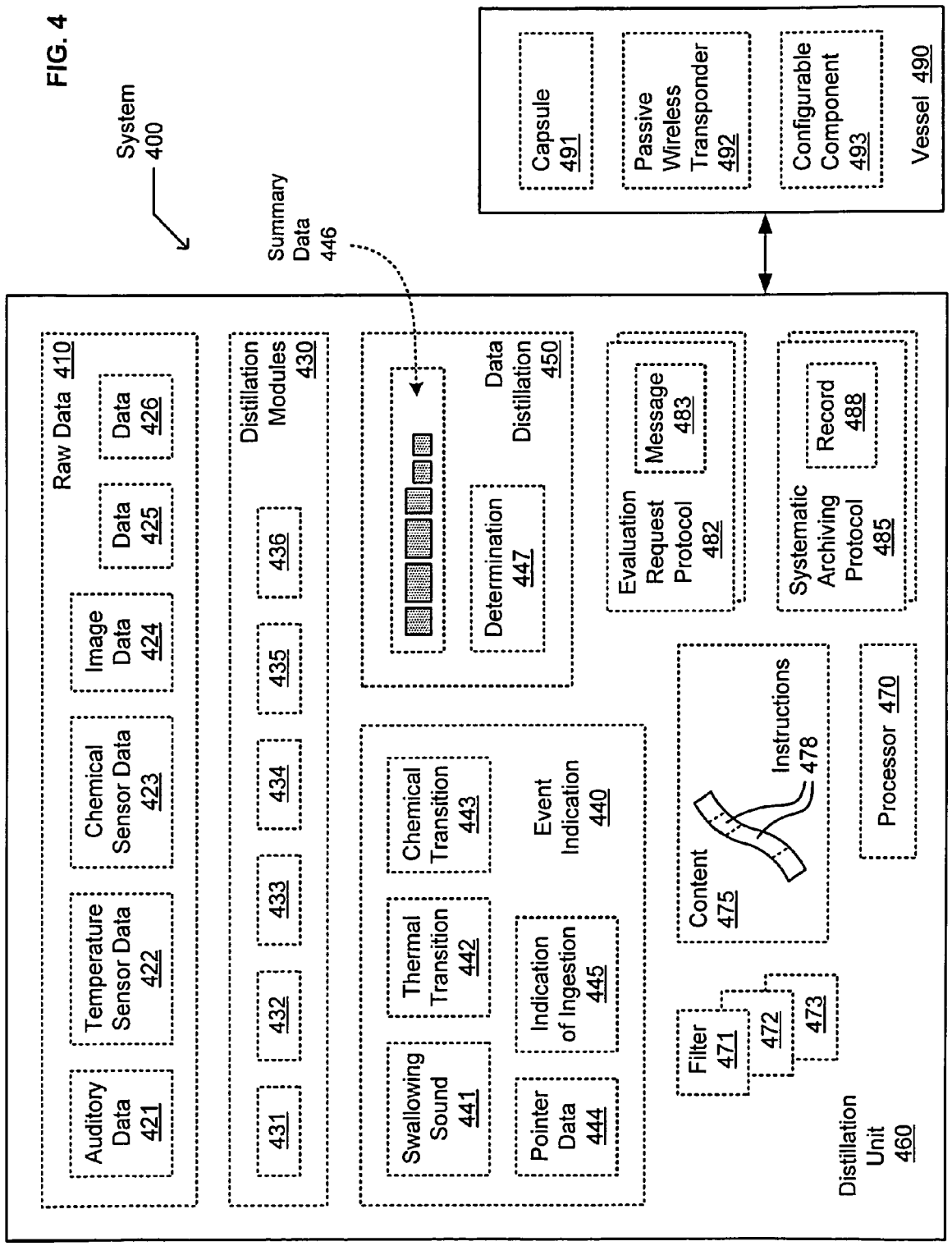
FIG. 4 depicts an exemplary environment in which one or more technologies may be implemented in one or more vessels or data distillation units.

With reference now to FIG. 4, shown is an example of a system 400 having one or more distillation units 460 configured to monitor or interact with one or more vessels 490. Instances of distillation unit 460 may be implemented in application module 110, product 150, primary system 200, or one or more networks 290, 340 as described herein. Distillation unit 460 may include various distillation modules 430 configured to handle various raw data 410 (auditory data 421, temperature sensor data 422, chemical sensor data 423, image data 424, or other data 425, 426 as described below, e.g.). One or more auditory data distillation modules 431, for example, may be configured to recognize or otherwise distill specific event indications 440 (spoken words or swallowing sounds 441, e.g.) from raw auditory data 421. One or more other data distillation modules 432, 433 may likewise be configured to recognize or otherwise distill one or more other specific event indications 440 (thermal transitions 442 or chemical transitions 443, e.g.) from raw measurement data (temperature sensor data 422 or chemical sensor data 423, e.g.). One or more image processing data distillation modules 434 may likewise be configured to recognize or otherwise distill pointer data 444 (identifying a portion of a clip or image depicting a person, device, or other visible entity that is or was in a vicinity of a camera, e.g.) or other specific event indications 440 from raw image data 424. One or more other data distillation modules 435, 436 may likewise be configured to recognize or otherwise distill other event indications 440 (indications of ingestion 445 or device presence, e.g.) from other raw data 425, 426.

In some contexts, one or more such event indications 440 may constitute actionable data distillations 450 (summary data 446 or determinations 447 that trigger a modification of configurable components 493 in a vessel 490, e.g.). Also in some contexts a capsule 491 or other vessel 490 may include one or more passive wireless transponders 492 or configurable components 493 (software modules or field-programmable features, e.g.) as described below. Alternatively or additionally, one or more processors 470 may be configured to apply one or more additional filters 471, 472, 473 to such distillations. In some contexts, for example, filter 473 may invoke one or more evaluation request protocols 482 or systematic archiving protocols 485 (including one or more human-executable or device-executable instructions 478 or other suitable content 475 in one or more messages 483 or records 488, e.g.).

Figure 5:
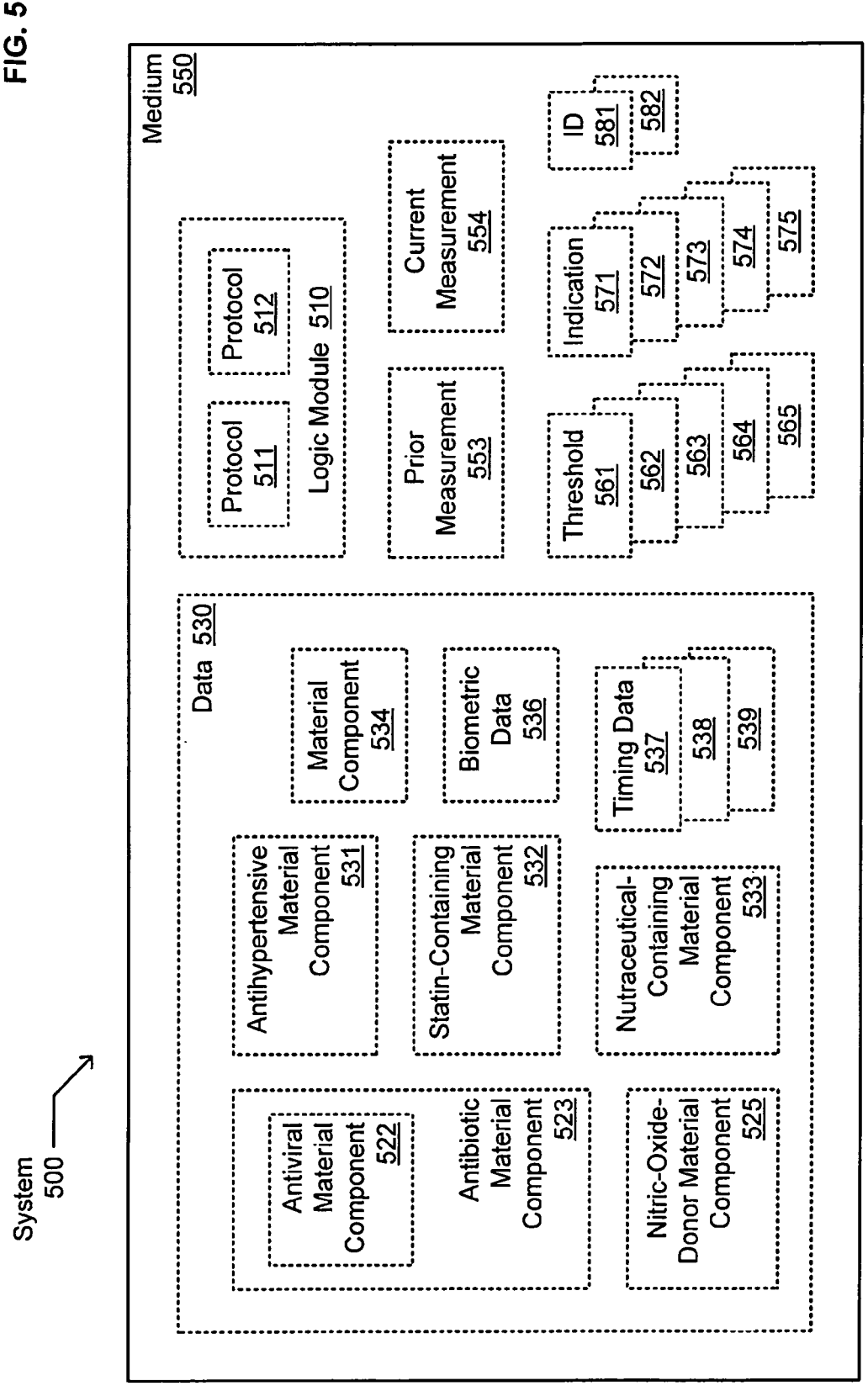
FIG. 5 depicts an exemplary environment featuring a data-handling medium.

With reference now to FIG. 5, shown is an example of a system 500 having one or more media 550 suitable for inclusion in one or more response units 355, interaction units 375, distillation units 460, or implementations 201-206 as described herein. In some contexts data 530 may include one or more components of a prescribed or actual health regimen: antiviral material components 522 or other antibiotic material components 523, nitric-oxide-donor material components 525, antihypertensive material components 531, statin-containing material components 532, nutraceutical-containing material components 533 or other material components 534, biometric data 536 (one or more prior measurements 553 or current measurements 554, e.g.), or timing data 537, 538, 539. In some contexts, moreover, a regimen that includes such a therapeutic component 181 will likewise include one or more modules 162 targeting a corresponding symptom to be monitored. For a subject 382 who has been prescribed an antihypertensive material component 531, for example, such monitoring may include asking the subject 382 or care provider 383 whether one or more of severe headache, slurred speech, nosebleed, ringing in the ear, extreme dizziness, blurred vision, or other such symptoms (measured or otherwise) associated with such a therapeutic component 181 have persisted. To facilitate such compliance and other monitoring, medium 550 may include one or more protocols 511, 512 (in one or more logic modules 510, e.g.); thresholds 561, 562, 563, 564, 565; indications 571, 572, 573, 574, 575; or identifiers 581, 582 as described below. This can occur, for example, in a context in which one or more application modules 110, products 150, or primary systems 200 include or otherwise interact with one or more instances of media 550 (via one or more networks 290, 340, e.g.) or in which one or more instances of conduits 286, storage devices 287, memories 288, or other media 550 occurs in one or more component(s) of 210-216 or 221-226 described herein.

Figure 6:
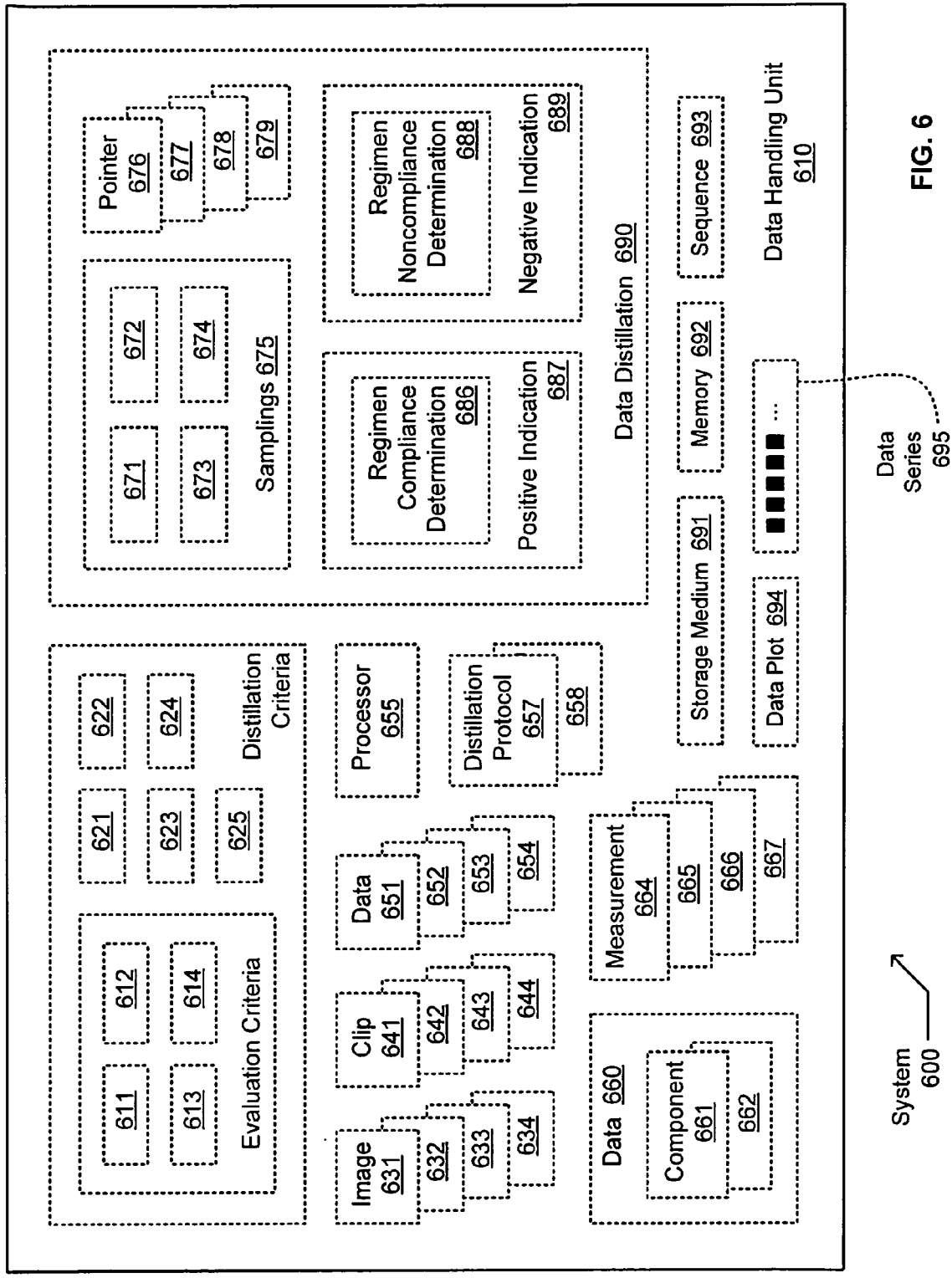
FIG. 6 depicts an exemplary environment featuring a data-handling unit.

With reference now to FIG. 6, shown is an example of a system 600 comprising a data handling unit 610 suitable for inclusion in one or more implementations 201-206 or distillation units 460 described herein. Application-specific hardware or software therein, for example, may implement one or more evaluation criteria 611, 612, 613, 614 or other data distillation criteria 621, 622, 623, 624, 625 capable of generating one or more samplings 671, 672, 673, 674, 675; pointers 676, 677, 678, 679; regimen compliance determinations 686 or other compliance-positive indications 687; regimen non-compliance determinations 688 or other compliance-negative indications 689; or other such data distillations 690. In some contexts, for example, such distillations may result from processor 655 applying one or more distillation protocols 657, 658 to process or produce one or more images 631, 632, 633, 634; clips 641, 642, 643, 644; measurements 664, 665, 666, 667; data 651, 652, 653, 654. Components 661, 662 of such data 660 may (optionally) be expressed as one or more sequences 693, data plots 694, data series 695, or otherwise in a memory 692 or on another storage medium 691 as described herein.

Figure 7:
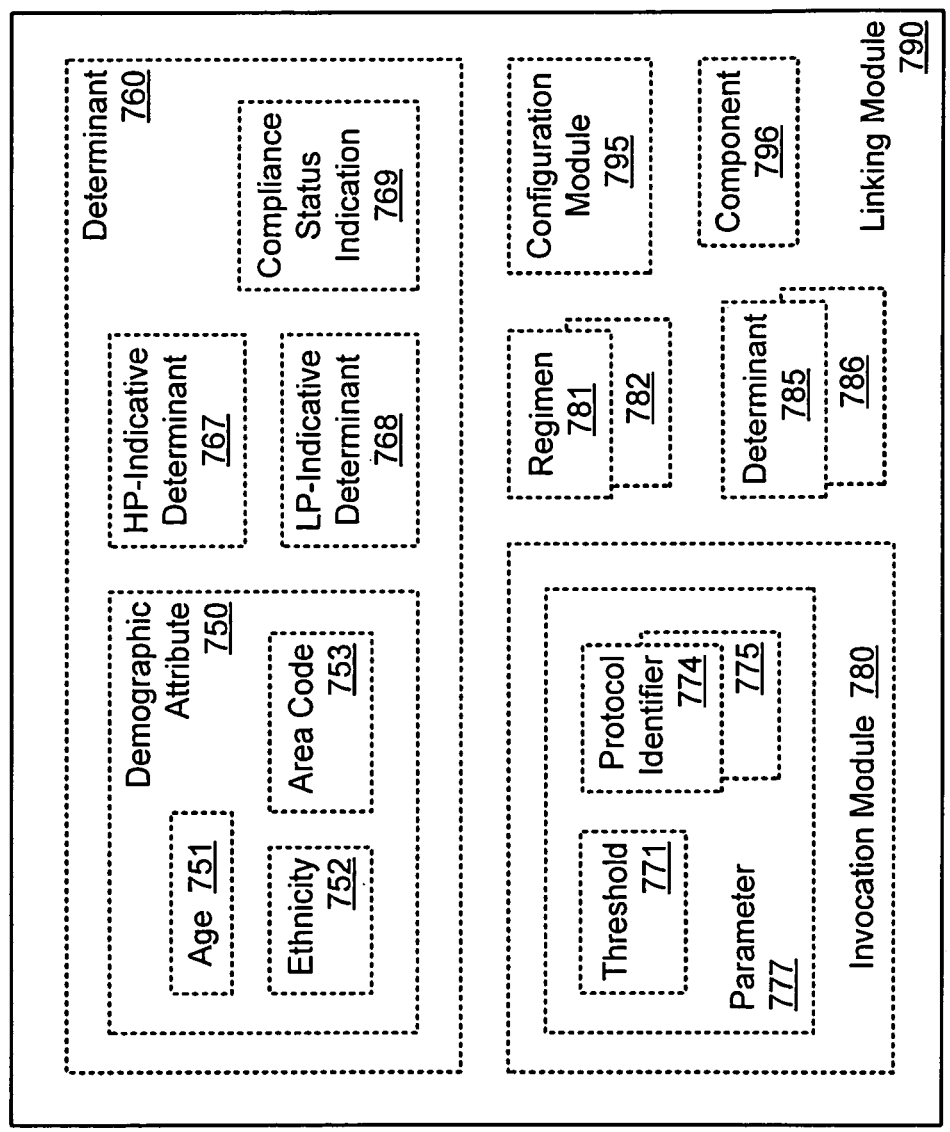
FIG. 7 depicts an exemplary environment featuring a linking module.

With reference now to FIG. 7, shown is an example of a linking module 790 that can be used to facilitate one or more operations described below (with reference to FIG. 14-19 or 26-30, e.g.) in relation to one or more application modules 110, products 150, interaction units 375, data handling units 610, or other implementations described above. In some contexts, operational modes of such components may depend upon one or more ages 751, ethnicities 752, area codes 753 or other geographic indications, compliance status indications 769, or other such determinants 760. In some contexts, for example, a shortage of bandwidth or memory 692 may constitute a low-prolixity-indicative determinant 768 so that several components of summary data 446 are transmitted or retained and corresponding raw data 410 is discarded. Alternatively or additionally, one or more individuals or devices can generate a low-prolixity-indicative determinant 768, such as a request can from technician 361 to receive a sampling, sum, abridgement, or other more-concise distillation of available raw data 410 or a report of prior failures in transmitting such raw data via linking module 790. Conversely a systematic archiving protocol 485 may be configured to respond to a high-prolixity-indicative determinant 767 (an abundance of bandwidth or memory 692, a compliance-negative indication 689, or reports of successful transmission, e.g.) by retaining and annotating several components of raw data 410 (using one or more pointers 679 to identify most-relevant components, e.g.) during archiving. For such implementations linking module 790 may likewise include one or more thresholds 771, protocol identifiers 774, 775, or other parameters 777 accessible to one or more invocation modules 780 (configured to invoke circuitry as described below, e.g.). Alternatively or additionally, linking module 790 may bear expressions (device-executable code or parameters thereof, e.g.) of one or more regimens 781, 782 or other determinants 785, 786; configuration modules 795; or other components 796 described herein.

In some variants, one or more application modules 110, data handling units 610, or linking modules 790 may include or otherwise interact with one or more components 210-216 as described herein. Alternatively or additionally, such components may likewise include or interact with one or more products 150, interaction units 375, or distillation units 460 as described herein. This can occur, for example, in a context in which such components 210-216 communicate with one or more complementary components 221-226 within primary system 200 or in or via a network 290, 340 as described herein.

Several variants described herein refer to device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

Some descriptions herein refer to a human or other subject "ingesting" a device. Such devices may include cameras, transmitters, caplets, recording components, surgical instruments, sensors, or other such articles configured to perform diagnostic, therapeutic, monitoring, or other communication functions after passing into or through a stomach.

Some descriptions herein refer to an "apparent presence" or "apparent absence" of a device. Such presence may manifest as one or more thermal, auditory, chemical, magnetic, optical, proximal, or other such attributes (selectively) characteristic of the region that can be detected by the device. Alternatively or additionally, such presence or absence may (optionally) be detectable by a sensor or other apparatus capable of detecting the device when the device is within a detection range of the apparatus.

In some embodiments, a material is "therapeutic" if it contains one or more medications or other components having a purpose or effect of relieving symptoms, reducing health risks, or otherwise promoting the subject's health. A treatment regimen may comprise one or more conditional or other "therapeutic material dispensations" and/or other aspects of treatment.

In some embodiments, a "state" of a component may comprise "available" or some other such state-descriptive labels, an event count or other such memory values, a partial depletion or other such physical property of a supply device, a voltage, or any other such conditions or attributes that may change between two or more possible values irrespective of device location. Such states may be received directly as a measurement or other detection, in some variants, and/or may be inferred from a component's behavior over time. A distributed or other composite system may comprise vector-valued device states, moreover, which may affect dispensations or departures in various ways as exemplified herein.

"Apparent," "selective," "conditional," "indicative," "normal," "compliant," "present," "coincident," "related," "biological," "partly," "responsive," "distilled," "useless," "remote," "in a vicinity," or other such descriptors herein are used in their normal yes-or-no sense, not as terms of degree, unless context dictates otherwise. In light of the present disclosure those skilled in the art will understand from context what is meant by "vicinity," by being "in" or "at" a detection region, by "remote," and by other such positional descriptors used herein. "For" is not used to articulate a mere intended purpose in phrases like "circuitry for" or "instruction for," moreover, but is used normally, in descriptively identifying special purpose circuitry or code. A "status" of one or more individuals may be vector-valued in some instances, such as if it combines two or more of (a) "compliant with medical regimen," (b) "compliant with exercise regimen," (c) "88 kilograms," (d) "late for the dosage time," or (e) "pregnant."

Some descriptions herein refer to a "data distillation." Such distillations can include an average, estimate, range, or other computation at least partly distilling a set of data. They can likewise include an indexing, sorting, summarization, distributed sampling, or other process having a purpose or effect of showing some aspect of the data more concisely or effectively than a conventional display or archiving of the entire data. Selecting a last portion of a data set can constitute a distillation, for example, in a context in which the data's utility apparently increases (medians or other cumulative computations, e.g.). In some variants, a data distillation "indicative of a regimen compliance status" may include one or more optical or other images showing an individual doing something, or showing that something has apparently been done or has apparently not been done that is required, for example, by a research or therapeutic regimen. If a physician has defined a regimen that includes a daily dose of an antihypertensive material component 531, for example, an indication that a dispenser 170 that contains such medication has not moved for a week is indicative of a regimen compliance status. So is a daily blood pressure measurement or an indication that the patient's prescription has been filled on time. Removing duplicative data or indexing available data are useful ways of "distilling" data so that it becomes manageable even while retaining some of its meaning. Those skilled in the art will recognize many useful modes of distilling data in light of the state of the art and of teachings herein.

In some embodiments, "signaling" something can include identifying, contacting, requesting, selecting, or indicating the thing. In some cases a signaled thing is susceptible to fewer than all of these aspects, of course, such as a task definition that cannot be "contacted."

In some embodiments, "status indicative" data can reflect a trend or other time-dependent phenomenon indicating some aspect of a subject's condition. Alternatively or additionally, a status indicative data set can include portions that have no bearing upon such status. Although some types of distillations can require authority or substantial expertise (e.g. making a final decision upon a risky procedure or other course of treatment), many other types of distillations can readily be implemented without undue experimentation in light of teachings herein.

In some embodiments, one or more applicable "criteria" can include maxima or other comparison values applied to durations, counts, lengths, widths, frequencies, signal magnitudes or phases, digital values, or other aspects of data characterization. In some contexts, such criteria can be applied by determining when or how often a recognizable pattern can be found: a text string, a quantity, a cough-like sound, an arrhythmia, a visible dilation, a failure to respond, a non-change, an allergic response, a symptom relating to an apparent condition of the user, or the like.

In some embodiments, "causing" events can include triggering, producing or otherwise directly or indirectly bringing the events to pass. This can include causing the events remotely, concurrently, partially, or otherwise as a "cause in fact," whether or not a more immediate cause also exists.

Some descriptions herein refer to a first event or condition having "coincided" with a second event or condition. As used herein, two events or conditions "coincide" if they are spatially coextensive or overlapping (between two devices, e.g.) and if they are roughly contemporaneous (within a few hours, e.g.).

Some descriptions herein refer to a "regimen" with which a subject may or may not "comply." Such regimens may include one or more monitoring or reporting components, ingestion or other administration components, devices or device interactions, acts of omission, actions performed by a device or parties, nutraceutical or other material components, acts that contribute toward a positive or negative accumulation defined in the regimen, or other such components that may be prescribed, discouraged, or otherwise specified.

Some descriptions herein refer to "subjects" or "individuals." Such entities may include patients, market or survey participants, subpopulations defined by one or more demographic attributes, inmates, children, livestock, subscribers, or other beings whose behavior or well-being is of interest.

Some descriptions herein refer to an "indication whether" an event has occurred. An indication is "positive" if it indicates that the event has occurred, irrespective of its numerical sign or lack thereof. Whether positive or negative, such indications may be weak (i.e. slightly probative), definitive, or many levels in between. In some cases the "indication" may include a portion that is indeterminate, such as an irrelevant portion of a useful photograph. The event may be contemporaneous or significantly before the event, in some contexts, and the indication may be explicit or implicit. An indication whether a device has been ingested by an individual, for example, may include past or present measurements (of pH or electrical conductivity, e.g.), audio or video data recorded in a vicinity of the individual or the device, control or sensor signals indicative of scheduled or detected dispenser actuation, relevant raw data from which such an event might later be inferred, or an explicit message that says "the device has been ingested."

Some descriptions herein refer to data indicating that "a portion of a container moved" or that "a therapeutic material has been administered to a portion of a subject." In some contexts, a given signal may indicate either, both, or neither of these events. As used herein, an administration "to a portion of" a subject indicates that the administration was physical (therapeutic or systemic, e.g.) and not merely a transfer of possession to the person. An "actuation in" a vessel refers to a portion of the vessel moving relative to the remainder of the vessel. Thus a detection of a movement of "a portion of" a vessel may refer to an actuation in or to a movement of the vessel. In a context in which data indicating one or more such events is not taken as definitive, additional data relevant to the same hypothesis/hypotheses may be combined with the prior indication(s) as described herein.

Some descriptions herein refer to a "threshold frequency," in relation to a wireless transmission region's energy response or distribution, above which energy begins to be attenuated or otherwise reduced by at least 3 decibels (relative to a passband or lowpass nominal value, e.g.). A frequency range "extends" above or below a given frequency if the frequency bounds the range or if the range spans the frequency.

In light of teachings herein, numerous existing techniques may be applied for configuring special-purpose circuitry or other structures effective for implementing measurement and imaging as described herein without undue experimentation. See, e.g., U.S. Pat. No. 7,308,292 ("Optical-based sensing devices"); U.S. Pat. No. 7,305,262 ("Apparatus and method for acquiring oximetry and electrocardiogram signals"); U.S. Pat. No. 7,280,858 ("Pulse oximetry sensor"); U.S. Pat. No. 7,004,907 ("Blood-pressure monitoring device featuring a calibration-based analysis"); U.S. Pat. No. 5,755,741 ("Body position and activity sensor"); U.S. Pat. No. 5,601,811 ("Substantive water-soluble cationic UV-absorbing compounds"); U.S. Pub. No. 2003/0050542 ("Device for in-vivo measurement of the concentration of a substance contained in a body fluid"); U.S. Pub. No. 2002/0016535 ("Subcutaneous glucose measurement device") or U.S. Pat. No. 7,181,054 ("System for processing image representative data").

With reference now to FIG. 8, shown is a system 800 in which one or more technologies may be implemented. Commode 810 is configured to include or support a primary system 200 that includes one or more monitor units 850 having one or more receivers 831, transmitters 832, or sensors 833 configured to detect or interact with one or more devices 860 that may be present in a bowl 830 of the commode. Monitor unit 850 may likewise include one or more buttons 835 or other controls that can be actuated by a layperson (subject 382, e.g.). In some contexts, monitor unit 850 may further include one or more memories 845 (containing one or more images 841, 842 of the inside of the bowl 830; one or more detection modules 870 configured to bear data 861, 862, 863; logic modules 875; control modules 880; or other media 881, 882 as described herein. Alternatively or additionally, system 800 may include one or more application modules 110, interaction units 375, distillation units 460, data handling units 610, linking modules 790, or other secondary units 820 as described herein.

With reference now to FIG. 14, shown is a high-level logic flow 1400 of an operational process. Operation 10 describes detecting a first indication whether a first device has been ingested in content of a signal from the first device (e.g. detection module 870 detecting data 861 from a vessel 160 or other device 860 via receiver 831, the data containing a measurement 183, 664 or other ingestion-indicative feature state 173 manifesting the "first" indication, relating to whether a vessel 160 or other device 860 has been ingested). This can occur, for example, in a context in which a monitor unit 850 or detection unit 180 and one or more devices 860 corresponding thereto are obtained in a kit; in which such correspondence is established at least by virtue of such a unit being configured to respond selectively to the device(s); and in which each such device 860 was constructed and arranged with a human-digestible sensor coating (over one or more contacts of acid-activated sensors 2164 or other sensors 2166, 2167, e.g.) such that the arrival of specific data 862 indicating a now-uncoated sensor of device 860 tends to confirm or otherwise indicate that the device 860 has been ingested. In some contexts, sensor 833 or device 860 may be configured to generate data 530 containing one or more colorimetric, chemical, or other device-detectable attributes of fecal samples or digestive fluids. Alternatively or additionally, component 210 may include an instance of device-executable code 101 configured to permit one or more processors 115, 295 or application-specific circuitry to perform variants of operation 10 as described herein.

Operation 11 describes detecting an apparent presence of or absence of a first device at a toilet as a second indication whether the first device has been ingested (e.g. sensor 833 detecting the same device in or near bowl 830, or the absence thereof, as digital data 862). This can occur, for example, in a context in which button 835, a seat movement or deformation, a room's light switch turning off, a signal from secondary unit 820, or some other suitable actuator or event triggers a low range or directional transmitter 832 to send one or more radio frequency activation pulses into bowl 830; in which device 860 contains a passive radio frequency identification (RFID) element activated by transmitter 832; in which detection module 870 has detected wireless data 861 from device 860 (as described above) via receiver 831; and in which data 862 contains the "second" indication. In such contexts, the recognition of such wireless data 862 tends to corroborate or otherwise indicate that the device has been ingested. Alternatively or additionally, component 211 may include an instance of device-executable code 102 configured to permit one or more processors 115, 295 or application-specific circuitry to perform variants of operation 11 as described herein. In a context in which receiver 831 performs operation 11, also, the received signal may contain a measurement 183 or other indication 573 whether the device was ingested earlier (as the "first" or other confirmatory indication, e.g.).

In light of teachings herein, numerous existing techniques may be applied for configuring special-purpose circuitry or other structures effective for detecting whether an object is within a region of interest as described herein without undue experimentation. See, e.g., U.S. Pat. No. 7,821,404 ("Systems and methods for improved health care compliance"); U.S. Pat. No. 7,140,050 ("Automatic flushing actuator for tank style toilet"); U.S. Pat. No. 7,032,816 ("Communication between machines and feed-forward control in event-based product manufacturing"); U.S. Pat. No. 7,666,132 ("Anal incontinence disease treatment with controlled wireless energy supply"); U.S. Pat. No. 7,350,402 ("Method and apparatus for determination of medical diagnostics utilizing biological fluids"); U.S. Pat. No. 6,893,879 ("Method for separating analyte from a sample"); U.S. Pat. No. 7,733,224 ("Mesh network personal emergency response appliance"); U.S. Pat. No. 7,940,049 ("Portable wireless metal detector"); U.S. Pat. No. 7,012,504 ("Wireless identification device, RFID device with push-on/push off switch, and method of manufacturing wireless identification device"); U.S. Pat. No. 7,809,857 ("Method and system to collect geographic location information for a network address utilizing geographically dispersed data collection agents"); U.S. Pat. No. 7,876,228 ("Method and apparatus for monitoring ingestion of medications using an implantable medical device"); U.S. Pub. No. 2006/0285441 ("Systems and methods for improved health care compliance"); U.S. Pub. No. 2007/0123772 ("Medication compliance system and associated methods").

Operation 21 describes signaling a data distillation indicative of a regimen compliance status partly based on the first indication whether the first device has been ingested in the content of the signal from the first device and partly based on the apparent presence of or absence of the first device at the toilet as the second indication whether the first device has been ingested (e.g. control module 880 indicating a successful dosage or other positive determinant 785 bearing upon the subject's past or present regimen compliance and based at least upon the "first" and "second" indications). This can occur, for example, in a context in which control module 880 transmits no signal across media 882 unless and until such "second" and "first" indications are received. Alternatively or additionally, control module 880 may be configured to transmit timing data 539 across media 882 if another indication that the device has been ingested arrives and otherwise to store an image 842 or other data 863 on one or more archiving media 881. Alternatively or additionally, component 221 may include an instance of device-executable code 103 configured to permit one or more processors 115, 295 or application-specific circuitry to perform variants of operation 21 as described below. In an embodiment in which component 221 includes a data handling unit 610 configured to perform operation 21, for example, a data output 251 transmitted across linkage 250 may include a positive indication 687 (of likely regimen compliance) conditionally upon both output data 231 and output data 232 indicating that a particular vessel 160 or other device 860 was ingested. This can occur, for example, in a context in which there will otherwise be no data output 251 or in which data output 251 will otherwise include a regimen noncompliance determination 688 or other such negative indication 689 (indicating "unknown" compliance status, e.g.). This can occur, for example, in a context in which such a vessel 160 initially includes one or more therapeutic components 181 administered by ingestion and characterized by a regimen that includes an antiviral material component 522 or other material components 534 as described herein, for which timing data 538, 539 may be a significant aspect of compliance. Alternatively or additionally, component 221 may include an instance of device-executable code 103 configured to permit one or more processors 115, 295 or application-specific circuitry to perform variants of operation 21 as described below.

In light of teachings herein, numerous existing techniques may be applied for configuring special-purpose circuitry or other structures effective for signaling a data distillation indicative of a regimen compliance status partly based on content of a signal from a device or a location of a device as described herein without undue experimentation. See, e.g., U.S. Pat. No. 7,062,312 ("Combination and method including a visual marker for determining compliance with a medication regimen"); U.S. Pat. No. 7,945,457 ("Distributed system for monitoring patient video, audio and medical parameter data"); U.S. Pat. No. 7,931,592 ("Systems and methods for monitoring health and delivering drugs transdermally"); U.S. Pat. No. 7,484,129 ("Physiologic event monitoring device having robust internal control"); U.S. Pat. No. 6,527,729 ("Method for monitoring patient using acoustic sensor"); U.S. Pat. No. 7,991,628 ("Generating output data based on patient monitoring"); U.S. Pat. No. 7,945,461 ("Prescription compliance monitoring system"); U.S. Pat. No. 7,690,378 ("Methods, systems and devices for monitoring respiratory disorders"); U.S. Pat. No. 7,011,814 ("Systems, methods and devices for in vivo monitoring of a localized response via a radiolabeled analyte in a subject"); U.S. Pat. No. 6,696,924 ("Hand-held apparatus for monitoring drug-nutrient-mineral interactions and method therefor"); U.S. Pat. No. 7,972,296 ("Fluid component analysis system and method for glucose monitoring and control"); U.S. Pat. No. 6,949,511 ("Methods of inhibiting angiogenesis via increasing in vivo concentrations of kringle region fragments of plasminogen").

Some instances of flow 1400 may (optionally) be performed by one or more instances of server 294 that are remote from primary system 200 but operable to cause output device(s) 276 to receive and to present or cause results via linkage 250. Alternatively or additionally, device-detectable data 232 may be borne by one or more instances of integrated circuits 274, signal-bearing conduits 286, holding devices 289, or the like as described herein. Such data may optionally be configured for transmission (in operation 21, e.g.) by a semiconductor chip or other embodiment of integrated circuit 274 that contains or is otherwise operatively coupled with antenna 275 (in a radio-frequency identification tag, for example).

In some variants, flow 1400 may be implemented entirely within primary system 200. Operation 10 may be implemented by configuring component 210 as logic for detecting a first indication whether a first device has been ingested in content of a signal from the first device, for example, such as by including special-purpose instruction sequences or special-purpose-circuit designs for this function. Operation 11 may likewise be implemented by configuring component 211 as logic for detecting an apparent presence of or absence of a first device at a toilet as a second indication whether the first device has been ingested. Output data 231 from components 210, 211 (combined on one chip, e.g.) in primary system 200 or network 290 may be recorded into available portions of storage device(s) 287 or sent to component 221, for example. Component 221 may likewise perform operation 21 via implementation as logic for signaling a data distillation indicative of a regimen compliance status partly based on the first indication whether the first device has been ingested in the content of the signal from the first device and partly based on the apparent presence of or absence of the first device at the toilet as the second indication whether the first device has been ingested, for example. Implementation output data 232 from such a component in primary system 200 or network 290 may be recorded into available portions of storage device(s) 287 or sent to processor 295, for example. Each portion of implementation 201 may likewise include one or more instances of software, hardware, or the like implementing logic that may be expressed in several respective forms as described herein or otherwise understood by those skilled in the art.

Figure 9:
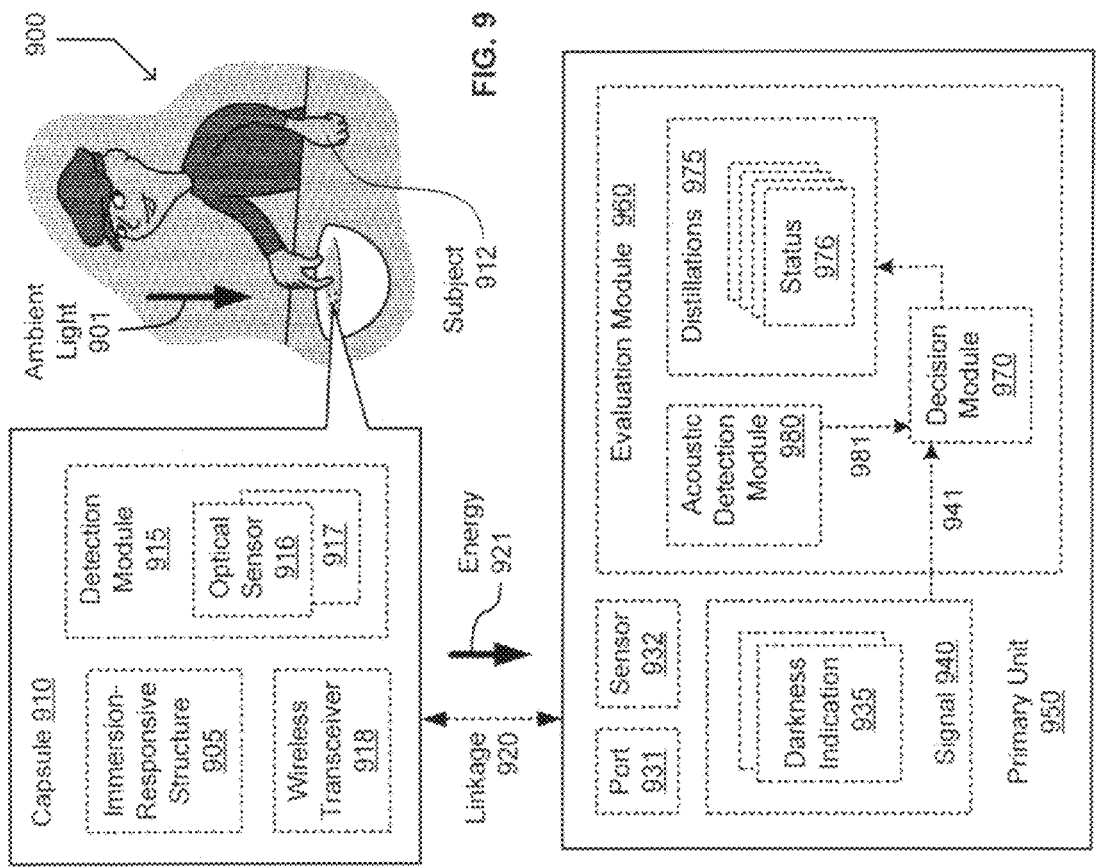
FIG. 9 depicts an exemplary environment featuring an ingestible capsule.

With reference now to FIG. 9, shown is a system 900 in which one or more technologies may be implemented for thwarting a subject 912 who is attempting to circumvent one or more compliance monitoring mechanisms, such as by immersing a capsule 910 in warm water in lieu of ingesting it. In some configurations, capsule 910 may include one or more immersion-responsive structures 905 (a water-soluble coating or moisture or pressure sensor, e.g.), detection modules 915 (including one or more optical sensors 916, optionally configured to detect ambient light 901, or other sensors 917 as described herein, e.g.), or wireless transceivers 918 providing a linkage 920 with a primary system 200 that includes one or more primary units 950 having one or more ports 931, sensors 932 (optionally configured to detect radio frequency or other energy 921, e.g.), signals 940 (manifesting a darkness indication 935 or other such indication 941 of an absence of a higher-frequency signal adjacent capsule 910, e.g.), and evaluation modules 960. Alternatively or additionally, evaluation module 960 may include one or more acoustic detection modules 980 manifesting an indication 981 of a presence of a lower-frequency signal (adjacent capsule 910, e.g.) to one or more decision modules 970 that generate a regimen compliance status 976 or other data distillations 975 as described below. Alternatively or additionally, primary unit 950 may be operably coupled with one or more application modules 110, distillation units 460, linking modules 790, or other data handling units as described herein.

Figure 15:
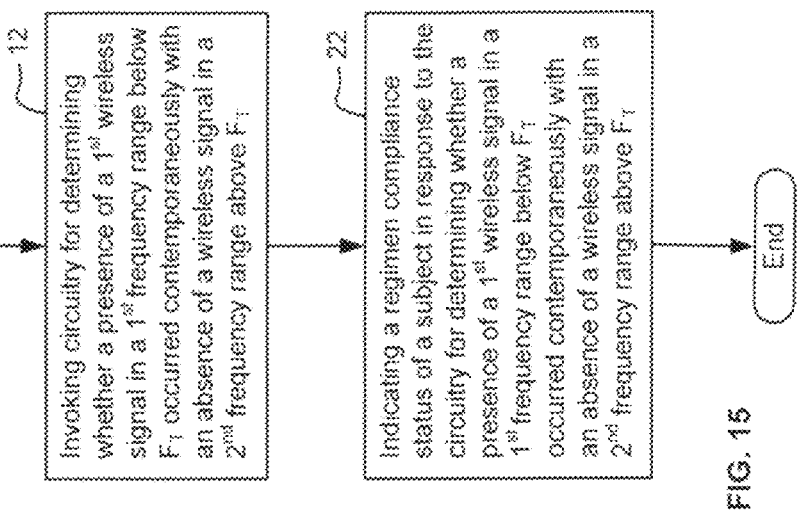
FIG. 15 depicts a high-level logic flow of an operational process described with reference to FIG. 9.

With reference now to FIG. 15, shown is a high-level logic flow 1500 of an operational process. Operation 12 describes invoking circuitry for determining whether a presence of a wireless signal in a first frequency range below a threshold frequency occurred contemporaneously with an absence of a wireless signal in a second frequency range above the threshold frequency (e.g. decision module 970 selectively generating a positive signal in response to indications of sound being detected in or near capsule 910 during a period in which an absence of ambient light 901 is also detected at capsule 910). This may occur, for example, in a context in which acoustic detection module 980 receives an output from one or more sensors 932 signaling a lower-frequency energy 921 characteristic of capsule 910 (ultrasound energy leaving the capsule, e.g.); in which the "threshold frequency" is taken to be a system component's cutoff frequency (one or more sensors 917, 932, for example, having a 3 dB cutoff frequency in the gigahertz or in the terahertz range); in which optical sensor 916 transmits signal 940 containing a darkness indication 935 if it is in a dark environment; and in which decision module 970 implements an "AND" function. In some variants capsule 910 may contain an ultrasound identification (USID) component, for example, and the applicable threshold frequency ($F_T$) may be a 3 dB cutoff frequency of one or more sensors in the system 900. Alternatively or additionally, component 212 may include an instance of device-executable code 102 configured to permit one or more processors 115, 295 or application-specific circuitry to perform variants of operation 12 as described herein. In some contexts such variants may generate a negative signal, indicating that no detection of such a "presence" appeared to coincide with a detection of such an "absence," for example, unless such conditions occurred within a specific interval (of a second or a minute, for example) of one another.

In light of teachings herein, numerous existing techniques may be applied for configuring special-purpose circuitry or other structures effective for determining whether particular combinations of device-detectable phenomena are present in an environment as described herein without undue experimentation. See, e.g., U.S. Pat. No. 7,727,156 ("Dual frequency band ultrasound transducer arrays"); U.S. Pat. No. 7,517,346 ("Radio frequency ablation system with integrated ultrasound imaging"); U.S. Pat. No. 7,232,431 ("Intradermal incorporation of microparticles containing encapsulated drugs using low frequency ultrasound"); U.S. Pat. No. 6,438,399 ("Multi-wavelength frequency domain near-infrared cerebral oximeter"); U.S. Pat. No. 7,574,141 ("Repeating radio frequency transmission system for extending the effective operational range of an infrared remote control system"); U.S. Pat. No. 6,782,208 ("Wireless communication device and method having coordinated primary and secondary transmitters"); U.S. Pat. No. 7,970,208 ("Apparatus to detect homogeneous region of image using adaptive threshold"); U.S. Pat. No. 7,282,926 ("Method and an apparatus for characterizing a high-frequency device-under-test in a large signal impedance tuning environment"); U.S. Pat. No. 7,385,557 ("PIFA device for providing optimized frequency characteristics in a multi-frequency environment and method for controlling the same"); U.S. Pat. No. 7,357,030 ("Apparatus and methods for determining at least one characteristic of a proximate environment"); U.S. Pat. No. 7,920,991 ("Characterizing the capacity region in multi-channel, multi-radio mesh networks"); U.S. Pat. No. 6,175,811 ("Method for frequency environment modeling and characterization"); U.S. Pat. No. 7,789,834 ("Plaque characterization using multiple intravascular ultrasound datasets having distinct filter bands"); U.S. Pat. No. 7,340,381 ("Characterization of radio frequency (RF) signals using wavelet-based parameter extraction").

Operation 22 describes indicating a regimen compliance status of a subject in response to the circuitry for determining whether a presence of a wireless signal in a first frequency range below a threshold frequency occurred contemporaneously with an absence of a wireless signal in a second frequency range above the threshold frequency (e.g. evaluation module 960 generating and storing a 1-10 score or an A-F grade indicative of a current status of a subject 382, 912 in relation to a daily or other regimen 782). This can occur, for example, in a context in which a subject's cumulative status 976 increments or decrements (by a point or half-grade, e.g.) respectively in response to a positive or negative indication (from operation 12, e.g.); in which optical sensor 916 can detect ambient light 901 (if subject 912 has not ingested capsule 910, e.g.); and in which a deliberate effort at generating a fraudulent indication of compliance (such as by immersing capsule 910 in a bowl of water at 37° C. (centigrade), for example, calculated to fool a temperature-responsive detection module 915 into falsely indicating that capsule 910 had been ingested) would otherwise go unnoticed. Alternatively or additionally, evaluation module 960 may implement other components of distillation unit 460 or other data handling units 610 as described herein, such as for generating a regimen compliance determination 686, warning, or other message ("not reliable," e.g.) conditionally (as a compliance status indication 769 or other data distillation 690, e.g.). In some contexts, capsule 910 may implement device 860 as described above so that such distillations 975 may (optionally) include chemical sensor output or other indications whether capsule 910 has been ingested in content of a signal from capsule 910. Alternatively or additionally, a vessel 160 may contain some instances of capsule 910 of a first type (able to detect only light or sound, e.g.) and others of a second type (able to detect ingestion-indicative phenomena different from that of the first type, e.g.), optionally in a context in which primary unit 950 is configured to detect either type of capsule 910. By combining two or more visually indistinguishable species of capsule (able to detect different phenomena, e.g.) in a vessel, compliance monitoring becomes much more difficult for a subject 912 to thwart. Alternatively or additionally, cost-effective implementations may include one or more non-sensor-containing capsules that are likewise visually indistinguishable to a subject. In some contexts, such updated regimen compliance indications or other messages may be transmitted periodically (weekly, e.g.) to a subscriber or other subject 382 or others (care provider 383, e.g.). Alternatively or additionally, component 222 may include an instance of device-executable code 103 configured to permit one or more processors 115, 295 or application-specific circuitry to perform variants of operation 22 as described herein.

In light of teachings herein, numerous existing techniques may be applied for configuring special-purpose circuitry or other structures effective for signaling a status in relation to a recommended or required regimen as described herein without undue experimentation. See, e.g., U.S. Pat. No. 7,975,543 ("Method for carrying out isometric exercise regimen"); U.S. Pat. No. 7,747,454 ("System and method for real time management of a drug regimen"); U.S. Pat. No. 7,712,288 ("Unified ingestion package and process for patient compliance with prescribed medication regimen"); U.S. Pat. No. 7,911,348 ("Methods for refining patient, staff and visitor profiles used in monitoring quality and performance at a healthcare facility"); U.S. Pat. No. 7,941,323 ("Remote health monitoring and maintenance system"); U.S. Pat. No. 7,853,455 ("Remote health monitoring and maintenance system"); U.S. Pat. No. 7,680,690 ("Intelligent menu ordering system"); U.S. Pat. No. 7,973,043 ("Combination therapy for depression, prevention of suicide, and various medical and psychiatric conditions"); U.S. Pat. No. 7,820,108 ("Marker detection method and apparatus to monitor drug compliance"); U.S. Pat. No. 7,991,628 ("Generating output data based on patient monitoring"); U.S. Pat. No. 7,991,485 ("System and method for obtaining, processing and evaluating patient information for diagnosing disease and selecting treatment").

Some instances of flow 1500 may (optionally) be performed by one or more servers 294 that are remote from primary system 200 but operable to cause output device(s) 276 to receive and to present or cause results via linkage 250. Alternatively or additionally, device-detectable data 234 may be borne by one or more instances of integrated circuits 274, signal-bearing conduits 286, holding devices 289, or the like as described herein. Such data may optionally be configured for transmission (in operation 22, e.g.) by a semiconductor chip or other embodiment of integrated circuit 274 that contains or is otherwise operatively coupled with antenna 275 (in a radio-frequency identification tag, for example).

In some variants, flow 1500 may be implemented entirely within primary system 200. Operation 12 may (optionally) be implemented by configuring component 212 as logic for determining whether a presence of a wireless signal in a first frequency range below a threshold frequency occurred contemporaneously with an absence of a wireless signal in a second frequency range above the threshold frequency, for example, such as by including special-purpose instruction sequences or special-purpose-circuit designs for this function. Output data 233 from component 212 in primary system 200 or network 290 may be recorded into available portions of storage device(s) 287 or sent to component 222, for example. Component 222 may likewise perform operation 22 via implementation as logic for indicating a regimen compliance status of a subject in response to the circuitry for determining whether a presence of a wireless signal in a first frequency range below a threshold frequency occurred contemporaneously with an absence of a wireless signal in a second frequency range above the threshold frequency, for example. Implementation output data 234 from such a component in primary system 200 or network 290 may be recorded into available portions of storage device(s) 287 or sent to processor 295, for example. Each portion of implementation 202 may likewise include one or more instances of software, hardware, or the like implementing logic that may be expressed in several respective forms as described herein or otherwise understood by those skilled in the art.

With reference now to FIG. 10, shown is a system 1000 in which one or more technologies may be implemented for systematic data distillation. In some configurations, one or more vessels 1010 (capsules, implants, patches, or other therapeutic or monitoring devices, e.g.) are used for monitoring one or more study participants or other subjects 1082. This can occur, for example, in a context in which vessel 1010 includes a vessel body 1045; one or more sensors 1011, 1012, 1013; transmission modules 1030 configured to transmit or receive a wireless signal 1034; or actuators 1051, 1052. Alternatively or additionally, one or more such components may initially be in a disabled state (e.g. by virtue of one or more coatings or other barriers 1018; actuation circuitry as described herein; or other such disablement structures 1020). In some contexts, for example, vessel 1010 may comprise one or more ingestible vessels including one or more conditional disablement structures configured to prevent (disable in situ, e.g.) transmission module 1030 from generating any wireless signal until after an in situ detection of a bodily fluid or other composition of matter (dissolving or melting one or more barriers 1018 or causing one or more sensors 1011-1013, for example, to activate transmission module 1030 to transmit a wireless signal 1034 detectable by detection device 1090 ex situ). Alternatively or additionally, in some variants, one or more vessels 1010 or other products 150 may transmit such signals (via antenna 185, e.g.) to one or more application modules 110, distillation units 460, linking modules 790, or other data handling units as described herein (implementing detection device 1090, e.g.).

Figure 23:
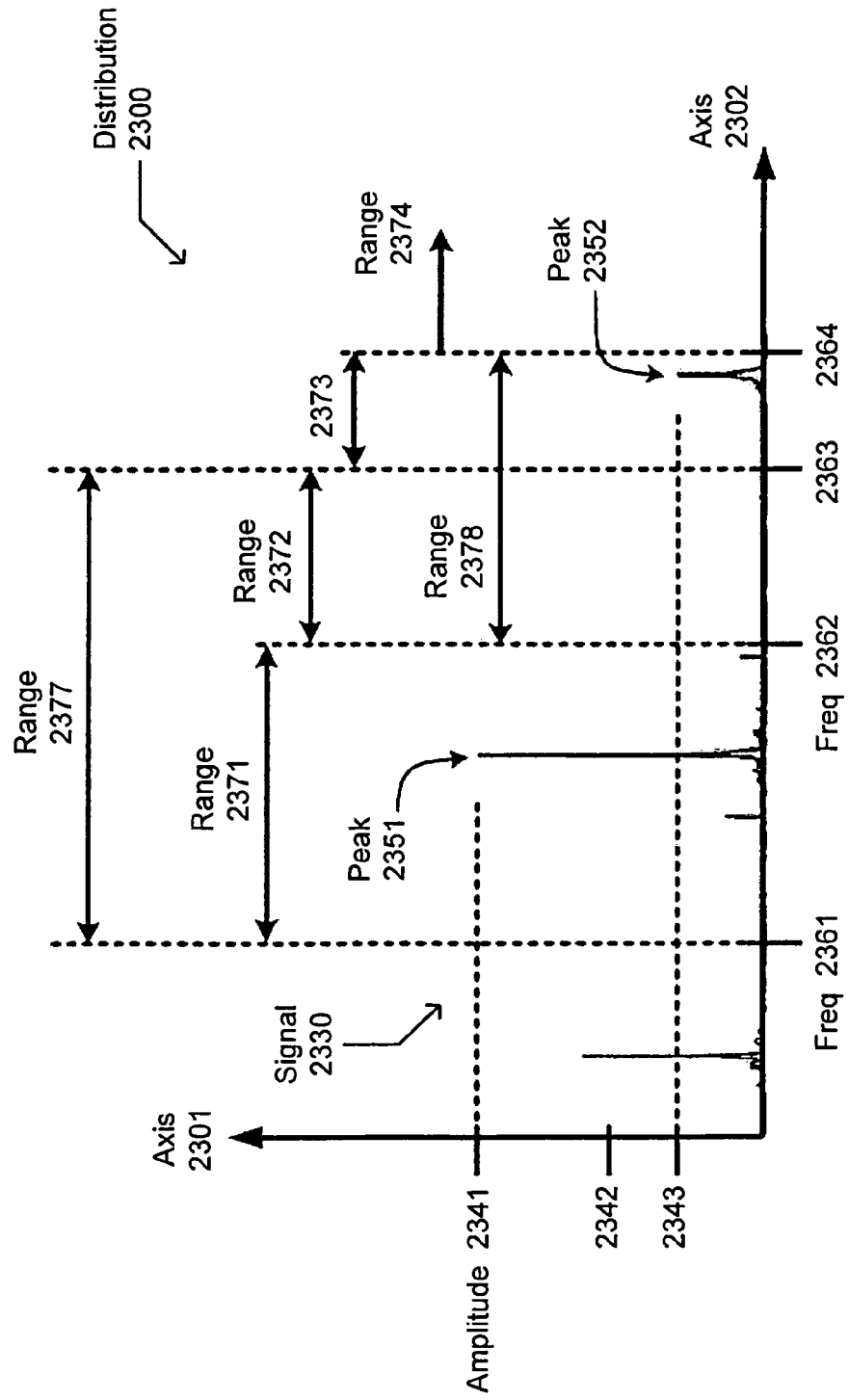
FIG. 23 depicts a frequency-domain energy distribution.

With reference now to FIG. 16, shown is a high-level logic flow 1600 of an operational process. Operation 13 describes configuring wireless signal transmission circuitry for generating a device-detectable wireless transmission (e.g. configuration module 795 transmitting software updates to modify transmission module 1030 of vessel 1010 to transmit a wireless signal 1034 in a higher or lower frequency band as depicted in FIG. 23). This can occur, for example, in a context in which an ingestible vessel body 1045 has been configured to contain transmission module 1030; in which a barrier 1018 or other conditional disablement structure 1020 is initially configured to disable transmission module 1030 from generating any wireless signal detectable by any ex situ device 1090 (until after an indication that vessel 1010 has been ingested by or otherwise administered to subject 1082, e.g.). Such an indication can be provided as a component of regimen compliance, for example, as an enabling signal from one or more sensors 1011, 1012 of pH, temperature, conductivity, recognizable auditory or optical phenomena, or other indicia of contact in situ with tissue or bodily fluid (of subject 1082, e.g.). Alternatively or additionally, such a positive indication 687 relating to regimen compliance may manifest as a dissolution or other movement of a coating (soluble in one or more digestive fluids, e.g.) or other barrier 1018 (holding a self-closing switch open, e.g.) that enables one or more sensors 1012, 1013 to detect whether a second (confirmatory, e.g.) indication of compliance or other compliance status data distillations 690 as described herein are present. In some variants, one or more such bodies 1045 may contain a liquid or other therapeutic material 1046 releasable (a) by a movement of a valve or other actuator 1052 relative to body 1045 or (b) by a barrier 1018 dissolving or melting conditionally (in response to one or more in vivo conditions, e.g.). Alternatively or additionally, component 213 may include an instance of device-executable code 102 configured to permit one or more processors 115, 295 or application-specific circuitry to perform variants of operation 13 as described herein. (Additional instances of tuning or otherwise configuring the wireless signal transmission circuitry may occur, of course, such as during manufacture.)

In light of teachings herein, numerous existing techniques may be applied for configuring special-purpose circuitry or other structures effective for transmitting a device-detectable wireless transmission out of a subject as described herein without undue experimentation. See, e.g., U.S. Pat. No. 7,720,488 ("RFID wireless 2G, 3G, 4G internet systems including Wi-Fi, Wi-Max, OFDM, CDMA, TDMA, GSM"); U.S. Pat. No. 7,621,863 ("Urinary incontinence treatment with wireless energy supply"); U.S. Pat. No. 7,460,904 ("Wireless systems and methods for the detection of neural events using onboard processing"); U.S. Pat. No. 6,577,893 ("Wireless medical diagnosis and monitoring equipment"); U.S. Pat. No. 7,967,439 ("Wireless scleral search coil including systems for measuring eye movement and methods related thereto"); U.S. Pat. No. 6,907,291 ("Secure telemetry system and method for an implantable cardiac stimulation device"); U.S. Pat. No. 7,630,736 ("Method and system for spatial data input, manipulation and distribution via an adaptive wireless transceiver"); U.S. Pat. No. 7,933,642 ("Wireless ECG system"); U.S. Pat. No. 7,782,190 ("Implantable device and system and method for wireless communication"); U.S. Pat. No. 7,786,845 ("Method and apparatus for wireless communication of identification information between radio frequency devices"); U.S. Pat. No. 6,265,963 ("Methods of processing wireless communication, methods of processing radio frequency communication, and related systems"); U.S. Pat. No. 6,806,808 ("Wireless event-recording device with identification codes"); U.S. Pat. No. 7,849,752 ("Method and system for passive wireless strain gauge"); U.S. Pat. No. 7,926,491 ("Method and apparatus for sensing field strength signals to estimate location of a wireless implantable marker"); U.S. Pat. No. 7,125,382 ("Embedded bio-sensor system"); U.S. Pat. No. 7,041,941 ("Medical item thermal treatment systems and method of monitoring medical items for compliance with prescribed requirements"); U.S. Pat. Pub. No. 2007/0008113 ("System to monitor the ingestion of medicines"); U.S. Pat. Pub. No. 2006/0289640 ("Oral drug compliance monitoring using radio frequency identification tags"); U.S. Pat. Pub. No. 2006/0210626 ("Radio frequency identification pharmaceutical tracking system and method"); U.S. Pat. Pub. No. 2006/0061472 ("Trackable pills with electronic ID tags"). See also Moore, "The Potential Use of Radio Frequency Identification Devices for Active Monitoring of Blood Glucose Levels," J. Diabetes Sci. Technol. 3: 180-183, 2009.

Operation 23 describes causing the wireless signal transmission circuitry in situ to initiate a wireless transmission detectable by an ex situ device in response to a material-selective in situ detection of a biological material (e.g. disablement structure 1020 or actuator 1051 responding to contact with tissue or bodily fluid in subject 1082 by permitting transmission module 1030 to transmit a wireless signal 1034). This can occur, for example, in a context in which one or more sensors 1012, 1013 detect at least one condition as described herein and in which transmission module 1030 is configured to respond to one or more outputs from such sensors by transmitting one or more wireless signals 1034 potentially detectable by a receiver or other detection device 1090 ex situ. In a context in which vessel 1010 is an adhesive patch or other externally wearable apparatus, for example, wireless signal 1034 may be an optical signal (a fluorescent or other distinctive color, e.g.) selectively detectable by a photodetector. In some such external applications, moreover, the disabling structure 1020 or actuator 1051 may perform operation 23 by causing ex vivo transmission circuitry transmission module 1030 to generate the wireless signal 1034 in response to an ex vivo detection (via sensor 1013, e.g.) of a biological material (a composition of matter derived from living sources, e.g.). Alternatively or additionally, component 223 may include an instance of device-executable code 103 configured to permit one or more processors 115, 295 or application-specific circuitry to perform variants of operation 23 as described herein.

In light of teachings herein, numerous existing techniques may be applied for configuring special-purpose circuitry or other structures effective for configuring chemical or other sensors, semi-permeable barriers, special-purpose circuitry, and/or other features responsive to biological conditions into various structures effective for selectively detecting a presence of living tissue or other biological material (as distinct from a null hypothesis, e.g.) as described herein without undue experimentation. See, e.g., U.S. Pat. No. 7,983,458 ("In vivo autonomous camera with on-board data storage or digital wireless transmission in regulatory approved band"); U.S. Pat. No. 7,941,162 ("System for providing alert-based services to mobile stations in a wireless communications network"); U.S. Pat. No. 7,839,153 ("Communicating with an implanted wireless sensor"); U.S. Pat. No. 7,978,062 ("Medical data transport over wireless life critical network"); U.S. Pat. No. 7,452,334 ("Antenna stent device for wireless, intraluminal monitoring"); U.S. Pat. No. 7,965,180 ("Wireless sensor device"); U.S. Pat. No. 7,808,090 ("Wireless chip"); U.S. Pat. No. 7,877,120 ("Battery-operated wireless-communication apparatus and method"); U.S. Pat. No. 7,988,917 ("Analytical test element with wireless data transmission"); U.S. Pat. No. 7,226,442 ("Microchip reservoir devices using wireless transmission of power and data"); U.S. Pat. No. 6,454,700 ("Heartburn and reflux disease treatment apparatus with wireless energy supply"); U.S. Pat. No. 6,319,510 ("Gum pad for delivery of medication to mucosal tissues").

Some instances of flow 1600 may (optionally) be performed by one or more servers 294 that are remote from primary system 200 but operable to cause output device(s) 276 to receive and to present or cause results via linkage 250. Alternatively or additionally, device-detectable data 236 may be borne by one or more instances of integrated circuits 274, signal-bearing conduits 286, holding devices 289, or the like as described herein. Such data may optionally be configured for transmission (in operation 23, e.g.) by a semiconductor chip or other embodiment of integrated circuit 274 that contains or is otherwise operatively coupled with antenna 275 (in a radio-frequency identification tag, for example).

In some variants, flow 1600 may be implemented entirely within primary system 200. Operation 13 may (optionally) be implemented by configuring component 213 as logic for generating a device-detectable wireless transmission, for example, such as by including special-purpose instruction sequences or special-purpose-circuit designs for this function. Output data 235 from component 213 in primary system 200 or network 290 may be recorded into available portions of storage device(s) 287 or sent to component 223, for example. Component 223 may likewise perform operation 23 via implementation as logic for causing the wireless signal transmission circuitry in situ to initiate a wireless transmission detectable by an ex situ device in response to a material-selective in situ detection of a biological material, for example. Implementation output data 236 from such a component in primary system 200 or network 290 may be recorded into available portions of storage device(s) 287 or sent to processor 295, for example. Each portion of implementation 203 may likewise include one or more instances of software, hardware, or the like implementing logic that may be expressed in several respective forms as described herein or otherwise understood by those skilled in the art.

Figure 11:
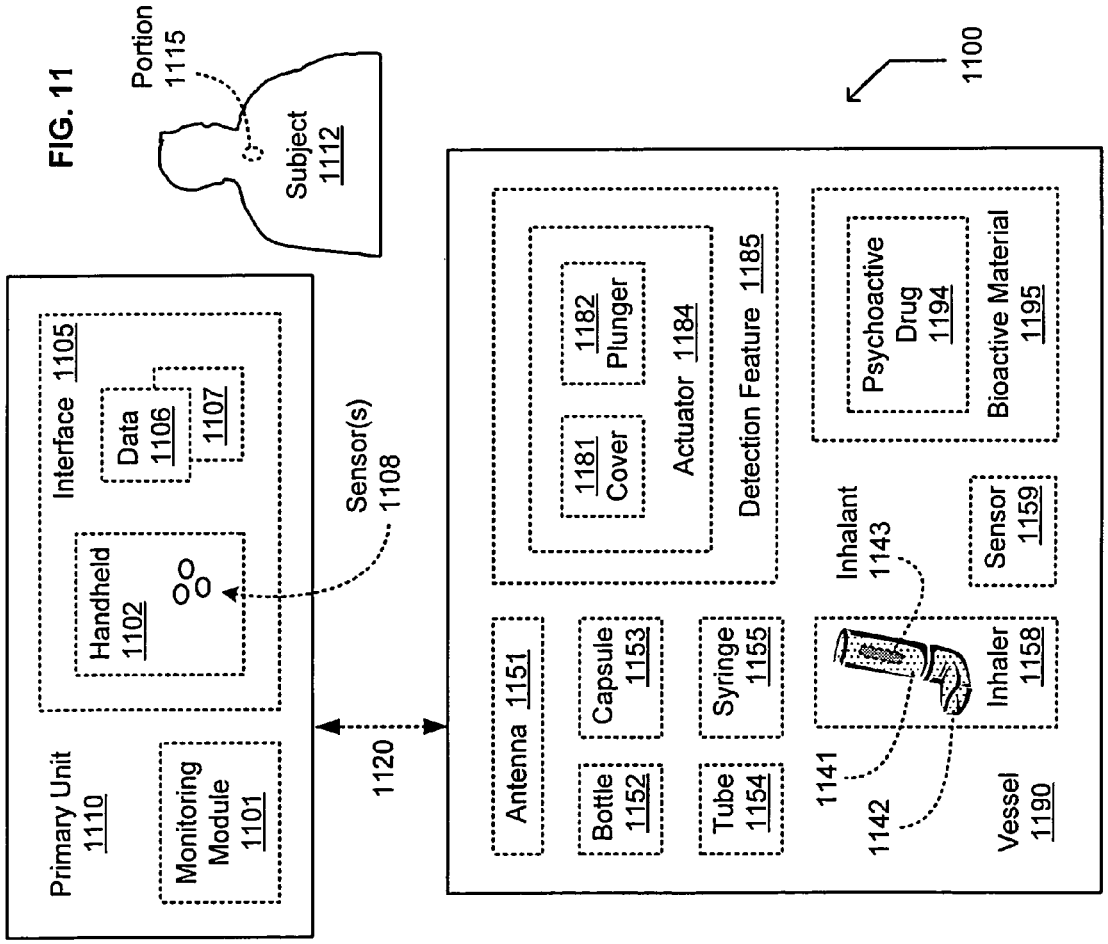
FIG. 11 depicts an exemplary environment featuring a vessel operable for dispensing a material.

With reference now to FIG. 11, shown is a system 1100 in which one or more technologies may be implemented in relation to a mouth, digestive tract, or other portion 1115 of interest in or on an individual 1112. In some contexts, such portions may be imaged, measured, or otherwise detected by one or more monitoring modules 1101 of a primary unit 1110. (handheld 1102 or other interface 1105, e.g.) configured to aggregate or distill data 1106, 1107 (via one or more sensors 1108, e.g.). Alternatively or additionally, such data (relating to regimen compliance, e.g.) can be obtained via one or more "smart" bottles 1152, capsules 1153, tubes 1154, syringes 1155, inhalers 1158, or other vessels 1190. In some variants, for example, such vessels may contain an inhalant 1143, psychoactive drug 1194, or other bioactive material 1195 or may include one or more covers 1181, plungers 1182, actuators 1184, color-coded portions, or other detection features 1185 (portions 1141, 1142 that move in relation to one another during an administration to a portion of a subject 1112, for example, such as may be detected by one or more sensors 1159, e.g.). In some contexts, moreover, actuation or other indications of movement (transmitted or received by antenna 1151 via wireless linkage 1120, e.g.) may signal an inhalation, ingestion, injection, expulsion, location, or other event relating to compliance as described herein (with reference to FIGS. 14-19, e.g.).

Figure 17:
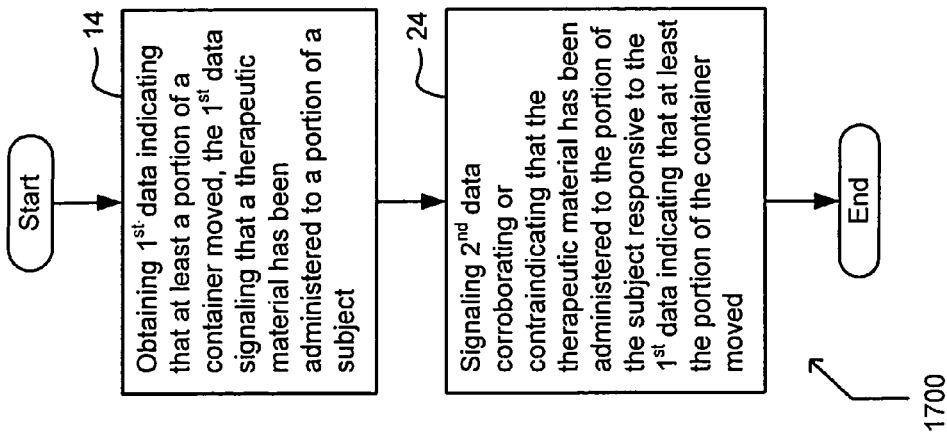
FIG. 17 depicts a high-level logic flow of an operational process described with reference to FIG. 11.

With reference now to FIG. 17, shown is a high-level logic flow 1700 of an operational process. Operation 14 describes obtaining first data indicating that at least a portion of a container moved, the first data signaling that a therapeutic material has been administered to a portion of a subject (e.g. monitoring module 1101 transmitting data 1106 selectively in response to receiving via antenna 1151 a device-detectable manifestation of movement of a cover 1181 or other actuator 1184 configured to dispense a psychoactive drug 1194 into or onto one or more human subjects 1112). This can occur, for example, in a context in which an actuation detection feature 1185 is configured to facilitate such movement detection via one or more sensors 1108, 1159 (detecting a movement of actuator 1184 or of an entirety of vessel 1190, e.g.), in which an optical or other wireless signal 1034 passing via linkage 1120 includes such "first" data, and in which primary unit 1110 implements an interaction unit 375, distillation unit 490, or other data handling units as described herein. Alternatively or additionally, such "first" data may comprise a dispenser control signal (from switch 145 or input device 178, e.g.) or other signal indicative of prior or concurrent physical dispensation into or onto one or more subjects 382, 1112. In a context in which interaction unit 375 implements a dispenser (inhaler 1158, e.g.) or other vessel 160, 1190 handled by a subject 1112, for example, monitoring module 1101 may receive any of several indications 574, 575 of a dispensation as "first" data 1106 indicating that bioactive material 1195 is being physically dispensed. Likewise component 214 may (optionally) include device-executable code 102 configured to permit one or more processors 115, 295 or application-specific circuitry to perform variants of operation 14 as described herein.

In light of teachings herein, numerous existing techniques may be applied for configuring special-purpose circuitry or other structures effective for generating and otherwise obtaining data indicating that some or all of a container moved as described herein without undue experimentation. See, e.g., U.S. Pat. No. 6,049,281 ("Method and apparatus for monitoring movements of an individual"); U.S. Pat. No. 7,715,277 ("Interactive medication container"); U.S. Pat. No. 7,331,340 ("Medicament dispensing device with a display indicative of the state of an internal medicament reservoir"); U.S. Pat. No. 7,837,648 ("Medicament dispensing system"); U.S. Pat. No. 6,085,752 ("Method, apparatus and operating system for managing the administration of medication and medical treatment regimens"); U.S. Pat. No. 6,723,086 ("Remote controlled transdermal medication delivery device"); U.S. Pat. No. 6,656,159 ("Dispenser for patient infusion device"); U.S. Pat. No. 5,694,919 ("Lockout device for controlled release of drug from patient-activated dispenser"); U.S. Pat. No. 7,852,217 ("Object detecting device, object detecting method and object detecting computer program"); U.S. Pat. No. 7,049,960 ("Method and system for locating objects"); U.S. Pat. No. 7,957,984 ("Device for facilitating compliance with medication regimen"); U.S. Pat. No. 7,343,943 ("Medication dose underfill detection system and application in an automated syringe preparing system"); U.S. Pat. No. 6,126,600 ("Ultrasound image assisted administering of medication"); U.S. Pat. No. 7,918,435 ("Combination gravimetric and volumetric dispenser for multiple fluids").

Operation 24 describes signaling second data corroborating or contraindicating that the therapeutic material has been administered to the portion of the subject responsive to the first data indicating that at least the portion of the container moved (e.g. interface 1105 requesting and recording, responsive to data 1106 from monitoring module 1101 manifesting a recognition of an actuator movement or other detection feature 1185, a verbal assurance or other "second" data 1107 from subject 1112 confirming such physical administration). This can occur, for example, in a context in which a bottle 1152, capsule 1153, or other vessel 1190 is configured to contain a bioactive material 1195 or other therapeutic product 150, in which the portion 1115 of the subject 1112 comprises the subject's throat, in which the "second" data does or does not include a specific reference to the throat, in which service provider 310 has configured interface 1105 to request verbal confirmation within a minute after monitoring module 1101 recognizes "first" data 1106, in which interface 1105 plays an audible query of "has the 2:00 medication been administered?" as a prompt and records a five-second sound clip afterward representative of a response (from a care provider 383 or other individual in the subject's environment, e.g.), and in which a series of such recordings (as raw data or otherwise) manifests a record of regimen compliance. Alternatively or additionally, interface 1105 may take such action responsive to "first" data signaling a relative movement of portions 1141, 1142 indicating that an inhalant 1143 or other drug may have been administered to a throat or other portion 1115 of subject 1112. In some variants, moreover, additional optical or other sensors 1108 in the subject's vicinity may take images (before and after, e.g.) or other "second" data as described herein. This can occur, for example, in a context in which a prior measurement 553 and current measurement 554 (of blood pressure, e.g.) before and after a putative administration (of a vasodilator, e.g.) is probative of whether the administration was actual, such as by storing the measurements or a comparison of the measurements in summary data 446. Alternatively or additionally, component 224 may include an instance of device-executable code 103 configured to permit one or more processors 115, 295 or application-specific circuitry to perform variants of operation 24 as described herein. In some variants, for example, a webcam or other monitoring unit 1101 (oriented to capture one or more images of a bathroom or other region in which one or more subjects may self-administer a medication, e.g.) may begin taking a video clip or other such images in response to a bottle 1152 or other vessel 1190 that has been configured to transmit a characteristic frequency or other recognizable wireless signal attribute (a characteristic "squawk" or "chirp" or digital sequence, e.g.) when an actuation or other sign of administration occurs.

In light of teachings herein, numerous existing techniques may be applied for configuring special-purpose circuitry or other structures effective for signaling that therapeutic material has been administered into or onto a subject responsive to a detection event as described herein without undue experimentation. See, e.g., U.S. Pat. No. 7,316,331 ("Solenoid using color-coded visual indicia in a liquid dispensing system"); U.S. Pat. No. 6,997,920 ("External infusion device with remote programming, bolus estimator and/or vibration alarm capabilities"); U.S. Pat. No. 7,942,916 ("Phototreatment device for use with coolants and topical substances"); U.S. Pat. No. 7,733,224 ("Mesh network personal emergency response appliance"); U.S. Pat. No. 7,905,230 ("Metered dose inhaler with lockout"); U.S. Pat. No. 6,971,383 ("Dry powder inhaler devices, multi-dose dry powder drug packages, control systems, and associated methods"); U.S. Pat. No. 7,981,102 ("Removable controller for an infusion pump"); U.S. Pat. No. 7,963,946 ("Method and system for controlled infusion of therapeutic substances"); U.S. Pat. No. 7,937,461 ("Method for controlling a daily living activity monitoring system from a remote location"); U.S. Pat. No. 7,918,843 ("Controllable drug delivery device"); U.S. Pat. No. 7,914,483 ("Pain controlled analgesic ("PCA") apparatus").

Some instances of flow 1700 may (optionally) be performed by one or more servers 294 that are remote from primary system 200 but operable to cause output device(s) 276 to receive and to present or cause results via linkage 250. Alternatively or additionally, device-detectable data 238 may be borne by one or more instances of integrated circuits 274, signal-bearing conduits 286, holding devices 289, or the like as described herein. Such data may optionally be configured for transmission (in operation 24, e.g.) by a semiconductor chip or other embodiment of integrated circuit 274 that contains or is otherwise operatively coupled with antenna 275 (in a radio-frequency identification tag, for example).

In some variants, flow 1700 may be implemented entirely within primary system 200. Operation 14 may (optionally) be implemented by configuring component 214 as logic for obtaining first data indicating that at least a portion of a container moved, the first data signaling that a therapeutic material has been administered to a portion of a subject, for example, such as by including special-purpose instruction sequences or special-purpose-circuit designs for this function. Output data 237 from component 214 in primary system 200 or network 290 may be recorded into available portions of storage device(s) 287 or sent to component 224, for example. Component 224 may likewise perform operation 24 via implementation as logic for signaling second data corroborating or contraindicating that the therapeutic material has been administered to the portion of the subject responsive to the first data indicating that at least the portion of the container moved, for example. Implementation output data 238 from such a component in primary system 200 or network 290 may be recorded into available portions of storage device(s) 287 or sent to processor 295, for example. Each portion of implementation 204 may likewise include one or more instances of software, hardware, or the like implementing logic that may be expressed in several respective forms as described herein or otherwise understood by those skilled in the art.

With reference now to FIG. 12, shown is a system 1200 in which one or more technologies may be implemented by which one or more vessels 1210 having one or more antennas 1250 may establish a linkage 1255 to or with an application module 110 or other device 1280 in a vicinity of one or more subjects 382, 1282. In some contexts, such devices may include one or more decision modules 1270 configured to implement one or more decisions 1273 to enable or otherwise cause an actuation of one or more motors 133 or other mechanical components 1275, 1276 in response to a detection or other wireless signal 1230 from a vessel 1210 ingested by or implanted into a human or other subject 1282. One or more logic modules 1222 or other control modules 1220 may manifest such detections or decisions as or from indicia 1224 from one or more mucosal material sensors 1221; pH sensors 1225 or other chemical sensors 1226; or other sensors 1228, 1229 and sensor logic 1227 as described herein. Alternatively or additionally, control module 1220 may respond to measurements or other indicia 1224 (timing data 537, 538, 539 or biometric data 536, e.g.) by dispensing one or more anti-infective materials 1237 or other bioactive materials 1240 (administering material components 534 to a portion of a subject 382, e.g.). Alternatively or additionally, device 1280 may include one or more media 550 or data handling units 610 as described herein.

With reference now to FIG. 18, shown is a high-level logic flow 1800 of an operational process. Operation 15 describes obtaining an indication whether a vessel has been ingested by a subject (e.g. logic module 1222 and a mucosal material sensor 1221, temperature sensor, or other sensor 1229 jointly generating one or more measurements or other indicia 1224 that vessel 1210 has been ingested by a human subject 382, 1112, 1282). This can occur in a context in which a vessel 1210 that includes such components is configured to be ingestible by a human or other subject 1282 and, for example, to dispense an anti-infective material 1237 or other bioactive material 1240. In some variants, vessel 1210 may include an acid-soluble coating or other barrier 1018 as described herein. For example, such barriers may include a therapeutic or other bioactive material 1240 configured to corroborate the vessel having been ingested (by being configured to melt below, but within 0 to 10 degrees centigrade of, a nominal body temperature of a mammal as the subject, for example, or to dissolve by a chemical reaction with digestive fluids). Alternatively or additionally, component 215 may include device-executable code 102 configured to permit one or more processors 115, 295 or application-specific circuitry to perform variants of operation 15 as described herein.

Operation 25 describes signaling a decision whether to actuate a mechanical component outside the subject responsive to the indication whether the vessel has been ingested by the subject (e.g. control module 1220 responding to the one or more such indicia 1224 by transmitting a wireless signal 1230 directing an electromechanical device 1280 to move one or more mechanical components 1275). This can occur, for example, in a context in which control module 1220 transmits such decision 1273 via antenna 1250 to a decision module 1270 configured to trigger an actuator 1184 or other mechanical component 1275 accessible to a subject 382, 1282 (implemented in interaction unit 375, e.g.). Alternatively or additionally, decision module 1270 may respond to one or more such decisions 1273 by disabling one or more locks 132 or otherwise by causing one or more mechanical components 1276 not to move (selectively) in response to a wireless signal 1230 or other device-detectable indication that vessel 1210 has been ingested. Alternatively or additionally, component 225 may include an instance of device-executable code 103 configured to permit one or more processors 115, 295 or application-specific circuitry to perform variants of operation 25 as described herein.

In light of teachings herein, numerous existing techniques may be applied for configuring special-purpose circuitry or other structures effective for deciding whether to actuate a mechanical component as described herein without undue experimentation. See, e.g., U.S. Pat. No. 7,988,627 ("Biometric network exchange system"); U.S. Pat. No. 7,986,220 ("Automatic door system"); U.S. Pat. No. 7,984,853 ("Reducing internal theft at a point of sale"); U.S. Pat. No. 7,861,676 ("Training guidance system for canines, felines, or other animals"); U.S. Pat. No. 7,667,609 ("Expert system rescue of impaired equipment operators"); U.S. Pat. No. 7,620,817 ("System for security checking or transport of persons by an elevator installation and a method for operating this system"); U.S. Pat. No. 7,584,033 ("Automobile monitoring for operation analysis"); U.S. Pat. No. 7,451,852 ("Vehicle sobriety interlock system with personal identification element"); U.S. Pat. No. 7,327,231 ("Failsafe disable in a vehicle security system"); U.S. Pat. No. 6,985,779 ("Monitoring system for an industrial process using one or more multidimensional variables"); U.S. Pat. No. 6,102,246 ("Automated beverage system").

Some instances of flow 1800 may (optionally) be performed by one or more servers 294 that are remote from primary system 200 but operable to cause output device(s) 276 to receive and to present or cause results via linkage 250. Alternatively or additionally, device-detectable data 240 may be borne by one or more instances of integrated circuits 274, signal-bearing conduits 286, holding devices 289, or the like as described herein. Such data may optionally be configured for transmission (in operation 25, e.g.) by a semiconductor chip or other embodiment of integrated circuit 274 that contains or is otherwise operatively coupled with antenna 275 (in a radio-frequency identification tag, for example).

In some variants, flow 1800 may be implemented entirely within primary system 200. Operation 15 may (optionally) be implemented by configuring component 215 as logic for obtaining an indication whether a vessel has been ingested by a subject, for example, such as by including special-purpose instruction sequences or special-purpose-circuit designs for this function. Output data 239 from component 215 in primary system 200 or network 290 may be recorded into available portions of storage device(s) 287 or sent to component 225, for example. Component 225 may likewise perform operation 25 via implementation as logic for signaling a decision whether to actuate a mechanical component outside the subject responsive to the indication whether the vessel has been ingested by the subject, for example. Implementation output data 240 from such a component in primary system 200 or network 290 may be recorded into available portions of storage device(s) 287 or sent to processor 295, for example. Each portion of implementation 205 may likewise include one or more instances of software, hardware, or the like implementing logic that may be expressed in several respective forms as described herein or otherwise understood by those skilled in the art.

With reference now to FIG. 13, shown is a system 1300 in which one or more technologies may be implemented to respond to one or more signals 1365 received (via wireless receiver 1370, e.g.) from a capsule or other unit in a region 1330 of interest (a module 162 or other device in a portion or vicinity of a subject or in a detection region defined by an energy sensor, e.g.). See FIG. 23. This can occur, for example, in a context in which such a vessel 490 (implant 1340, e.g.) transmits a signal 1365 (originating in one or more sensors 1342, e.g.) along a wireless signal path 1345 (through skin 1326 or other tissue 1320, e.g.) into a handheld instrument 1350 or other detection module 1380. Alternatively or additionally, detection module 1380 may include one or more instances of decision modules 1394, reporting modules 1397, or acquisition modules 1360 (including one or more ultrasound imaging modules 1361 or other imaging modules 1362 configured to capture images 1364 selectively as described herein, e.g.). Moreover interface 270 may implement a similar detection module having one or more charge-coupled devices, lenses 271, or other input devices 278 (configured to perform selective image capture and optionally coupled with one or more image data distillation modules 434 as described herein, e.g.).

With reference now to FIG. 19, shown is a high-level logic flow 1900 of an operational process. Operation 16 describes deciding whether to obtain one or more images of a region responsively to whether a wireless signal has been received from a device in the region (e.g. decision module 1394 deciding whether to trigger acquisition module 1360 of instrument 1350 to capture one or more images 631 in response to wireless receiver 1370 receiving a wireless signal 1034, 1365 from vessel 1010 or implant 1340). This can occur, for example, in a context in which such triggering occurs quickly enough (within a few milliseconds, e.g.) so that a handheld instrument 1350 will still be positioned effectively to permit the region 1330 of interest (containing the device, e.g.) to be imaged. In some variants, for example, one or both of application module 110 and product 150 may perform such triggered acquisition of images 1364 (and biometric data 536 or other compliance status indications 573-575 as well, e.g.) contemporaneously in response to detecting the other. Alternatively or additionally, component 216 may include device-executable code 102 configured to permit one or more processors 115, 295 or application-specific circuitry to perform variants of operation 16 (responsive to one or more sensors 179, 833, e.g.) as described herein.

In light of teachings herein, numerous existing techniques may be applied for configuring special-purpose circuitry or other structures effective for receiving and recognizing particular wireless signals or attributes from a proximal device in a region of interest as described herein without undue experimentation. See, e.g., U.S. Pat. No. 6,581,036 ("Secure remote voice activation system using a password"); U.S. Pat. No. 7,961,936 ("Non-overlap region based automatic global alignment for ring camera image mosaic"); U.S. Pat. No. 7,830,417 ("System and method for interacting with objects via a camera enhanced mobile device"); U.S. Pat. No. 7,949, 150 ("Automatic camera calibration and geo-registration using objects that provide positional information"); U.S. Pat. No. 7,796,162 ("Providing multiple synchronized camera views for broadcast from a live venue activity to remote viewers"); U.S. Pat. No. 6,819,867 ("Hand-held remote control and display system for film and video cameras and lenses"); U.S. Pat. No. 7,330,742 ("Portable communication device and method of sensing camera operation mode in the portable communication device"); U.S. Pat. No. 7,898,570 ("Digital camera system with means for restricting image acquisition"); U.S. Pat. No. 7,792,364 ("Image processing apparatus and image processing program product for discriminating dot region in image"); U.S. Pat. No. 7,636,470 ("Red-eye detection based on red region detection with eye confirmation"); U.S. Pat. No. 7,613,426 ("Proximity service discovery in wireless networks"); U.S. Pat. No. 7,780,590 ("Method for locating an implanted fluid access port").

Operation 26 describes signaling a data distillation indicative of a regimen compliance status responsively to whether the wireless signal has been received from the device in the region (e.g. reporting module 1397 conditionally transmitting a regimen noncompliance determination 688 responsive to an absence of compliance-indicative data within the wireless signal, or to a failure to receive the wireless signal within a prescribed duration specified by one or more thresholds 563 or other data distillation criteria 625). This can occur, for example, in a context in which an expert service provider 310 requires a care provider 383 or prison guard to perform a periodic scanning of the region (scanning a part of the subject's body via a handheld instrument 1350 or stationary monitor 850, e.g.); in which data handling unit 610 is configured to detect the wireless signal via one or more detection modules 870, 1380; and in which an output (reporting module 1397, e.g.) transmits confirmatory data, such as an image 1364 of region 1330 or other scan results, as a manifestation of compliance. Alternatively, in some variants, reporting module 1397 may be configured to transmit a negative indication 689 (as the data distillation of operation 26, indicating a negative regiment compliance status) in the absence of compliance-indicative data 652 and otherwise to transmit nothing (manifesting a regimen compliance determination 686 or other positive indication 687, e.g.). Alternatively or additionally, component 226 may include an instance of device-executable code 103 configured to permit one or more processors 115, 295 or application-specific circuitry to perform variants of operation 26 as described herein.

In some contexts, control modules may jointly perform operation 26 by indicating "currently compliant" or some other compliance-positive indication 687 responsively to a recognizable wireless signal being or having been received from an implanted or ingested vessel 160, 1010, 1210 or other peripheral unit 190 in a region of interest. This can occur, for example, in a context in which the bowl 830 of commode 810 of FIG. 8 bounds the region of interest, in which commode 810 supports or includes a monitor unit 850 having one or more sensors 833 or other features oriented toward or positioned in bowl 830, in which detection module 870 has recognized data 863 from an ingestible capsule or other device 860 in the region, and in which logic module 875 and control module 880 are jointly configured to perform operation 26 responsively to such recognition (as an instance of operation 16, e.g.). Alternatively or additionally, component 226 may include device-executable code 103 configured to permit one or more processors 115, 295 or application-specific circuitry to perform variants of operation 26.

Some instances of flow 1900 may (optionally) be performed by one or more servers 294 that are remote from primary system 200 but operable to cause output device(s) 276 to receive and to present or cause results via linkage 250. Alternatively or additionally, device-detectable data 242 may be borne by one or more instances of integrated circuits 274, signal-bearing conduits 286, holding devices 289, or the like as described herein. Such data may optionally be configured for transmission (in operation 26, e.g.) by a semiconductor chip or other embodiment of integrated circuit 274 that contains or is otherwise operatively coupled with antenna 275 (in a radio-frequency identification tag, for example).

In some variants, flow 1900 may be implemented entirely within primary system 200. Operation 16 may (optionally) be implemented by configuring component 216 as logic for deciding whether to obtain one or more images of a region responsively to whether a wireless signal has been received from a device in the region, for example, such as by including special-purpose instruction sequences or special-purpose-circuit designs for this function. Output data 241 from component 216 in primary system 200 or network 290 may be recorded into available portions of storage device(s) 287 or sent to component 226, for example. Component 226 may likewise perform operation 26 via implementation as logic for signaling a data distillation indicative of a regimen compliance status responsively to whether the wireless signal has been received from the device in the region, for example. Implementation output data 242 from such a component in primary system 200 or network 290 may be recorded into available portions of storage device(s) 287 or sent to processor 295, for example. Each portion of implementation 206 may likewise include one or more instances of software, hardware, or the like implementing logic that may be expressed in several respective forms as described herein or otherwise understood by those skilled in the art.

Figure 20:
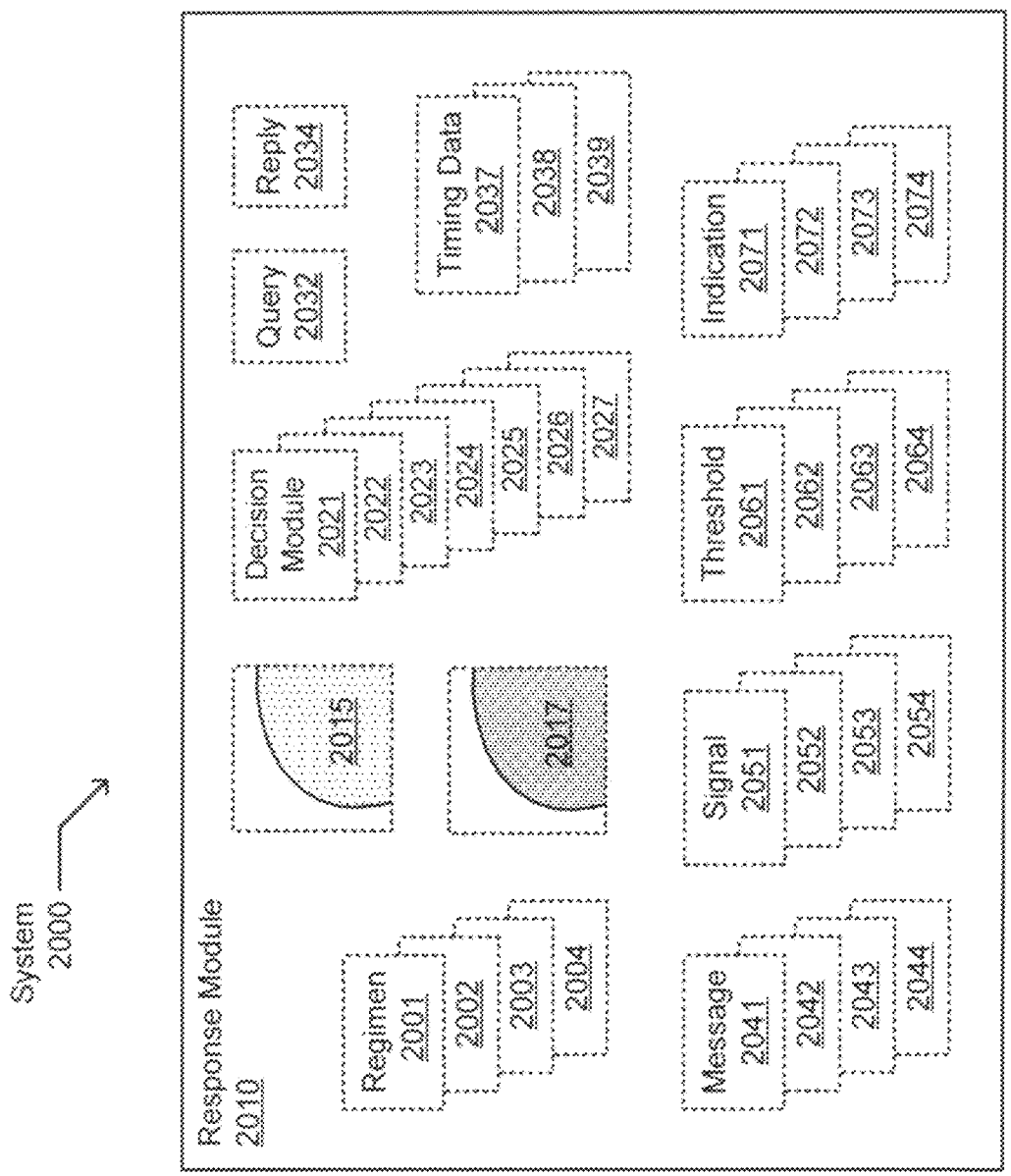
FIG. 20 depicts an exemplary environment featuring a response module.

With reference now to FIG. 20, shown is a system 2000 in which one or more technologies may be implemented. In various configurations, response module 2010 may implement (as application-specific data sets on one or more media 550 or in code 101-104 executable by one or more processors 115, 295, e.g.) one or more regimens 2001, 2002, 2003, 2004; decision modules 2021, 2022, 2023, 2024, 2025, 2026, 2027; timing data 2037, 2038, 2039; queries 2032, replies 2034, and other messages 2041, 2042, 2043, 2044 or signals 2051, 2052, 2053, 2054. Alternatively or additionally, one or more instances of response module 2010 (in an ingestible vessel 160 or other peripheral unit 190, e.g.) may likewise include one or more sensors 187, 833, 917, 932 or other detection components 796 configured to signal one or more measurements 664-667 or other detected events; to apply one or more thresholds 2061, 2062, 2063, 2064 or other criteria; or otherwise to generate one or more pointers 676-679 or other indications 2071, 2072, 2073, 2074 in relation to one or more clips 641-644, samples 2015, 2017, or regimens as described herein.

Figure 21:
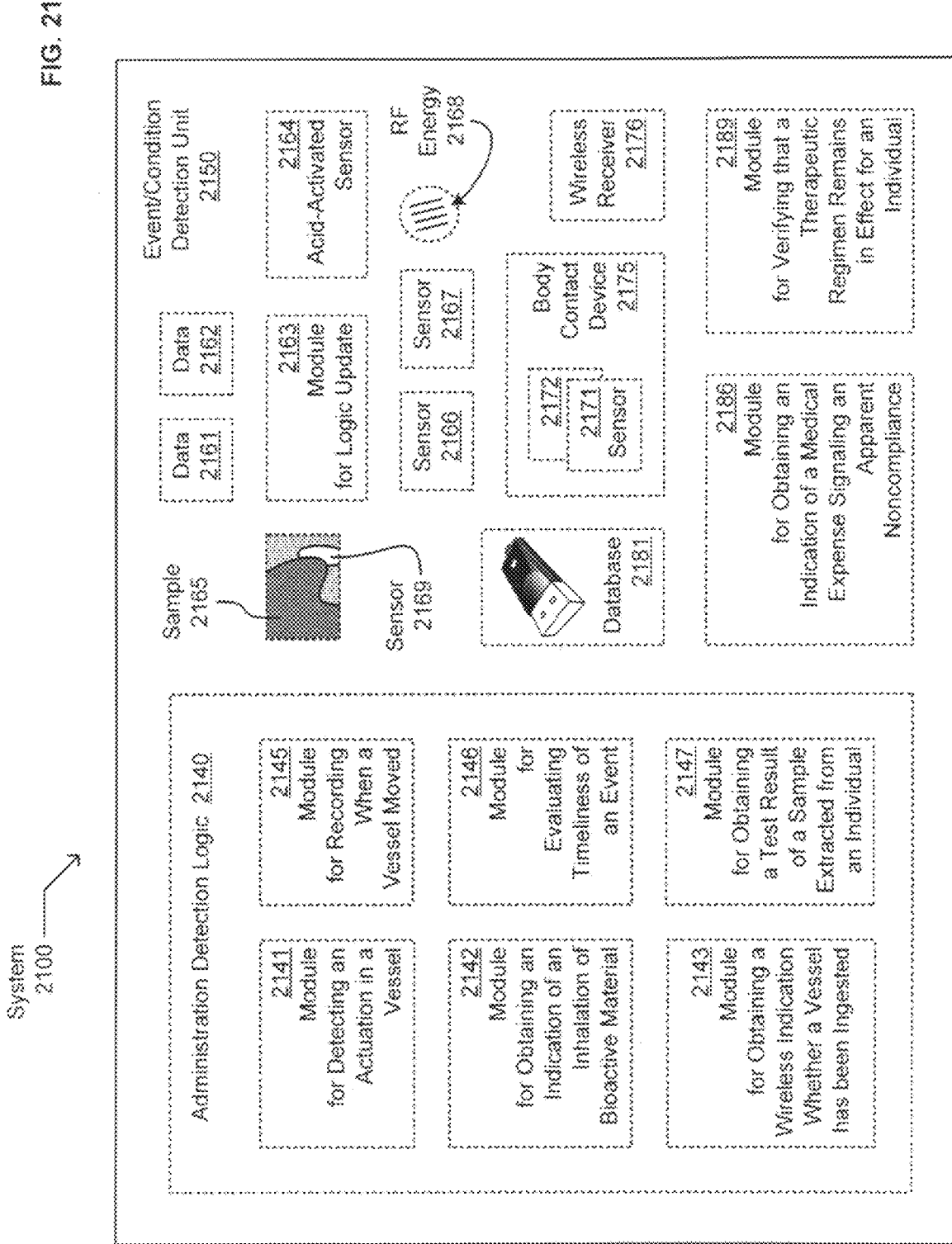
FIG. 21 depicts an exemplary environment featuring an event/condition detection unit.

With reference now to FIG. 21, shown is a system 2100 in which one or more technologies may be implemented. Event/condition detection unit 2150 may include one or more acid-activated sensors 2164; sensors 2166, 2167 for detecting RF energy 2168, vocalizations, or other such energy phenomena; sensors 2169 configured to detect optical or other attributes of a sample 2165; sensors 2171, 2172 (on or near skin 1326 or other tissue 1320 in situ, e.g.) supported by a patch, garment, or other body contact device 2175; or other sensors 179, 187, 1011-1013 or detection structures as described herein. In some variants, for example, event/condition detection unit 2150 may include administration detection logic 2140 or a wireless receiver 2176 configured to respond to raw data 410, event indications 440 or other data distillations 450, or other data 530, 2161, 2162 (in database 2181, e.g.) as described herein. Alternatively or additionally, event/condition detection unit 2150 may include one or more instances of modules for obtaining an indication of a medical expense signaling an apparent noncompliance 2186, modules for verifying that a therapeutic regimen remains in effect for an individual 2189, or modules for logic updates 2163 (as a software configuration or circuitry invocation, e.g.) as described herein. In some variants, moreover, administration detection logic 2140 may include one or more instances of modules for detecting an actuation in a vessel 2141, modules for obtaining an indication of an inhalation of bioactive material 2142, modules for obtaining a wireless indication whether a vessel has been ingested 2143, modules for recording when a vessel moved 2145, modules for evaluating timeliness of an event 2146 (an administration or apparent presence of a device at a toilet, e.g.); or modules for obtaining a test result of a sample extracted from an individual 2147.

Figure 22:
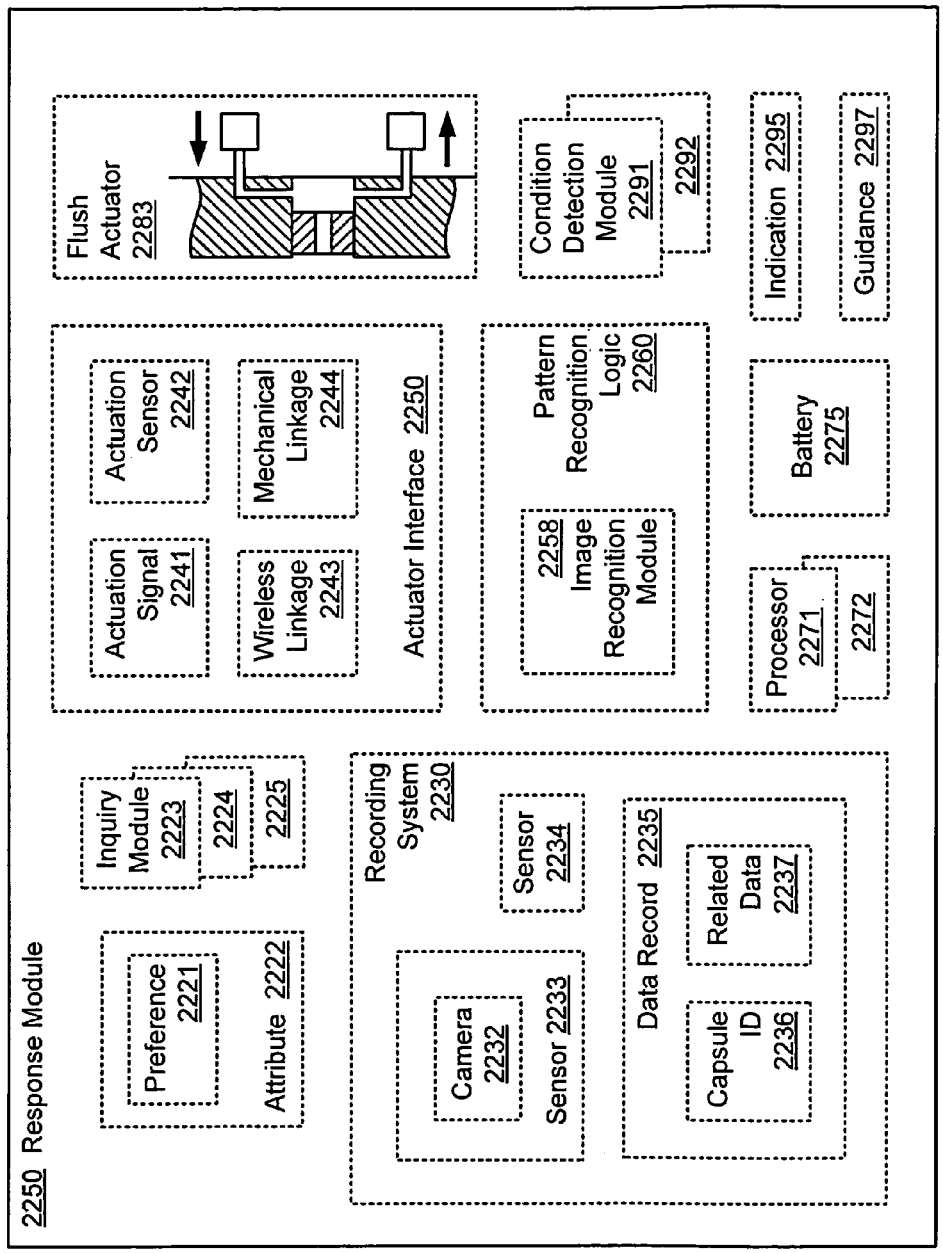
FIG. 22 depicts an exemplary environment featuring a response module.

With reference now to FIG. 22, shown is a system 2200 in which one or more technologies may be implemented. As explained below, one or more event/condition detection units 2150 or other response modules 2010, 2250 may include one or more inquiry modules 2223, 2224, 2225; actuator interfaces 2250 configured to respond to an input device 178 (keypad, microphone, button 835, or lever, e.g.) or to control or respond to a mechanical component 130 (flush actuator 2283, e.g.) via a wireless linkage 2243 or a mechanical linkage 2244; recording systems 2230; image recognition modules 2258 or other pattern recognition logic 2260 or condition detection modules 2291, 2292. In some configurations, one or more processors 2271, 2272 may generate guidance 2297 (instructions 478 to a technician 361 or other consultant, e.g.) or implement such control or other response configurations in response to a device state 173 (of a micro-battery 182 or other battery 2275, e.g.) or to one or more preferences 2221, demographic attributes 750 or other determinants 760, or other attributes 2222 of a subject 382. Alternatively or additionally, such response may depend upon one or more of actuation signals 2241 (manifesting an actuation command or signal from an actuation sensor 2242, e.g.); image data 424 or other raw data 410 (from one or more cameras 2232 or other sensors 2233, 2234, e.g); or components from a data record 2235 (a capsule identifier 2236 with dosages or material components 534 or sensor specifications or other related data 2237 indicative of a product 150, e.g.) or other indications 2295 as described herein.

With reference now to FIG. 23, shown is a frequency domain energy distribution 2300 in which a received signal 2330 (from a wireless receiver as described herein, e.g.) is plotted on a linear vertical axis 2301 representative of amplitude and a logarithmic horizontal axis 2302 representative of frequency. Signal 2330 has peaks 2351, 2352 at respective particular nominal frequencies interspersed among several reference frequencies 2361, 2362, 2363, 2364 bounding frequency ranges 2371, 2372, 2373, 2374, 2377, 2378 as shown. As shown reference amplitude 2342 is intermediate in magnitude, smaller than the amplitude 2341 of the highest peak 2351 of signal 2330 but larger than the amplitude 2343 of smaller peak 2352.

Figure 24:
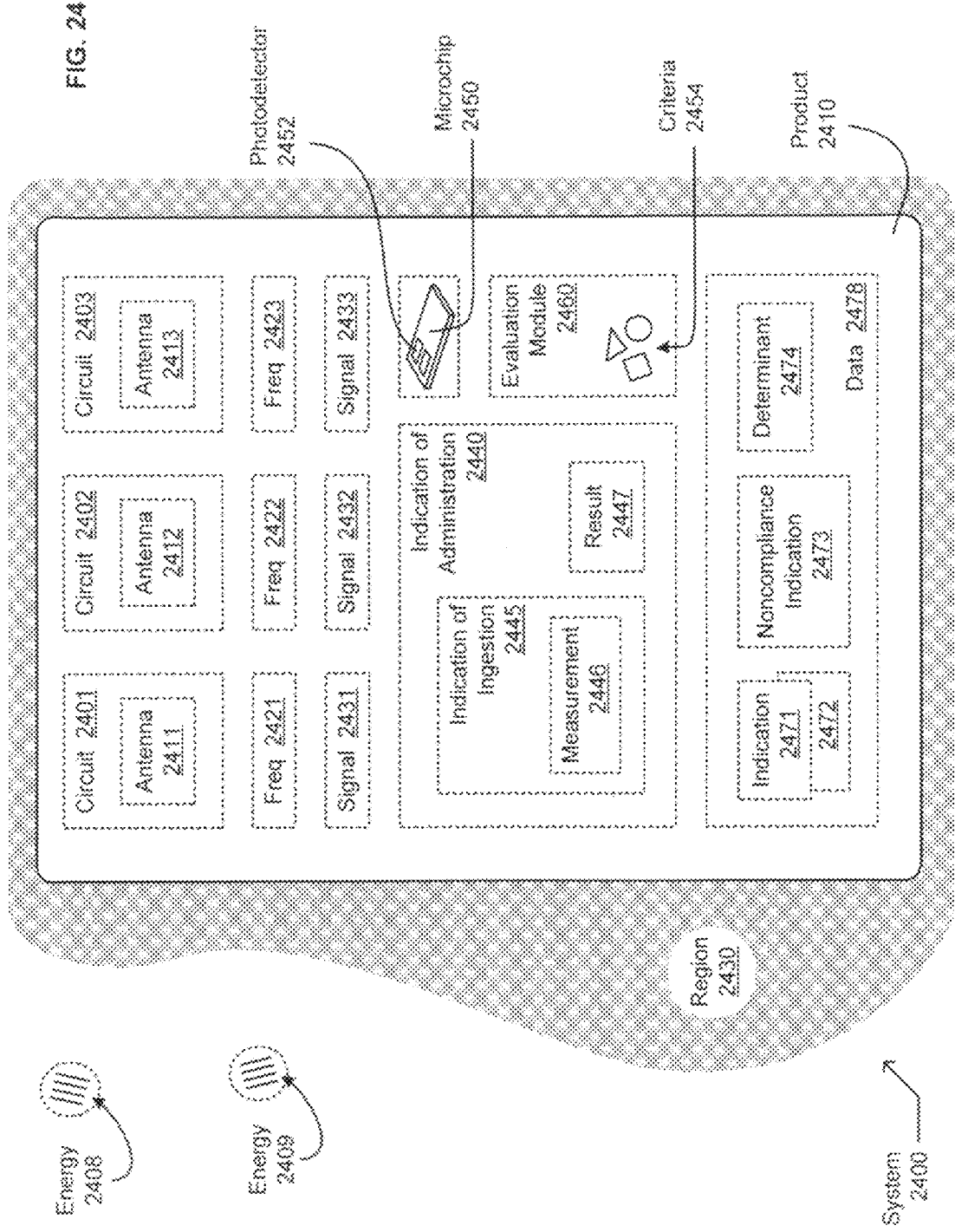
FIG. 24 depicts an exemplary environment featuring a device-detectable product in a region of interest.

With reference now to FIG. 24, shown is a system 2400 in which one or more technologies may be implemented. In some contexts a product 2410 (e.g. a single ingestible capsule 491) may contain two or more circuits 2401, 2402 each configured to respond to incoming energy 2408 at respective nominal resonance frequencies 2421, 2422 that differ by at least 10-50%, or optionally by one or more orders of magnitude. In some contexts an antenna 2411 that resonates (at least) at a "lower" frequency 2421 can be configured to detect whether incident energy 2408 contains a wireless signal 2431 that successfully passes through region 2430, for example, and an antenna 2412 that resonates (at least) at a "higher" frequency 2422 can be configured to detect whether incident energy 2408 contains a wireless signal 2432 that successfully passes through region 2430. In such contexts, evaluation module 2460 can be configured to use the simultaneous presence of both wireless signal 2431 and wireless signal 2432 as a noncompliance indication 2473 (a regimen noncompliance determination 688 or other compliance-negative indication 689, e.g.) to be transmitted or recorded. Alternatively or additionally, evaluation module 2460 can be configured to generate a compliance-positive indication 687 (indicative of compliance with a regimen of capsule ingestion, e.g.) in response to circuit 2401 receiving a lower-frequency wireless signal 2431 during a period (of several minutes or hours, e.g.) in which circuit 2401 does not receive a higher-frequency wireless signal (as determinant 2474, e.g.).

In light of teachings herein, numerous existing techniques may be applied for configuring special-purpose circuitry or other structures effective for receiving energy at selected frequencies and for determining whether such energy contains a signal to implement regimen-specific or other criteria 2454 as described herein without undue experimentation. See, e.g., U.S. Pat. No. 7,463,700 ("Code division multiple access wireless system with closed loop mode using ninety degree phase rotation and beamformer verification"); U.S. Pat. No. 7,203,245 ("Symbol boundary detector method and device for OFDM systems"); U.S. Pat. No. 7,983,305 ("Apparatus and method for transmitting and receiving wireless packet data"); U.S. Pat. No. 7,956,734 ("Wireless tag reader/writer apparatus"); U.S. Pat. No. 7,965,798 ("Robust packet detection, symbol timing, channel length estimation and channel response estimation for wireless systems"); U.S. Pat. No. 7,936,713 ("Hierarchical data collection network supporting packetized voice communications among wireless terminals and telephones"); U.S. Pat. No. 7,835,319 ("System and method for identifying wireless devices using pulse fingerprinting and sequence analysis"); U.S. Pat. No. 7,839,153 ("Communicating with an implanted wireless sensor"); U.S. Pat. No. 7,713,200 ("Wireless beacon for time-reversal acoustics, method of use and instrument containing thereof"); U.S. Pat. No. 7,944,886 ("Infrastructure-based enabling indication for dynamic frequency selection in wireless networks"); U.S. Pat. No. 7,294,105 ("System and method for a wireless medical communication system"); U.S. Pat. No. 7,844,687 ("Method for internetworked hybrid wireless integrated network sensors (WINS)").

In some variants, a single ingestible capsule 910, 1153 (product 2410, e.g.) may contain two or more circuits 2402, 2403 each configured to transmit energy 2409 at respective nominal resonance frequencies 2422, 2423 that differ by at least 10-50%, or optionally by one or more orders of magnitude. In some contexts an antenna 2412 that resonates (at least) at a "lower" frequency 2422 can be configured to enable one or more decision modules 2027 to determine whether such energy 921, 2409 contains a wireless signal 2432 that successfully passes through region 2430, for example, and an antenna 2413 that resonates (at least) at a "higher" frequency 2423 can be configured to enable one or more decision modules 2027 to determine whether such energy 921, 2409 contains a wireless signal 2433 that successfully passes through region 2430. In some variants, for example, one or more such circuitries 2401-2403 may each be configured as a passive wireless transponder 492, for example, or active logic powered by a micro-battery 182 or by other suitable configurations: see, e.g., U.S. Pat. No. 5,338,625 ("Thin film battery and method for making same") and U.S. Pub. No. 2005/0143787 ("Method and system for providing electrical pulses for neuromodulation of vagus nerve(s), using rechargeable implanted pulse generator"). Alternatively or additionally, one or more circuits 2401, 2402 configured to receive energy 2408 may be combined with one or more circuits 2403 configured to transmit energy 2409 in any combination that permits a determination of whether region 2430 selectively blocks energy 2408, 2409 containing a signal 2432, 2433 in a higher-frequency range (range 2374, e.g.). In some variants, product 2410 may be configured as a single microchip (in an ingestible capsule, e.g.) that contains two or more such antennas 2411-2413. This can occur, for example, in a context in which an opaque capsule 491 containing such a microchip is packaged (with a therapeutic component 181, e.g.) in a vessel 160 containing several look-alike capsules (resembling the "smart" capsules but not containing their same microchip, e.g.).

Alternatively or additionally, application module 110 may include one or more instances of code 101-104 executable by processor 115 as described herein to detect and act upon a region 2430 preferentially allowing passage of a lower-frequency signal, and blocking some or all energy in a higher-frequency signal, as an indication of ingestion 2445 or of implantation. Application module 110 may likewise be configured to invoke circuitry as described herein for transmitting energy 2408 (interrogation signal 141, e.g.) through a region 2430 of interest to a capsule or other object (device 860, e.g.) that may or may not contain specific wireless communication circuitry (circuits 2401-2403 as described above, e.g.). In some contexts a wireless reply signal 142 may be recognized as an indication that a specific device (product 2410, e.g.) is in a region 2430 of interest (in bowl 830, e.g.) if reply signal 142 has a characteristic frequency 2361, 2362 or other recognizable attribute (a digitally-encoded capsule identifier 2236, e.g.) specific to product 2410. In such contexts reply signal 142 may also include a regimen-negative indication 689 (if its energy distribution has one or more peaks 2352 larger than amplitude 2343 in a higher frequency range 2373, 2378, e.g.) or a regimen-positive indication 687 (if its energy distribution has no peaks larger than amplitude 2342 in a higher frequency range 2374, e.g.). In some variants the probative value of such indications may be enhanced by one or more thermal or pH measurements 2446 or images or other results 2447 as indications of administration 2440 of a therapeutic material or normalcy indications 2471, 2472 or other compliance-status-indicative data 2478 that can be distilled according to one or more criteria 623, 624 (various distilling operations described herein, e.g.). Alternatively or additionally, a microchip 2450 implementing product 2410 may be configured to include one or more light-emitting diodes or photodetectors 2452 for transmitting or detecting optical energy 2408, 2409 effectively to facilitate a frequency transmissivity characterization of region 2430 (by using infrared energy instead of or in addition to radio frequency energy, e.g.)

In some embodiments, output device 276 may indicate an occurrence of one or more flows of FIGS. 14-19 concisely as a decision, an evaluation, an effect, an hypothesis, a probability, a notification, or some other useful technical result. For example, such "indicating" may comprise such modes as showing, signifying, acknowledging, updating, explaining, associating, or the like in relation to any past or ongoing performance of such actions upon the common item(s) as recited. Such indicating may also provide one or more specifics about the occurrence: the parties or device(s) involved, a description of the method or performance modes used, any sequencing or other temporal aspects involved, indications of resources used, location(s) of the occurrence, implementation version indications or other update-indicative information, or any other such contextual information that may be worthwhile to provide at potential output destinations.

Concise indication may occur, for example, in a context in which at least some items of data 231-242 do not matter, or in which a recipient may understand or access portions of data 231-242 without receiving a preemptive explanation of how it was obtained. By distilling one or more outputs 251-256 at an "upstream" stage (which may comprise integrated circuit 274, for example, in some arrangements), downstream-stage media (such as other elements of network 290, for example) may indicate occurrences of various methods described herein more effectively. Variants of such flows, for example, may be enhanced by distillations described herein, especially in bandwidth-limited transmissions, security-encoded messages, long-distance transmissions, complex images, or compositions of matter bearing other such expressions.

In some variants, a local implementation comprises a service operable for accessing a remote system running a remote implementation. In some embodiments, such "accessing" may include one or more instances of establishing or permitting an interaction between the server and a local embodiment such that the local embodiment causes or uses another implementation or output of one or more herein-described functions at the server. Functioning as a web browser, remote terminal session, or other remote activation or control device, for example, interface(s) 270 may interact with one or more primary system users via input and output devices 276, 278 so as to manifest an implementation in primary system 200 via an interaction with server 294, for example, running a secondary implementation of one or more flows 1400, 1500, 1600, 1700, 1800, 1900. Such local implementations may comprise a visual display supporting a local internet service to the remote server, for example. Such a remote server may control or otherwise enable one or more instances of hardware or software operating the secondary implementation outside a system, network, or physical proximity of primary system 200. For a building implementing primary system 200, for example, "remote" devices may include those in other countries, in orbit, or in adjacent buildings. In some embodiments, "running an implementation" may include invoking one or more instances of software, hardware, firmware, or the like atypically constituted or adapted to facilitate methods or functions as described herein. For example, primary system 200 running an implementation of a flow described herein may be a remote activation of a special-purpose computer program resident on server 294 via an internet browser session interaction through linkage 250, mediated by input device 278 and output device 276.

In some variants, some or all of components 210-216 and 221-226 may be borne in various data-handling elements—e.g., in one or more instances of storage devices 287, in memories 288 or volatile media, passing through linkage 250 with network 290 or other conduits 286, in one or more registers or data-holding devices 289, or the like. For example, such processing or configuration may occur in response to user data or the like received at input device 278 or may be presented at output device 276. Instances of input devices 278 may (optionally) include one or more instances of cameras or other optical devices, hand-held systems or other portable systems, keypads, sensors, or the like as described herein. Output device(s) 276 may likewise include one or more instances of image projection modules, touch screens, wrist-wearable systems or the like adapted to be worn while in use, headphones and speakers, eyewear, liquid crystal displays (LCDs), actuators, lasers, organic or other light-emitting diodes, phosphorescent elements, portions of (hybrid) input devices 278, or the like.

A device-detectable implementation of variants described herein with reference to flows depicted in FIGS. 14-19, for example, may be divided into several components 210-216 and 221-226 carried by one or more instances of active modules such as signal repeaters 291, communication satellites 293, servers 294, processors 295, routers 297, or the like. For example, in some embodiments, component 211 may be borne by an "upstream" module (e.g., repeater 291 or the like) while or after component 210 is borne in a "downstream" module (e.g., another instance of repeater 291, communication satellite 293, server 294, or the like). Such downstream modules may "accept" such bits or other portions of implementation 202 or implementation 204 sequentially, for example, such as by amplifying, relaying, storing, checking, or otherwise processing what was received actively. Sensors and other "upstream" modules may likewise "accept" raw data, such as by measuring physical phenomena or accessing one or more databases.

In some embodiments, a medium bearing data (or other such event) may be "caused (directly or indirectly) by one or more instances of prior or contemporaneous measurements, decisions, transitions, circumstances, or other causal determinants. Any such event may likewise depend upon one or more other prior, contemporaneous, or potential determinants, in various implementations as taught herein. In other words, such events may occur "in response" to both preparatory (earlier) events and triggering (contemporaneous) events in some contexts.

In some embodiments, such integrated circuits 274 may comprise transistors, capacitors, amplifiers, latches, converters, or the like on a common substrate of a semiconductor material, operable to perform computational tasks or other transformations. An integrated circuit may be application-specific ("ASIC") in that it is designed for a particular use rather than for general purpose use. An integrated circuit may likewise include one or more instances of memory circuits, processors, field-programmable gate arrays (FPGA's), antennas, or other components, and may be referred to as a system-on-a-chip ("SoC").

In some embodiments, one or more instances of integrated circuits or other processors may be configured to perform auditory pattern recognition. In FIG. 2, for example, instances of the one or more input devices 278 may include a microphone or the like operable to provide auditory samples in data 231-242. Some form or portion of such output may be provided remotely, for example, to one or more instances of neural networks or other configurations of remote processors 295 operable to perform automatic or supervised speech recognition, selective auditory data retention or transmission, or other auditory pattern recognition, upon the samples. Alternatively or additionally such sound-related data may include annotative information relating thereto such as a capture time or other temporal indications, capture location or other source information, language or other content indications, decibels or other measured quantities, pointers to related data items or other associative indications, or other data aggregations or distillations as described herein.

In some embodiments, one or more instances of integrated circuits or other processors may be configured for optical image pattern recognition. In FIG. 2, for example, instances of lenses 271 or other input devices 278 may include optical sensors or the like operable to provide one or more of geometric, hue, or optical intensity information in data 231-242. Some form or portion of such output may be provided locally, for example, to one or more instances of optical character recognition software, pattern recognition processing resources, or other configurations of integrated circuits 274 operable to perform automatic or supervised image recognition, selective optical data retention or transmission, or the like. Alternatively or additionally such image-related data may include annotative information relating thereto such as a capture time or other temporal indications, capture location or other source information, language or other content indications, pointers to related data items or other associative indications, or other data aggregations or distillations as described herein.

Figure 25:
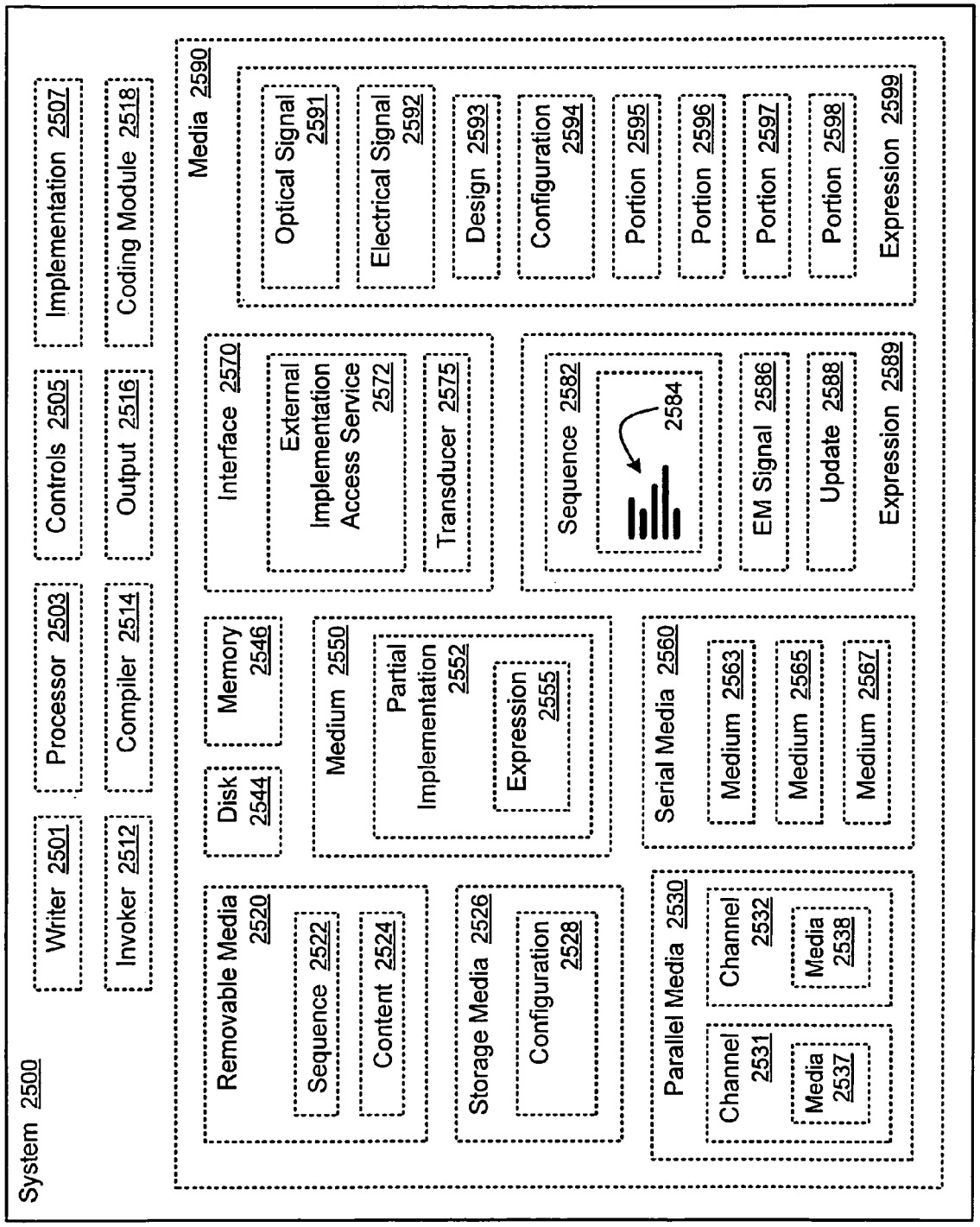
FIG. 25 depicts another context for introducing one or more processes, systems, or other articles described herein.

In some embodiments, one or more instances of integrated circuits or other processors may be configured to perform linguistic pattern recognition. In FIG. 25, for example, instances of input devices 278 may include keys, pointing devices, microphones, sensors, reference data, or the like operable to provide spoken, written, or other symbolic expressions in data 231-242. Some form or portion of such output may be provided locally, for example, to one or more instances of translation utilities, compilers, or other configurations of integrated circuits 274 operable to perform automatic or supervised programming or other language recognition, selective linguistic data retention or transmission, or the like. Alternatively or additionally such language-related data may include annotative information relating thereto such as a capture time or other temporal indications, capture location or other source information, language or other content indications, pointers to related data items or other associative indications, or other data classifications, aggregations, or distillations as described herein.

In some embodiments, one or more antennas 275 or receivers 273 may include a device that is the receiving end of a communication channel as described herein. For example, such a receiver may gather a signal from a dedicated conduit or from the environment for subsequent processing and/or retransmission. As a further example, such antennas or other receivers may include one or more instances of wireless antennas, radio antennas, satellite antennas, broadband receivers, digital subscriber line (DSL) receivers, modem receivers, transceivers, or configurations of two or more such devices for data reception as described herein or otherwise known.

In one variant, two or more respective portions of output data 231-242 may be sent from server 294 through respective channels at various times, one portion passing through repeater 291 and another through router 297. Such channels may each bear a respective portion of a data aggregation or extraction, a publication, a comparative analysis or decision, a record selection, digital subscriber content, statistics or other research information, a resource status or potential allocation, an evaluation, an opportunity indication, a test or computational result, or some other output 251-256 of possible interest. Such distributed media may be implemented as an expedient or efficient mode of bearing such portions of output data to a common destination such as interface 270 or holding device 289. Alternatively or additionally, some such data may be transported by moving a medium (carried on storage device 287, for example) so that only a small portion (a purchase or other access authorization, for example, or a contingent or supplemental module) is transferred via linkage 250.

In some embodiments, one or more instances of signal repeaters 291 may include a device or functional implementation that receives a signal and transmits some or all of the signal with one or more of an altered strength or frequency, or with other modulation (e.g., an optical-electrical-optical amplification device, a radio signal amplifier or format converter, a wireless signal amplifier, or the like). A repeater may convert analog to digital signals or digital to analog signals, for example, or perform no conversion. Alternatively or additionally, a repeater may reshape, retime or otherwise reorder an output for transmission. A repeater may likewise introduce a frequency offset to an output signal such that the received and transmitted frequencies are different. A repeater also may include one or more instances of a relay, a translator, a transponder, a transceiver, an active hub, a booster, a noise-attenuating filter, or the like.

In some embodiments, such communication satellite(s) 293 may be configured to facilitate telecommunications while in a geosynchronous orbit, a Molniya orbit, a low earth orbit, or the like. Alternatively or additionally, a communication satellite may receive or transmit, for example, telephony signals, television signals, radio signals, broadband telecommunications signals, or the like.

In some variants, processor 295 or any components 210-216 and 221-226 of implementations 201-206 may (optionally) be configured to perform flow variants as described herein with reference to FIGS. 14-19. An occurrence of such a variant can be expressed as a computation, a transition, or as one or more other items of data 231-242 described herein. Such output 251-256 can be generated, for example, by depicted components of primary system 200 or network 290 including one or more features as described with reference to FIGS. 5-13.

With reference now to FIG. 25, shown is an example of another system that may serve as a context for introducing one or more processes, systems or other articles described herein. As shown system 2500 comprises one or more instances of writers 2501, processors 2503, controls 2505, software or other implementations 2507, invokers 2512, compilers 2514, outputs 2516, coding modules 2518, or the like with one or more media 2590 bearing expressions or outputs thereof. In some embodiments, such media may include distributed media bearing a divided or otherwise distributed implementation or output. For example, in some embodiments, such media may include two or more physically distinct solid-state memories, two or more transmission media, a combination of such transmission media with one or more data-holding media configured as a data source or destination, or the like.

In some embodiments, transmission media may be "configured" to bear an output or implementation (a) by causing a channel in a medium to convey a portion thereof or (b) by constituting, adapting, addressing, or otherwise linking to such media in some other mode that depends upon one or more atypical traits of the partial or whole output or implementation. Data-holding elements of media may likewise be "configured" to bear an output or implementation portion (a) by holding the portion in a storage or memory location or (b) by constituting, adapting, addressing, or otherwise linking to such media in some other mode that depends upon one or more atypical traits of the partial or whole output or implementation. Such atypical traits may include a name, address, portion identifier, functional description, or the like sufficient to distinguish the output, implementation, or portion from a generic object.

In some embodiments described herein, "logic" and similar implementations can include software or other control structures operable to guide device operation. Electronic circuitry, for example, can manifest one or more paths of electrical current constructed and arranged to implement various logic functions as described herein. In some embodiments, one or more media are "configured to bear" a device-detectable implementation if such media hold or transmit a special-purpose device instruction set operable to perform a novel method as described herein. Alternatively or additionally, in some variants, an implementation may include special-purpose hardware or firmware components or general-purpose components executing or otherwise invoking special-purpose components. Specifications or other implementations may be transmitted by one or more instances of transmission media as described herein, optionally by packet transmission or otherwise by passing through distributed media at various times.

In some embodiments, one or more of the coding modules 2518 may be configured with circuitry for applying, imposing, or otherwise using a syntactic or other encoding constraint in forming, extracting, or otherwise handling respective portions of the device-detectable implementation or output. In encoding a software module or other message content, for example, compiler 2514 or coding module 2518 may implement one or more such constraints pursuant to public key or other encryption, applying error correction modes, certifying or otherwise annotating the message content, or implementing other security practices described herein or known by those skilled in the art. Alternatively or additionally, another instance of coding module 2518 may be configured to receive data (via receiver 273, e.g.) and decode or otherwise distill the received data using one or more such encoding constraints. Compiler 2514 may, in some variants, convert one or more of components 210-216 and 221-226 from a corresponding source code form before the component(s) are transmitted across linkage 250.

System 2500 may be implemented, for example, as one or more instances of stand-alone workstations, servers, vehicles, portable devices, removable media 2520, as components of primary system 200 or network 290 (of FIG. 2), or the like. Alternatively or additionally, media 2590 may include one or more instances of signal repeaters 291, communication satellites 293, servers 294, processors 295, routers 297, portions of primary system 200 as shown, or the like.

Media 2590 may include one or more instances of removable media 2520, tapes or other storage media 2526; parallel (transmission) media 2530; disks 2544; memories 2546; other data-handling media 2550; serial media 2560; interfaces 2570; or expressions 2589, 2599. Removable media 2520 can bear one or more device-detectable instances of instruction sequences 2522 or other implementations of flows described herein, for example. Alternatively or additionally, in some embodiments, removable media 2520 can bear alphanumeric data, audio data, image data, structure-descriptive values, or other content 2524 in a context that indicates an occurrence of one or more flows shown in FIGS. 14-19. In some circumstances, transmission media may bear respective portions of implementations as described herein serially or otherwise non-simultaneously. In some variants in which two portions 2597, 2598 constitute a partial or complete software implementation or product of a novel method described herein, portion 2597 may follow portion 2598 successively through serial media 2563, 2565, 2567 (with transmission of portion 2597 partly overlapping in time with transmission of portion 2598 passing through medium 2563, for example). As shown, parallel channels 2531, 2532 are respectively implemented at least in media 2537, 2538 of a bus or otherwise effectively in isolation from one another. In some embodiments, a bus may be a system of two or more signal paths—not unified by a nominally ideal conduction path between them—configured to transfer data between or among internal or external computer components. For example, one data channel may include a power line (e.g., as medium 2565) operable for transmitting content of the device-detectable implementation as described herein between two taps or other terminals (e.g., as media 2563, 2567 comprising a source and destination). In another such configuration, one or more media 2537 of channel 2531 may bear portion 2597 before, while or after one or more other media 2538 of parallel channel 2532 bear portion 2598. In some embodiments, such a process may occur "while" another process occurs if they coincide or otherwise overlap in time substantially (by several clock cycles, for example). In some embodiments, such a process may occur "after" an event if any instance of the process begins after any instance of the event concludes, irrespective of other instances overlapping or the like.

In a variant in which a channel through medium 2550 bears an expression 2555 partially implementing an operational flow described herein, the remainder of the implementation may be borne (earlier or later, in some instances) by the same medium 2550 or by one or more other portions of media 2590 as shown. In some embodiments, moreover, one or more controls 2505 may configure at least some media 2590 by triggering transmissions as described above or transmissions of one or more outputs 2516 thereof.

In some embodiments, the one or more "physical media" may include one or more instances of conduits, layers, networks, static storage compositions, or other homogenous or polymorphic structures or compositions suitable for bearing signals. In some embodiments, such a "communication channel" in physical media may include a signal path between two transceivers or the like. A "remainder" of the media may include other signal paths intersecting the communication channel or other media as described herein. In some variants, another exemplary system comprises one or more physical media 2590 constructed and arranged to receive a special-purpose sequence 2582 of two or more device-detectable instructions 2584 for implementing a flow as described herein or to receive an output of executing such instructions. Physical media 2590 may (optionally) be configured by writer 2501, transmitter 272, or the like.

In some embodiments, such a "special-purpose" instruction sequence may include any ordered set of two or more instructions directly or indirectly operable for causing multipurpose hardware or software to perform one or more methods or functions described herein: source code, macro code, controller or other machine code, or the like. In some embodiments, an implementation may include one or more instances of special-purpose sequences 2582 of instructions 2584, patches or other implementation updates 2588, configurations 2594, special-purpose circuit designs 2593, or the like. Such "designs," for example, may include one or more instances of a mask set definition, a connectivity layout of one or more gates or other logic elements, an application-specific integrated circuit (ASIC), a multivariate transfer function, or the like.

Segments of such implementations or their outputs may (optionally) be manifested one or more information-bearing static attributes comprising the device-detectable implementation. Such attributes may, in some embodiments, comprise a concentration or other layout attribute of magnetic or charge-bearing elements, visible or other optical elements, or other particles in or on a liquid crystal display or other solid-containing medium. Solid state data storage modules or other such static media may further comprise one or more instances of laser markings, barcodes, human-readable identifiers, or the like, such as to indicate one or more attributes of the device-detectable implementation. Alternatively or additionally such solid state or other solid-containing media may include one or more instances of semiconductor devices or other circuitry, magnetic or optical digital storage disks, dynamic or flash random access memories (RAMs), or the like. Magnetoresistive RAMs may bear larger implementation or output portions or aggregations safely and efficiently, moreover, and without any need for motors or the like for positioning the storage medium.

Segments of such implementations or their outputs may likewise be manifested in electromagnetic signals 2586, laser or other optical signals 2591, electrical signals 2592, or the like. In some embodiments, for example, such electrical or electromagnetic signals may include one or more instances of static or variable voltage levels or other analog values, radio frequency transmissions or the like. In some embodiments, the above-mentioned "optical" signals may likewise include one or more instances of time- or position-dependent, device-detectable variations in hue, intensity, or the like. Alternatively or additionally, portions of such implementations or their outputs may manifest as one or more instances of magnetic, magneto-optic, electrostatic, or other physical configurations 2528 of nonvolatile storage media 2526 or as external implementation access services 2572.

In some embodiments, physical media can be configured by being "operated to bear" or "operated upon to bear" a signal. For example, they may include physical media that generate, transmit, conduct, receive, or otherwise convey or store a device-detectable implementation or output as described herein. Such conveyance or storing of a device-detectable implementation or output may be carried out in a distributed fashion at various times or locations, or such conveyance or storing of a device-detectable implementation or output may be done at one location or time. As discussed above, such physical media "operated to bear" or "operated upon to bear" may include physical media that are atypically constituted or adapted to facilitate methods or functions as described herein.

In some configurations, one or more output devices 276 may present one or more results of transmitting the indication of the incentive to the individual to a putative provider of the therapeutic component in response to interface(s) 270 receiving one or more invocations or outputs of an implementation of this function via linkage 250. Such an "invocation" may, in some embodiments, comprise one or more instances of requests, hardware or software activations, user actions, or other determinants as described herein. Alternatively or additionally, in some embodiments, one or more input devices 278 may later receive one or more invocations or results of transmitting the indication of the incentive to the individual to a putative provider of the therapeutic component. In contexts like these, processor 295 or other components of network 290 may likewise constitute a secondary implementation having access to a primary instance of interface 270 implementing methods described herein.

Serial media 2560 comprises a communication channel of two or more media configured to bear a transition or other output increment successively. In some embodiments, for example, serial media 2560 may include a communication line or wireless medium (e.g., as medium 2565) between two signal-bearing conduits (e.g., terminals or antennas as media 2563, 2567). Alternatively or additionally, one or more lenses 271 or other light-transmissive media may comprise a serial medium between a light-transmissive medium and a sensor or other light receiver 273 or transmitter 272. In some embodiments, such "light-transmissive" media may (optionally) comprise metamaterials or other media operable for bearing one or more instances of microwave signals, radiowave signals, visible light signals, or the like.

In some embodiments, such a lens may be an optical element that causes light to converge or diverge along one or more signal paths. Such a light-transmissive medium may include a signal-bearing conduit, glass, or other physical medium through which an optical signal may travel. More generally, a signal-bearing conduit may be an electrical wire, a telecommunications cable, a fiber-optic cable, or a mechanical coupling or other path for the conveyance of analog or digital signals.

Alternatively or additionally, system 2500 may likewise include one or more instances of media for handling implementations or their outputs: satellite dishes or other reflectors 277, antennas 275 or other transducers 2575, arrays of two or more such devices configured to detect or redirect one or more incoming signals, caching elements or other data-holding elements (e.g., disks 2544, memories 2546, or other media 2590), integrated circuits 274, or the like. In some variants, one or more media may be "configured" to bear a device-detectable implementation as described herein by being constituted or otherwise specially adapted for that type of implementation at one or more respective times, overlapping or otherwise. Such "signal-bearing" media may include those configured to bear one or more such signals at various times as well as those currently bearing them.

In some embodiments, such caching elements may comprise a circuit or device configured to store data that duplicates original values stored elsewhere or computed earlier in time. For example, a caching element may be a temporary storage area where frequently-accessed data may be held for rapid access by a computing system. A caching element likewise may be machine-readable memory (including computer-readable media such as random access memory or data disks). In some embodiments, such caching elements may likewise comprise a latching circuit or device configured to store data that has been modified from original values associated with the data (held elsewhere or computed earlier in time, for example).

In one variant, respective portions 2595, 2596 of an expression 2599 of implementation 2507 may be sent through respective channels at various times. Invoker 2512 may request or otherwise attempt to activate a computer program or streaming media overseas via a telephone cable or other channel 2531. Meanwhile, output 2516 may attempt to trigger a session or other partial implementation 2552, success in which may be indicated by receiving expression 2555 into a visual display or other medium 2550. Such a program or other implementation may be made complete, for example, once both of these attempts succeed.

In some embodiments, transducer(s) 2575 may comprise one or more devices that convert a signal from one form to another form. For example, a transducer may be a cathode ray tube that transforms electrical signals into visual signals. Another example of a transducer comprises a microelectromechanical systems ("MEMS") device, which may be configured to convert mechanical signals into electrical signals (or vice versa).

Figure 26:
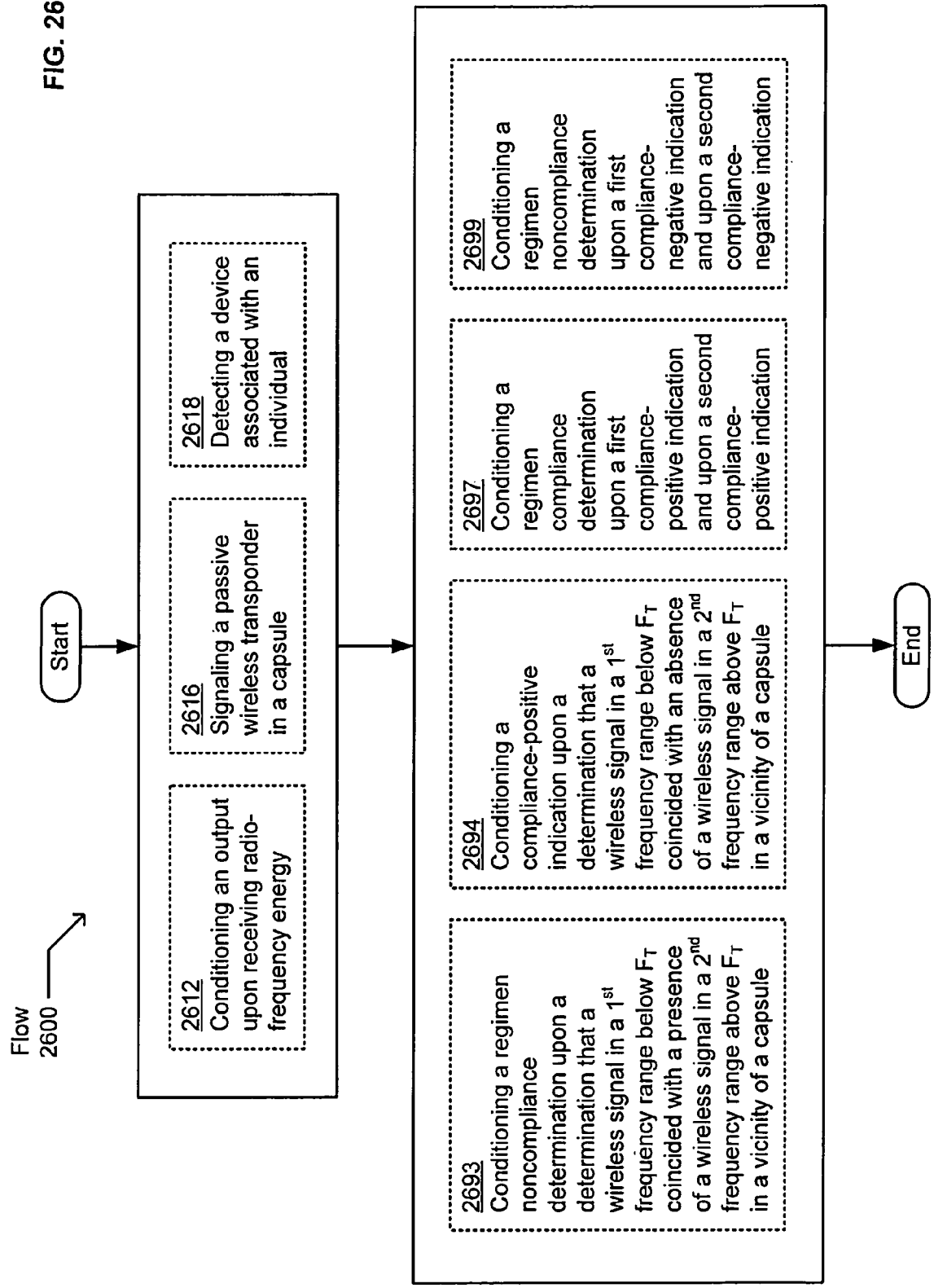
FIG. 26 depicts variants of flows shown in one or more of FIGS. 14-19.

With reference now to flow 2600 of FIG. 26 and to other flows described above, one or more operations of 10-16 may each (optionally) include or relate to one or more instances of operation 2612, operation 2616, or operation 2618 as described below. Such a "preparatory" operation may be carried out, for example, by one or more response modules or other detection logic (implemented in one or more products 150 or components 210-216 or interaction units 375, e.g.) configured to invoke, modulate, or otherwise influence one or more other components described herein.

Operation 2612 describes conditioning an output upon receiving radio-frequency energy (e.g. one or more processors 115, 655 executing an instruction sequence 693 for triggering a switch 145, taking and reporting a measurement 667, or enabling a compliance status indication 769 conditionally upon a result of applying one or more evaluation criteria 611 to at least one component 661 of data 660 derived from one or more sensors 2167, 2172 configured to detect radio-frequency energy 2168). This can occur, for example, in a context in which application module 110 includes one or more instances of event/condition detection logic 2150 or other data handling units capable of distinguishing whether a particular or other detectable signal has been received by such sensor(s) and in Which the triggering, reporting, enabling, or other output 251-256 does not occur without such RF energy 2168 having been received. Alternatively or additionally, such output may confirm or be further conditioned upon other indicia of ingestion, presence in a region, or other criteria as described herein. In some implementations of flow 1500, for example, the "first frequency range" may comprise a radio frequency band detectable by an instance of sensor 2167 having a 3 dB cutoff frequency of the threshold frequency.

In light of teachings herein, numerous existing techniques may be applied for configuring special-purpose circuitry or other structures effective for responding to radio-frequency energy and for generating conditional control signals as described herein without undue experimentation. See, e.g., U.S. Pat. No. 7,978,657 ("Multi-radio mesh network system supporting at least two different wireless communication standards and method of controlling the same"); U.S. Pat. No. 7,978,642 ("System and method for determining air interface information for radio resource management in wireless communications"); U.S. Pat. No. 7,978,062 ("Medical data transport over wireless life critical network"); U.S. Pat. No. 7,933,720 ("Biomolecule bonding detection apparatus using RF wireless energy transmission and method thereof"); U.S. Pat. No. 7,966,263 ("Wireless phone RF presentation instrument with sensor control"); U.S. Pat. No. 7,679,355 (" "); U.S. Pat. No. 7,515,556 ("System and method for low power radio operation in a wireless packet network"); U.S. Pat. No. 6,988,026 ("Wireless and powerless sensor and interrogator"); U.S. Pat. No. 6,144,852 ("Remote office administrative and maintenance system for cell sites in a wireless telecommunication network"); U.S. Pat. No. 7,835,319 ("System and method for identifying wireless devices using pulse fingerprinting and sequence analysis"); U.S. Pat. No. 7,969,311 ("Multi-path mitigation in rangefinding and tracking objects using reduced attenuation RF technology"); U.S. Pat. No. 7,863,994 ("System and method for increasing radio frequency (RF) microwave inductor-capacitor (LC) oscillator frequency tuning range"); U.S. Pat. No. 7,786,865 ("RFID reader and range indicating method for the RFID reader"); U.S. Pat. No. 7,696,821 ("Method and system for extending dynamic range of an RF signal"); U.S. Pat. No. 7,602,754 ("Short-range RF access point design enabling services to master and slave mobile devices").

Operation 2616 describes signaling a passive wireless transponder in a capsule (e.g. a condition detection module 2291 and one or more transmitters 272, 832 jointly causing a transmission of a radio-frequency interrogation signal 141 to a passive wireless transponder 492 within an ingestible capsule 491). This can occur, for example, in a context in which control module 117 transmits the interrogation signal 141 to determine whether one or more implants or other products 150 containing a specific configuration of transponder are within a region of interest (near enough to be detected by a handheld instrument 1350 or other interaction unit 375, e.g.), in which an expected reply signal 142 simply confirms the presence of such a device, and in which an absence of a reply signal signifies that no such device is in the region (for operation 11 or 16, e.g.). In some contexts, the region of interest may include a portion of a subject 382 or a stationary location through which a capsule may travel. Alternatively or additionally, a vessel that contains many such capsules (each containing one or two passive wireless transponders) may have some look-alike "smart" capsules intermixed therewith that can transmit a serial number or measurements 183 in reply signal 142. In some variants, a "smart" capsule may include a micro-battery 182 and be configured to transmit the capsule's configuration, status, or other raw data 410 (or to record them) at regular intervals or upon detectable events during its passage per vias naturales.

In light of teachings herein, numerous existing techniques may be applied for configuring special-purpose circuitry or other structures effective for interacting with a radio-frequency or other passive or low power wireless transponder as described herein without undue experimentation. See, e.g., U.S. Pat. No. 6,988,026 ("Wireless and powerless sensor and interrogator"); U.S. Pat. No. 7,712,674 ("RFID devices for verification of correctness, reliability, functionality and security"); U.S. Pat. No. 7,973,664 ("Closure having RFID and foil"); U.S. Pat. No. 7,941,095 ("LPRF device wake up using wireless tag"); U.S. Pat. No. 7,538,657 ("Radio frequency identification based sensor"); U.S. Pat. No. 7,844,505 ("Automated real-time distributed tag reader network"); U.S. Pat. No. 7,855,630 ("Fuse state indicator systems"); U.S. Pat. No. 7,777,610 ("Radio frequency identification apparatuses"); U.S. Pat. No. 7,629,888 ("RFID device with changeable characteristics"); U.S. Pat. No. 7,989,313 ("Method and apparatus for creating RFID devices"); U.S. Pat. No. 7,979,034 ("Architecture for RFID tag reader/writer"); U.S. Pat. No. 7,978,494 ("Radio frequency identification device initializing a memory using an offset voltage"); U.S. Pat. No. 7,978,051 ("RFID interrogator device"); U.S. Pat. No. 7,986,239 ("Methods and apparatus to visualize locations of radio frequency identification (RFID) tagged items"); U.S. Pat. No. 7,981,025 ("Adjustable implant and method of use"); U.S. Pat. No. 7,969,307 ("Diagnostic radio frequency identification sensors and applications thereof"); U.S. Pat. No. 7,855,643 ("Tracking systems, passive RFIDs, methods of locating and identifying RFIDs, and methods of tracking items"); U.S. Pat. No. 7,988,055 ("Uncontrolled passive radio frequency identification tag and system with 3-D positioning"); U.S. Pat. No. 7,948,381 ("Reversibly deactivating a radio frequency identification data tag").

Operation 2618 describes detecting a device associated with an individual (e.g. a logic circuit or other input device 178, in response to one or more sensors 179, recognizing a person's dispenser 170, cell phone, body contact device 2175, security badge, vehicle, or other interaction unit 375 that identifies subject 382 or has a proximity to or other a priori association with subject 382). This can occur, for example, in a context in which a wireless signal 1034, 1230 is received from the device, in which the device enters a detection region of such sensor(s), in which "the user" or "the bearer" is an initially sufficient identification, and in which one or more images are taken of the region (for operation 16, e.g.) to characterize that association (the person in possession of the device, e.g.). Alternatively or additionally, the detection and association may signal a compliance-positive indication 687 or compliance-negative indication 689. A compliance-negative indication may result, for example, in a context in which a regimen calls for refraining from eating at night and in which the device is a refrigerator or kitchen door. A compliance-positive indication may conversely result, for example, in a context in which a regimen calls for exercise and the subject's running shoes or exercise equipment are monitored.

In light of teachings herein, numerous existing techniques may be applied for configuring special-purpose circuitry or other structures effective for associating a device with an individual as described herein without undue experimentation. See, e.g., U.S. Pat. No. 6,753,781 ("Infant and parent matching and security system and method of matching infant and parent"); U.S. Pat. No. 7,984,849 ("Portable magnetic stripe reader for criminality security applications"); U.S. Pat. No. 7,988,038 ("System for biometric security using a fob"); U.S. Pat. No. 7,734,928 ("Secure entry of a user-identifier in a publicly positioned device"); U.S. Pat. No. 7,986,218 ("Sensor devices for structural health monitoring"); U.S. Pat. No. 7,154,275 ("Method and apparatus for detecting individuals using electrical field sensors"); U.S. Pat. No. 7,834,766 ("Method and apparatus for tracking objects and people"); U.S. Pat. No. 7,536,188 ("Communication device locating system"); U.S. Pat. No. 7,394,353 ("Modular vehicle key system"); U.S. Pat. No. 7,978,083 ("Hand washing compliance detection system"); U.S. Pat. No. 7,944,342 ("Prescription compliance device and method of using device"); U.S. Pat. No. 7,978,082 ("RFID-based personnel tracking"); U.S. Pat. No. 7,642,895 ("Garage door operator having thumbprint identification system"); U.S. Pat. No. 6,910,628 ("Travel system and methods utilizing multi-application airline passenger cards").

In some variants, one or more implementations 201-206 may (optionally) be configured to respond to a not-so-smart pill (a capsule 491 lacking computational capability, e.g.) having an immersion-responsive structure 905 (a barrier 1018 that temporarily prevents a passive wireless transponder 492 therein from responding to radio frequency energy 2168 until it melts or dissolves, e.g.) or an acid-activated sensor 2164 (configured to trigger or enable capsule 491 to transmit a wireless signal 1034, 1230 in response to exposure to stomach acid, mucous, stool, or *H. pylori*, e.g.) or other such structures by which no tag will be detected (characterized by a lack of a reply signal 142 in response to a suitable interrogation signal 141 until exposure to a subject's body un-masks or activates passive wireless tag 492, e.g.). This can occur, for example, in a context in which an ex situ device (monitor unit 850 or detection device 1090, e.g.) is configured to detect such wireless signals or other detectable indicia (raw data or indications of ingestion or compliance, e.g.) in a confined area within which a human or other subject 382 resides (hospital wards, jails, or nursing homes, e.g.). Alternatively or additionally, such a pill may be configured to alter one or more signal attributes (timing, frequency, or bandwidth of reply signal 142, e.g.) in response to exposure to a subject's body (indicated by temperature sensor data 422 or chemical sensor data 423 or other raw data 410 indicative of in situ bodily fluids or samples 2015, 2017, e.g.).

With reference again to flow 2600 of FIG. 26 and to other flows described above, one or more operations of 21-26 may each (optionally) include or relate to one or more instances of operation 2693, operation 2694, operation 2697, or operation 2699 as described below. Such a "utility" operation may be carried out, for example, by application or decision logic (implemented in one or more primary components 221-226 or distillation units 460 or other data handling units responsive to one or more preparatory operations, e.g.) configured to implement or communicate one or more outputs of 251-256 or other useful results described herein.

Operation 2693 describes conditioning a regimen noncompliance determination upon a determination that a wireless signal in a first frequency range below a reference frequency coincided with a presence of a wireless signal in a second frequency range above the reference frequency in a vicinity of a capsule (e.g. decision module 2022 transmitting a regimen noncompliance determination 688 manifesting as a control signal 2052 selectively in response to a "first" signal 2431 having a peak 2351 in a "lower" frequency range 2377 and "second" signal 2433 having a peak (not shown) in a "higher" frequency range 2373). This can occur, for example, in a context in which such signals have frequency-spectrum energy components (peaks 2351, 2352, e.g.), in which decision module 2022 is configured to ignore such components smaller than amplitude 2342 (as noise, e.g.), in which primary unit 950 receiving the wireless signal in the 1st frequency range (below $F_T$, e.g.) signifies that capsule 910 has transmitted the wireless signals (in response to an immersion of capsule 910 detected by a pressure sensor or other immersion-responsive structure 905, e.g.), and in which primary unit 950 receiving the wireless signal in the 2nd frequency range (above $F_T$, e.g.) signifies that the indication of ingestion is apparently fraudulent (the capsule having been immersed but not ingested, e.g.). In some variants, for example, in a region 2430 containing product 2410 (as a "vicinity of a capsule," e.g.), either incident energy 2408 or transmitted energy 2409 may contain the "first" and "second" signals within respective ranges and the respective conditions "coincided" by existing in an overlapping region contemporaneously (within 0.1 or 1 or 10 seconds or 1 or 10 minutes, e.g.). Alternatively or additionally, response module 2010 may implement a data handling unit 610 configured to receive data from a capsule 491 or device 860 that implements product 2410. Moreover in some implementations of decision module 2024 (software, e.g.), the compliance-positive indication may also depend upon whether the incident energy 2408 containing the signal(s) exhibited an absence of a recognizable wireless signal in at least one such higher-frequency range 2373 for a sustained period (of minutes or hours, e.g.), which may indicate ingestion or digestion in some contexts.

In light of teachings herein, numerous existing techniques may be applied for configuring special-purpose circuitry or other structures effective for using wireless signals for characterizing a region and for indicating whether an individual has complied with a regimen as described herein without undue experimentation. See, e.g., U.S. Pat. No. 7,876,228 ("Method and apparatus for monitoring ingestion of medications using an implantable medical device"); U.S. Pat. No. 7,957,984 ("Device for facilitating compliance with medication regimen"); U.S. Pat. No. 7,822,472 ("Methods and systems for optimizing exercise compliance diagnostic parameters"); U.S. Pat. No. 7,820,108 ("Marker detection method and apparatus to monitor drug compliance"); U.S. Pat. No. 7,979,284 ("Interactive video based remote health monitoring system"); U.S. Pat. No. 7,959,540 ("Systems and methods for administering an exercise program"); U.S. Pat. No. 7,978,564 ("Interactive medication container"); U.S. Pat. No. 7,956,727 ("Methods and systems for medication management"); U.S. Pat. No. 7,951,046 ("Device; method and computer program product for tracking and monitoring an exercise regimen"); U.S. Pat. No. 7,918,779 ("Therapeutic methods using electromagnetic radiation"); U.S. Pat. No. 7,901,383 ("Systems and methods for administering a medical regimen"); U.S. Pat. No. 7,860,583 ("System and method for dynamically adjusting patient therapy"); U.S. Pat. No. 7,819,826 ("Implantable thermal treatment method and apparatus"); U.S. Pat. No. 7,747,454 ("System and method for real time management of a drug regimen"); U.S. Pat. No. 7,639,120 ("Prescription compliance device and method of using device"); U.S. Pat. No. 7,526,335 ("Communications system for an implantable device and a drug dispenser").

Operation 2694 describes conditioning a compliance-positive indication upon a determination that a wireless signal in a first frequency range below a reference frequency coincided with an absence of a wireless signal in a second frequency range above the reference frequency in a vicinity of a capsule (e.g. decision module 2024 generating a regimen compliance determination 686 selectively in response to signal 2431 having a peak 2351 in frequency range 2371 and no recognizable peak being detected in one or more higher-frequency ranges 2373, 2374). This can occur, for example, in a context in which such signals have frequency-spectrum energy components (peaks 2351, 2352, e.g.), in which decision module 2024 is configured to ignore such components smaller than a threshold 2061 (expressed as a percentage between 5% and 95% of a nominal maximum amplitude 2341, e.g.), and in which $F_T$ is a reference frequency within range 2372. In some variants, for example, response module 2010 may implement a data handling unit 610 configured to receive data from a capsule 491 or device 860 that implements product 2410. Moreover in some implementations of decision module 2024 (software, e.g.), the compliance-positive indication may also depend upon whether the incident energy 2408 containing the signal(s) exhibited an absence of a recognizable wireless signal in at least one such higher-frequency range 2373 for a sustained period (of minutes or hours, e.g.), which may indicate ingestion or digestion in some contexts.

Operation 2697 describes conditioning a regimen compliance determination upon a first compliance-positive indication and upon a second compliance-positive indication (e.g. decision module 2021 transmitting a present-day text or audio message 2042 via interaction unit 375 that states "you have met all the requirements of regimen 2001" in response to timing data 2037 indicating acceptably timely dosage administrations for the past week and to a regimen compliance determination 686 of a week ago). Alternatively or additionally, such "first" and "second" compliance-positive indications 687 may sometimes mutually corroborate the same event, for example, such as in a context in which operations 10 and 11 each produce a respective compliance-positive indication 2071, 2072 (that subject 382 has ingested one or more capsules 491, 910 or other devices as articulated by regimen 2001, e.g.). Alternatively or additionally, one or more of the compliance-positive indications 687 may be received as a direct reply 2034 to a voice or text query 2032 expressing a question like "is subject 382 still taking prednisone daily?" (in an interchange with a care provider 383 via interaction unit 375, e.g.). In some contexts, for example, regimen 2001 may define an 80% success rate (at daily or twice-daily doses or monitoring events, e.g.) as "acceptably timely."

In light of teachings herein, numerous existing techniques may be applied for configuring special-purpose circuitry or other structures effective for generating composite indications of regimen compliance or noncompliance as described herein without undue experimentation. See, e.g., U.S. Pat. No. 7,917,377 ("Patient data mining for automated compliance"); U.S. Pat. No. 7,752,056 ("Network media access control system for encouraging patient compliance with a treatment plan"); U.S. Pat. No. 7,725,327 ("Computer system and method for generating healthcare risk indices using medication compliance information"); U.S. Pat. No. 7,636,667 ("Network media access control system for encouraging patient compliance with a treatment plan"); U.S. Pat. No. 7,515,734 ("Device, system and method for determining compliance with a positioning instruction by a figure in an image"); U.S. Pat. No. 6,587,829 ("Method and apparatus for improving patient compliance with prescriptions"); U.S. Pat. No. 7,853,468 ("System and methods for integrated compliance monitoring"); U.S. Pat. No. 7,382,263 ("Oral drug compliance monitoring using radio frequency identification tags"); U.S. Pat. No. 6,442,422 ("Compliance monitoring apparatus and method"); U.S. Pat. No. 7,991,628 ("Generating output data based on patient monitoring"); U.S. Pat. No. 7,981,058 ("Intelligent wearable monitor systems and methods"); U.S. Pat. No. 7,830,962 ("Monitoring remote patients"); U.S. Pat. No. 7,887,599 ("Methods of use of biodegradable injectable implants"); U.S. Pat. No. 7,937,319 ("Methods and systems for compliance monitoring knowledge base"); U.S. Pat. No. 7,741,103 ("Integrated screening and confirmation device").

Operation 2699 describes conditioning a regimen noncompliance determination upon a first compliance-negative indication and upon a second compliance-negative indication (e.g. decision module 2023 transmitting a text or audio message 2041 via interaction unit 375 that states "subject 382 is not meeting the minimum requirements of regimen 2002" in response to timing data 2038 indicating N or more missed events within a prescribed interval). This can occur, for example, in a context in which N is 2 or more, in which the events are dosages or other therapeutic administrations, in which the prescribed interval is a week or a month, and in which the "first" and "second" compliance-negative indications 689 each signify a "missed" dosage or other event specified by one or more regimens (research or security protocols, e.g.) defined by a security director, researcher, or other service provider 310.

Figure 27:
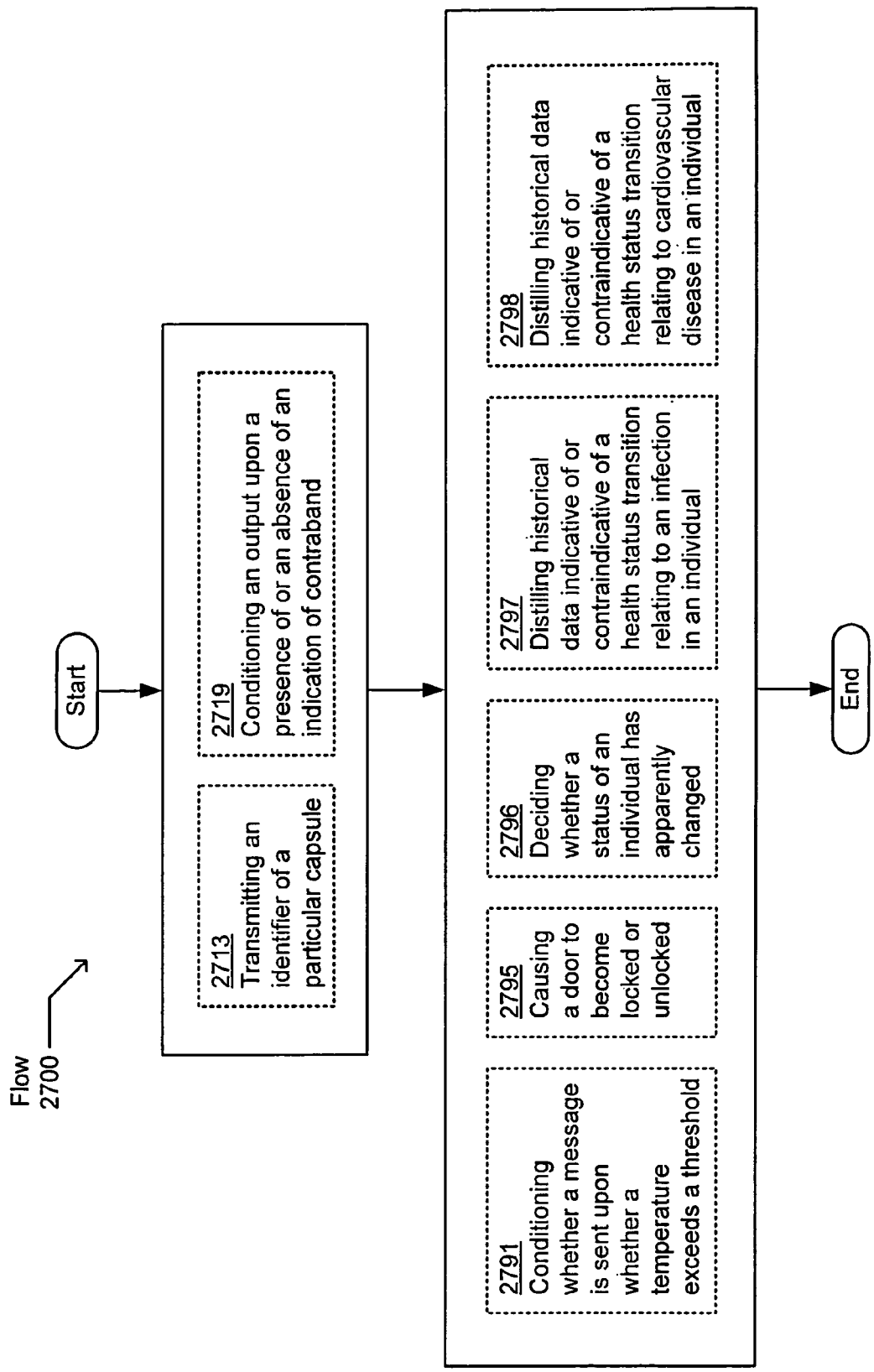

With reference now to flow 2700 of FIG. 27 and to other flows described above, one or more operations of 10-16 may each (optionally) include or relate to one or more instances of operation 2713 or operation 2719 as described below. Such a "preparatory" operation may be carried out, for example, by one or more distillation units or other detection logic (implemented in one or more application modules 110 or components 210-216 or interaction units 375, e.g.) configured to invoke, modulate, or otherwise influence one or more other components described herein.

Operation 2713 describes transmitting an identifier of a particular capsule (e.g. one or more distillation modules 435 recording one or more identifiers 581, 582 received from or otherwise associated with a respective capsule 491, 910, 1153). This can occur, for example, in a context in which application module 110 implements a distillation unit 460 or other data handling unit 610 operably coupled with one or more media 550 and in which some or all such capsules in a dispenser 170 or other vessel 160 each contain a passive wireless transponder 492 tuned to a capsule-specific frequency, a consecutive serial number marking, or some other device-detectable attribute suitable for distinguishing each capsule from other capsules in the vessel. Alternatively or additionally, one or more distillation modules 434, 435 may implement a distillation protocol 657 configured to cause a recordation of timing data 538 indicative of a contemporaneous capture of one or more images 632, 633 (as one or more pointers 676, 677 to a video clip 642 or other image data 424 that depicts a venue or movements of a subject 382 for a period of hours or days, e.g.), an indication of ingestion 445, or other event indications 440 as described herein. In some contexts, moreover, a "smart" capsule may be configured to perform operation 2713 by identifying itself in a wireless signal 1034, 1230 responsive to one or more of detecting several minutes or hours of darkness or immersion in an ambient temperature of about 37° C., a pH change larger than a threshold 561 (of 0.1 or 1, e.g.) or other such chemical transitions 443 indicative of prior ingestion, receiving RF energy 2168 into a passive wireless transponder 492, or other such event indications 440 as described herein.

In light of teachings herein, numerous existing techniques may be applied for configuring special-purpose circuitry or other structures effective for identifying capsules or other devices as described herein without undue experimentation. See, e.g., U.S. Pat. No. 7,839,432 ("Detector selection for monitoring objects"); U.S. Pat. No. 7,983,682 ("Context based connectivity for mobile devices"); U.S. Pat. No. 7,952,480 ("RFID tag filtering and monitoring"); U.S. Pat. No. 7,619,819 ("Method and apparatus for drug product tracking using encoded optical identification elements"); U.S. Pat. No. 7,876,228 ("Method and apparatus for monitoring ingestion of medications using an implantable medical device"); U.S. Pat. No. 7,786,864 ("Vehicular RFID and sensor assemblies"); U.S. Pat. No. 7,722,521 ("Method and apparatus for automatic tracking and identification of device components"); U.S. Pat. No. 7,941,534 ("System and method to authenticate users to computer systems"); U.S. Pat. No. 7,983,763 ("Implanted lead sleeve having RFID tag"); U.S. Pat. No. 7,916,013 ("RFID detection and identification system for implantable medical devices"); U.S. Pat. No. 7,650,888 ("Method and system for identification of a medical implant"); U.S. Pat. No. 7,518,502 ("System and method for tracking surgical assets").

Operation 2719 describes conditioning an output upon a presence of or an absence of an indication of contraband (e.g. sample tester 119 and control module 117 jointly manifesting a controlled substance or metabolite thereof having been detected in a sample 2015 of hair or blood from subject 382 as a regimen noncompliance determination 688, or a lack thereof as a compliance-positive indication 687). Such an indication of contraband may be of interest, for example, at a sports event (as a sign of doping, e.g.) or at an airport (as a sign of smuggling or of a breach of a quarantine, e.g.) or at a prison or school or any other context in which a metal device or other object of contraband may constitute a threat (to safety or security, e.g.). In some variants, for example, such modules may be configured to disable a transistor 146, a flush actuator 2283, or another mechanical component 130 (in commode 810, e.g.) conditionally (in response to a preliminary indication 2074 that a sample 2017 of excrement may contain a parasite or prohibited material, e.g.). This can occur, for example, in a context in which the preliminary indication 2074 is easy to implement but susceptible to a high rate of false positives; in which a more costly confirmatory test (with a low rate of false positives, e.g.) cannot be performed unless such a sample 2017 is preserved; and in which security personnel are available to obtain sample 2017 provided that the excrement is not flushed. In some contexts, for example, such a preliminary indication 2074 may be inferred from dilated pupils, signs of anxiety or fever (detectable by image recognition module 2258 or other pattern recognition logic 2260, for example, in an image 634, sample clip 643, or other data components 662), or other such device-detectable attributes 2222 of subject 382 (obtained as temperature sensor data 422 or other raw data 410 obtained via a camera 2232 or other sensor 2233, e.g.). Alternatively or additionally, one or more such indications 2074 of contraband can be received from an ingestible device 860 or from a detection device (from a care provider 383, guard, or other third party, for example, via one or more input devices 178, 278).

In light of teachings herein, numerous existing techniques may be applied for configuring special-purpose circuitry or other structures effective for detecting contraband as described herein without undue experimentation. See, e.g., U.S. Pat. No. 7,991,213 ("System for detecting infectious agents using computer-controlled automated image analysis"); U.S. Pat. No. 7,560,239 ("Homogeneous enzyme immunoassay for simultaneous detection of multiple analytes"); U.S. Pat. No. 7,927,548 ("Specimen sample collection device and test system"); U.S. Pat. No. 6,740,500 ("Method of screening for non-steroidal neuropsychiatric agents"); U.S. Pat. No. 7,943,384 ("Apparatus and methods for sorting particles"); U.S. Pat. No. 7,837,939 ("Rapid sample collection and analysis device and methods of use"); U.S. Pat. No. 7,951,989 ("Methods of screening agents for activity using teleosts"); U.S. Pat. No. 7,550,112 ("Sample collection cup with integrated activatable sample analysis system"); U.S. Pat. No. 7,798,414 ("Human and scanner readable radiation exposure indicator with reactive barcode"); U.S. Pat. No. 7,745,115 ("Method for the surveillance for biological, chemical and radiological agents"); U.S. Pat. No. 7,658,727 ("Implantable medical device with enhanced biocompatibility and biostability"); U.S. Pat. No. 7,351,982 ("Portable nuclear material detector and process"); U.S. Pat. No. 7,836,850 ("Method and system for tracking and managing animals and/or food products"); U.S. Pat. No. 7,082,369 ("Distributed biohazard surveillance system and apparatus for adaptive aerosol collection and synchronized particulate sampling"); U.S. Pat. No. 7,479,877 ("Method and system for utilizing multiple sensors for monitoring container security, contents and condition"); U.S. Pat. No. 7,945,393 ("Detection of pathogenic microorganisms using fused sensor data").

With reference again to flow 2700 of FIG. 27 and to other flows described above, one or more operations of 21-26 may each (optionally) include or relate to one or more instances of operation 2791, operation 2795, operation 2796, operation 2797, or operation 2798 as described below. Such a "utility" operation may be carried out, for example, by application or decision logic (implemented in one or more primary components 221-226 or distillation units 460 or other data handling units responsive to one or more preparatory operations, e.g.) configured to implement or communicate one or more outputs of 251-256 or other useful results described herein.

Operation 2791 describes conditioning whether a message is sent upon whether a temperature exceeds a threshold (e.g. decision module 2026 transmitting an order for an antibiotic material component 523 or other fever-indicative signal 2053 to a nurse, pharmacist, or other material provider 381 selectively in response to one or more temperature measurement samplings 673 exceeding a temperature threshold 2063 high enough to constitute a fever). This can occur, for example, in a context in which a physician selects a threshold 1 or 2 degrees above 37° C. and a regimen 2004 that would otherwise require a human subject 382 to take such antibiotics prophylactically, and in which decision module 2026 transmits no signal in response to a consistent normalcy indication 2472 (indicating a normal body temperature, e.g.) in such samplings 673. Alternatively or additionally, decision module 2026 may be configured to cause a transmission of a compliance-positive indication 687 selectively in response to temperature sensor data 422 indicating a temperature high enough (indicating a sensor 2166 in capsule 491 or a sensor 2171 in body contact device 2175 exceeding a threshold 2064 a few degrees below 37° C., e.g.) to signify having been ingested by or otherwise put in contact with subject 382. This can occur, for example, in a context in which regimen 2004 calls for one or more timely indications of ingestion 2445 or temperature measurements. Alternatively or additionally, one or more images 1364 in the infrared band can be used to indicate whether a region 1330 has a temperature high enough (above 37° C., e.g.) to indicate a pressure ulcer or other abnormality detectable as a locally elevated temperature.

In light of teachings herein, numerous existing techniques may be applied for configuring special-purpose circuitry or other structures effective for detecting indications of elevated temperatures as described herein without undue experimentation. See, e.g., U.S. Pat. No. 7,934,836 ("Projector that is capable of superimposing and displaying a visible image and an invisible infrared image"); U.S. Pat. No. 7,891,866 ("Emissivity independent non-contact high temperature measurement system and method"); U.S. Pat. No. 7,878,016 ("Device and method for on-die temperature measurement"); U.S. Pat. No. 7,819,578 ("Fluid temperature measurement device"); U.S. Pat. No. 7,954,994 ("Combined pressure/temperature sensor having centric temperature measurement"); U.S. Pat. No. 7,775,711 ("Temperature measurement device and measurement method"); U.S. Pat. No. 7,981,046 ("Temperature measurement device"); U.S. Pat. No. 6,210,427 ("Support apparatus with a plurality of thermal zones providing localized cooling"); U.S. Pat. No. 6,071,254 ("Near hyperthermic heater wound covering"); U.S. Pat. No. 7,914,564 ("System and method for patient temperature control employing temperature projection algorithm"); U.S. Pat. No. 7,590,449 ("Patient signaling method for treating cardiovascular disease"); U.S. Pat. No. 6,995,675 ("Method and system for agricultural data collection and management").

Operation 2795 describes causing a door to become locked or unlocked (e.g. a motor 133, relay 147, or other actuator interface 2250 configuring a lock 132 on door 131 into a locked state in response to a compliance-negative indication 689 that indicates that subject 382 is apparently not complying with a regimen 781). This can occur, for example, in a context in which processor 115 invokes code 104 for implementing one or more criteria 121, 122 of a conventional security protocol 120 and in which application module 110 includes a product 150 or interaction unit 375 as described herein. In some variants, for example, detection unit 180 includes one or more sensors 179 configured to recognize a badge or biometric data 536 associated with an employee or other authorized individual (subject 382, e.g.) as an instance of operation 16 or 2713. Alternatively or additionally, processor 115 can perform operation 2795 by causing lock 132 to be activated until and unless an indication of ingestion 445 is obtained or otherwise in response to a regimen noncompliance determination 688 (as a disciplinary or security measure, e.g.).

In some contexts a capsule or other vessel 490 (including a passive wireless transponder 492 or a micro-battery 182 operatively coupled to a transmitter 272, e.g.) may be configured to transmit temperature sensor data 422, chemical sensor data 423, or other raw data 410 or a comparator output (as an indication of ingestion 445 or contraband, e.g.). This can occur, for example, in a prison, a workplace, or other context in which ingress or egress is closely monitored (by a guard who controls a door 131 while monitoring a compliance-status-indicative output device 176, e.g.) or in which a control element 140 or mechanical component 130 (locking or unlocking mechanism, e.g.) is directly controlled in response to a compliance-positive indication 687 or compliance-negative indication 689.

Operation 2796 describes deciding whether a status of an individual has apparently changed (e.g. decision module 2025 applying one or more status-quo-indicative evaluation criteria 612 to determine whether a symptom suffered by a subject 382 has been resolved). This can occur, for example, in a context in which a service provider 310 specifies both a therapeutic material component 534 and a protocol identifier 775 that specifies a daily or other monitoring component calling for a query of "was the treatment? . . . press 1 for yes, 2 for somewhat, and 3 for no." In some contexts, a reply signal 142 received in response to such a query can be used as a high-prolixity-indicative determinant 767 (if "no," e.g.) or a low-prolixity-indicative determinant 768 (if "yes," e.g.) so that a subject 382 or care provider 383 receives a opportunity to elaborate (with an explanatory audio clip 642 of one or more minutes or other suitable resources, e.g.) that is conditional upon a symptom not having been resolved. Alternatively or additionally, (a monitoring component of) one or more regimens 2001-2004 may include a recordation of one or more measurements or other status indications 2073 in association with timing data 2039 (indicating a persistent symptom or a time of its resolution, e.g.).

In light of teachings herein, numerous existing techniques may be applied for configuring special-purpose circuitry or other structures effective for measuring or otherwise documenting an onset, an abatement, or other such events reflecting symptoms of hypertension, diabetes, or many other such (generally treatable) pathologies. See, e.g., U.S. Pat. No. 7,468,040 ("Methods and systems for implantably monitoring external breathing therapy"); U.S. Pat. No. 7,465,273 ("Method for monitoring pre-eclamptic patients"); U.S. Pat. No. 7,404,796 ("System for determining insulin dose using carbohydrate to insulin ratio and insulin sensitivity factor"); U.S. Pat. No. 7,400,257 ("Vital signals and glucose monitoring personal wireless system"); U.S. Pat. No. 7,397,380 ("Device and method for monitoring state of thermal comfort of a baby at sleep or a partially disabled patient"); U.S. Pat. No. 7,395,216 ("Using predictive models to continuously update a treatment plan for a patient in a health care location"); U.S. Pat. No. 7,379,885 ("System and method for obtaining, processing and evaluating patient information for diagnosing disease and selecting treatment"); U.S. Pat. No. 7,356,364 ("Device for optical monitoring of constituent in tissue or body fluid sample using wavelength modulation spectroscopy, such as for blood glucose levels"); U.S. Pat. No. 7,340,296 ("Detection of pleural effusion using transthoracic impedance"); U.S. Pat. No. 7,297,108 ("Disease management system and method including analysis of disease specific changes"); U.S. Pat. No. 7,223,237 ("Implantable biosensor and methods for monitoring cardiac health"); U.S. Pat. No. 7,177,686 ("Using photo-plethysmography to monitor autonomic tone and performing pacing optimization based on monitored autonomic tone"); U.S. Pat. No. 7,035,684 ("Method and apparatus for monitoring heart function in a subcutaneously implanted device"); U.S. Pat. No. 6,817,980 ("Automated diagnostic system and method including disease timeline"); U.S. Pat. No. 6,770,029 ("Disease management system and method including correlation assessment").

Operation 2797 describes distilling historical data indicative of or contraindicative of a health status transition apparently relating to an infection in an individual (e.g. processor 655 invoking or otherwise implementing one or more distillation criteria 623 effective for selectively retaining one or more normalcy indications 2471, 2472 specifically identified by a physician or other care provider 383 as relating to infection). This can occur, for example, in a context in which care provider 383 assigns a specific infection-related monitoring regimen 2003 to subject 382 that results in either a normalcy indication 2471 or a recorded thermal transition 442 being associated with subject 382. In some variants, for example, such a thermal transition 442 may trigger an urgent message 2044 to care provider 383 (if it indicates a thermal increase above a prescribed threshold 2062, such as 38° C. or higher in a human patient, e.g.) or an event record 488 in storage medium 691 (if it indicates a fever has abated, e.g.). Alternatively or additionally, monitoring regimen 2003 may be configured to make such notifications or recordings contingent upon one or more white counts exceeding threshold 2063 (as determined by sample tester 119, e.g.), reply signals 2051 received from another care provider 383 in response to telephonic or other infection-related queries ("has subject 382 had chills?" sent via interaction unit 375, e.g.), or other such signals 2051 of an onset or abatement of infection.

Operation 2798 describes distilling historical data indicative of or contraindicative of a health status transition apparently relating to cardiovascular disease in an individual (e.g. condition detection module 2292 detecting when and whether blood pressure measurements in a data series 695 indicate an onset of hypertension, an abatement of hypertension, or a lack of change of an individual's hypertensive or non-hypertensive state). This can occur, for example, in a context in which an antihypertensive material component 531 has been prescribed and in which hundreds of measurements in data series 695 can be distilled into a data plot 694 (of blood pressure vs. time. e.g.) or in a phrase like "normal since last September" or "normal until last September" or "still borderline hypertensive."

Figure 28:
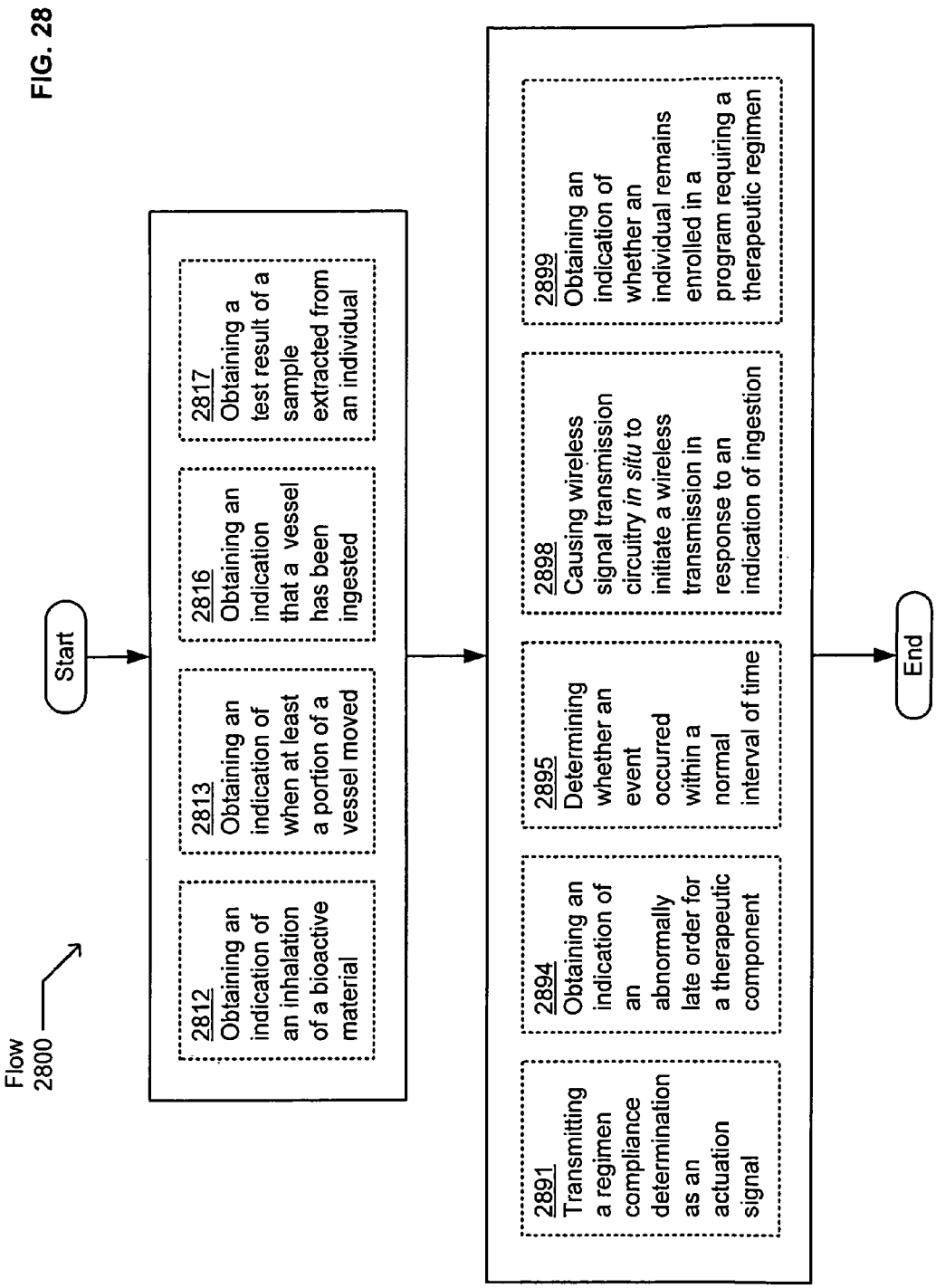

With reference now to flow 2800 of FIG. 28 and to other flows described above, one or more operations of 10-16 may each (optionally) include or relate to one or more instances of operation 2812, operation 2813, operation 2816, or operation 2817 as described below. Such a "preparatory" operation may be carried out, for example, by one or more distillation units or other detection logic (implemented in one or more application modules 110 or components 210-216 or interaction units 375, e.g.) configured to invoke, modulate, or otherwise influence one or more other components described herein.

Operation 2812 describes obtaining an indication of an inhalation of a bioactive material (e.g. one or more modules for obtaining an indication of an inhalation of a bioactive material 2142 detecting an auditory or other direct indication of an actuation of an inhaler 1158 or similar dispensing device; a presence of an inhalant, metabolite, or other marker thereof in a subject's blood; or other such indications of an inhalant dispensed as described herein). This can occur, for example, in a context in which administration detection logic 2140 or other detection modules (receiver 831 or monitoring module 1101, e.g.) perform one or more operation(s) of 10-16.

Operation 2813 describes obtaining an indication of when at least a portion of a vessel moved (e.g. one or more modules for recording when a vessel moved 2145 detecting or receiving timing data 538, 539 indicating a series of instances when a vessel 160, 1010, 1190 containing a bioactive or other therapeutic material moved as an indication that the therapeutic material was or was not taken pursuant to one or more regimens 2001-2004). If the regimen required that the therapeutic material be taken with a frequency F but timing data 539 indicates that the vessel was opened or moved less frequently than 0.9×F, for example, such a negative indication 689 may justify a regimen noncompliance determination 688 or negate a regimen compliance determination 686 that would otherwise occur. Suitable logic may include or be configured to respond to accelerometers or any of numerous other suitable implementation circuitry affixed to or otherwise supported by the vessel that can readily be implemented in light of teachings herein. Alternatively or additionally, such logic may implement one or more distillation criteria 621, such as with software or circuitry for comparing a first image of a visual field with a second image of the visual field (in successive images 633, 634 or a time-lapse video clip 644 of or from the vessel, e.g.) or by causing other distillation modules 430 described herein to be invoked. In some variants, moreover, operation 2813 may include or be configured to respond to circuitry for detecting an actuation (of a valve, cap, cover 1181, or other portion of the vessel, e.g.).

Operation 2816 describes obtaining an indication whether a vessel has been ingested (e.g. one or more modules for obtaining a wireless indication whether a vessel has been ingested 2143 detecting a current measurement 554 or other indication of ingestion 445 pertaining to a capsule 910, 1153 or vessel 160, 1010, 1210 as described herein). This can occur, for example, in a context in which such a vessel has one or more immersion-responsive structures 905, mucosal material sensors 1221, pH sensors 1225, auditory data distillation modules 431 configured to detect a swallowing sound 441, or other such detection features 1185 configured to detect one or more of (a) a temperature about equal to that of a living body; (b) a pH about equal to that of stomach acid; (c) a pH increase indicative of travel through a small intestine and of earlier ingestion; (d) auditory or optical indicia of ingestion; (e) mucous or mucosa characteristic of an intestine; or (f) an ambient pressure, electrical conductivity, or other device-detectable characteristic of immersion in stool or other bodily fluids.

In light of teachings herein, numerous existing techniques may be applied for configuring special-purpose circuitry or other structures effective for detecting that something has been ingested as described herein without undue experimentation. See, e.g., U.S. Pat. No. 7,504,954 ("Radio frequency identification pharmaceutical tracking system and method"); U.S. Pat. No. 7,437,195 ("Regulation of eating habits"); U.S. Pat. No. 7,427,266 ("Method and apparatus for verification of ingestion"); U.S. Pat. No. 7,414,534 ("Method and apparatus for monitoring ingestion of medications using an implantable medical device"); U.S. Pat. No. 7,382,263 ("Oral drug compliance monitoring using radio frequency identification tags"); U.S. Pat. No. 7,141,016 ("Systems and methods for monitoring gastrointestinal system"); U.S. Pat. No. 7,118,531 ("Ingestible medical payload carrying capsule with wireless communication"); U.S. Pat. No. 7,062,312 ("Combination and method including a visual marker for determining compliance with a medication regimen"); U.S. Pat. No. 6,663,846 ("Devices and methods for monitoring drug therapy compliance"); U.S. Pat. No. 6,136,801 ("Therapeutic agent with quantitative consumption marker").

Operation 2817 describes obtaining a test result of a sample extracted from an individual (e.g. one or more modules for obtaining a test result of a sample extracted from an individual 2147 detecting an analyte of a therapeutic material or other regimen compliance indication in a bodily fluid, hair, or other sample extracted from subject 382). This can occur, for example, in a context in which such a module (including or otherwise in communication with a sample tester 119 having one or more sensors 2169, e.g.) can generate a positive indication 687 indicative of compliance, a normalcy indication 2471, a noncompliance indication 2473, or other such go/no-go determinants 2474 or determinations as a result of applying one or more a priori thresholds 565 indicative of a marker or other material component 534 of the therapeutic material in a blood or other extracted sample 2165 in a specified concentration (sufficient to indicate normalcy or regimen compliance, e.g.). In some contexts, for example, administration detection logic 2140 or other detection modules as described herein may be configured to perform one or more operation(s) of 10-16. Alternatively or additionally, a dispenser V37V, capsule 910, 1153 or other such device 860 may be configured to facilitate such operations by performing operation 2817.

In light of teachings herein, numerous existing techniques may be applied for configuring special-purpose circuitry or other structures effective for measuring health-indicative or other relevant physical properties from a sample extracted from an individual as described herein without undue experimentation. See, e.g., U.S. patent application Ser. No. 11/343,944 ("Establishing a Biological Recording Timeline by Artificial Marking") and U.S. patent application Ser. No. 11/343,966 ("Using a Biological Recording to Obtain Time Values"). See also U.S. Pat. No. 7,491,493 ("Method and kit for molecular identification of smallpox"); U.S. Pat. No. 7,485,472 ("Simple method for quantitative measuring the adhesion of platelets ex vivo"); U.S. Pat. No. 7,480,032 ("Device and method for in vitro determination of analyte concentrations within body fluids"); U.S. Pat. No. 7,455,973 ("Methods and compositions for the detection of cervical disease"); U.S. Pat. No. 7,356,364 ("Device for optical monitoring of constituent in tissue or body fluid sample using wavelength modulation spectroscopy, such as for blood glucose levels"); U.S. Pat. No. 7,257,365 ("Serum biomarkers of Hepatitis B Virus infected liver and methods for detection thereof"); U.S. Pat. No. 7,063,782 ("Electrochemical detection of ischemia"); U.S. Pat. No. 6,989,891 ("Device and method for in vitro determination of analyte concentrations within body fluids"); U.S. Pat. No. 6,884,223 ("Method for detecting .alpha.-oxoaldehydes in the whole blood, blood plasma and/or serum of a patient"); U.S. Pat. No. 6,750,053 ("Apparatus and method for assaying coagulation in fluid samples"); U.S. Pat. No. 6,718,007 ("Using hair to screen for breast cancer"); U.S. Pat. No. 6,623,972 ("Automated method for detecting, quantifying and monitoring exogenous hemoglobin in whole blood, plasma and serum").

With reference again to flow 2800 of FIG. 28 and to other flows described above, one or more operations of 21-26 may each (optionally) include or relate to one or more instances of operation 2891, operation 2894, operation 2895, operation 2898, or operation 2899 as described below. Such a "utility" operation may be carried out, for example, by application or decision logic (implemented in one or more primary components 221-226 or distillation units 460 or other data handling units responsive to one or more preparatory operations, e.g.) configured to implement or communicate one or more outputs of 251-256 or other useful results described herein.

Operation 2891 describes transmitting a regimen compliance determination as an actuation signal (e.g. output device 176 transmitting a signal 2054 manifesting a regimen compliance determination 686 via a wireless linkage 2243 or mechanical linkage 2244 configured to control a switch 145 or other mechanical component 130). This can occur, for example, in a context in which one or more components 221-226 signals such a determination 447 (as an indication of ingestion 445 or other data distillation 450, e.g.) that triggers signal 2054 that causes a door 131 to open or a motor 133 to turn on and in which such mechanical component(s) would otherwise not move. Alternatively or additionally, output device 176 may manifest a compliance-negative indication 689 by disabling one or more control elements 140 (that control an automobile or other motor 133, e.g.).

Operation 2894 describes obtaining an indication of an abnormally late order for a therapeutic component (e.g. one or more modules for obtaining an indication of a medical expense signaling an apparent noncompliance 2186 receiving a pointer 677 to a transaction history or other such data 651 indicating that a material provider 381 or other individual has not been ordering a requisite quantity of a therapeutic component fast enough to permit compliance with a regimen). This can occur, for example, in a context in which the indication is a natural language expression (such as "noncompliant" or "indeterminate") and in which such modules are implemented in one or more control modules 880, 1220 or other modules that perform one or more operation(s) of 21-26. Raw data, scalar, logical, or other indications may likewise be obtained, however, such as in a context in which such orders are nominally sufficient to provide P treatments for Q individuals (participating in a nutraceutical regimen, e.g.) for a given period of weeks but in which supplies for fewer than P×Q/2 treatments have been ordered before or during that period of weeks, warranting an inference that at least one such individual has apparently not received one or more requisite treatments of a prescribed regimen within one or more acceptable time intervals.

Operation 2895 describes determining whether an event occurred within a normal interval of time (e.g. one or more modules for evaluating timeliness of an event 2146 causing a comparison of one or more temporal indications 572 of a device-detectable event against one or more normalcy-indicative thresholds 563). This can occur, for example, in a context in which the "event" is an order placement or an image capture or a detection of another specific signal as described herein; in which one or more detection modules 915 generate a pass/fail indication 573 as a result of applying one or more timing thresholds to a timestamp of the event; in which technician 361 specifies such thresholds 563, indications 572, and correspondences (many-to-one or one-to-many or one-to-one, e.g.); and in which one or more sensors 833, 932, 1228, 2169, 2171 or other signal sources provide such timestamps or other temporal indications.

In light of teachings herein, numerous existing techniques may be applied for configuring special-purpose circuitry or other structures effective for determining and recording whether events are happening within a defined interval of time as described herein without undue experimentation. See, e.g., U.S. Pat. No. 7,369,476 ("Device for reading from or writing to optical recording media having a control unit for a data slicer"); U.S. Pat. No. 7,335,106 ("Closed-loop system for displaying promotional events and granting awards for electronic video games"); U.S. Pat. No. 7,330,101 ("Prescription compliance device and method of using device"); U.S. Pat. No. 7,293,645 ("Method for monitoring hand hygiene compliance"); U.S. Pat. No. 7,287,031 ("Computer system and method for increasing patients compliance to medical care instructions"); U.S. Pat. No. 7,271,728 ("Method for assessing improvement in hand hygiene practices"); U.S. Pat. No. 7,170,823 ("Medical dispenser, a blister card for use in the dispenser and a method of dispensing medical doses"); U.S. Pat. No. 6,973,371 ("Unit dose compliance monitoring and reporting device and system"); U.S. Pat. No. 6,882,278 ("Apparatus and methods for monitoring compliance with recommended hand-washing practices"); U.S. Pat. No. 6,655,583 ("Medical billing method and system"); U.S. Pat. No. 6,375,038 ("Dispenser having timing means, multisensory output and means of tracking usage number"); U.S. Pat. No. 6,371,931 ("Reflex tester and method for measurement of range of motion and peripheral vision"); U.S. Pat. No. 6,198,695 ("Event monitoring device"); U.S. Pat. No. 6,198,383 ("Prescription compliance device and method of using device").

Operation 2898 describes causing wireless signal transmission circuitry in situ to initiate a wireless transmission in response to an indication of ingestion (e.g. acid-activated sensor 2164 responding to an ambient pH going below an a priori threshold 565 by triggering a transmission of RF energy 2168 from an ingestible instance of event/detection unit 2150). This can occur, for example, in a context in which the a priori threshold 565 is between 2 and 6, in which the intended subject is a person, and in which product 2410 includes the event/detection unit 2150. Alternatively or additionally, one or more implants 1340 or other vessels 1010 (situated in or near the digestive tract of subject 382, e.g.) may be configured to perform operation 2898 by transmitting a wireless signal 1034 in response to a detection of an ingestible capsule 491, 910 in the digestive tract.

Operation 2899 describes obtaining an indication of whether an individual remains enrolled in a program requiring a therapeutic regimen (e.g. one or more modules for verifying that a therapeutic regimen remains in effect for an individual 2189 determining whether a provider has confirmed that a subject 382 remains enrolled in a program after having sent a request for such confirmation to the provider). This can occur, for example, in a context in which the provider has been given ample opportunity and incentive for replying (by following a "confirm enrollment" link in an electronic message identifying the program and the individual, e.g.). Alternatively or additionally, in some variants, one or more incentives to the subject(s) may depend upon whether such continued enrollment is confirmed.

In some variants, detection logic (units or modules, e.g.) described herein may include one or more cameras 2232, microphones, or other sensors 179, 187 configured to capture or otherwise obtain a video clip 642, an audio clip 643, one or more representative samplings 671, 672 thereof, or other such components of records 488. Such records may include an indication of ingestion 440 or other objective indication of a bioactive or other therapeutic material 184 administered to a portion of a subject 382, such as a video clip of a care provider 383 administering a topical treatment. This can occur, for example, in a context in which the therapeutic material comprises a targeted drug or other topical bioactive material that is not well suited for the individual to use as a systemic treatment, in which such data is consistently available for review (stored in an archive, e.g.) as an objective indication that the material has been administered to a specific portion of the individual, in which such records are not generally reviewed, and in which an underwriter or other service provider 310 can authorize a type of benefit, coverage, or other service to a class of individuals conditionally in response to such records being generally available. Such classes may be defined by one or more preferences or demographic attributes 750, for example. Such records may also include an indication of a health status apparently resulting from a bioactive material administered to the individual, such as a biometric measurement (indicating an increase in temperature, e.g.) or an image comparison (indicating a skin color change or other expected improvement after a regimen over a course of days or months that includes topical or systemic steroid treatments, e.g.).

With reference now to flow 2900 of FIG. 29 and to other flows described above, one or more operations of 10-16 may each (optionally) include or relate to one or more instances of operation 2911 or operation 2913 as described below. Such a "preparatory" operation may be carried out, for example, by one or more distillation units or other detection logic (implemented in one or more application modules 110 or components 210-216 or interaction units 375, e.g.) configured to invoke, modulate, or otherwise influence one or more other components described herein.

Operation 2911 describes detecting whether data from one or more sensors indicate an actuation of a portion of a dispensing device (e.g. one or more modules for detecting an actuation in a vessel 2141 receiving, from one or more processors 2272, an actuation signal 2241 that is also used to control an actuation of one or more plungers 1182, rotary elements, or other actuators 1052, 1184 of a syringe 1155, vending machine, inhaler 1158, implant, or other medication dispenser). This can occur, for example, in a context in which processor 2272 triggers such actuation as a response to data 2161 from one or more sensors 2169 indicating that subject 382 needs such a dispensation (from a sample 2165 of blood from subject 382 indicating a deficiency of a therapeutic component 181, e.g.). Alternatively or additionally, one or more actuation sensors 2242 can be configured to generate such data 2161 as a direct indication 2295 of such actuation. This can occur, for example, in a context in which image recognition module 2258 recognizes image data 424 depicting an actuator 1184 in different positions (relative to a remainder of vessel 1190, e.g.) or in which vessel 1190 includes an actuation sensor 2242 mechanically coupled with actuator 1052, and in which primary unit 1110 or vessel 1190 contains administration detection logic 2140 that performs one or more operation(s) of 10-16.

In light of teachings herein, numerous existing techniques may be applied for configuring special-purpose circuitry or other structures effective for detecting actuation of a portion of a vessel as described herein without undue experimentation. See, e.g., U.S. Pat. No. 7,480,543 ("Ultrasonic sensor for detecting the dispensing of a product"); U.S. Pat. No. 7,442,180 ("Apparatus and methods for administering bioactive compositions"); U.S. Pat. No. 7,396,511 ("Dispensing device, dispensing method and method of detecting defective discharge of solution containing biological sample"); U.S. Pat. No. 7,347,200 ("Medicament dispenser"); U.S. Pat. No. 7,299,944 ("Fluid dispenser calibration system and method"); U.S. Pat. No. 7,269,476 ("Smart medicine container"); U.S. Pat. No. 7,233,015 ("System and method for detecting liquid flow from a nozzle in a semiconductor processing device"); U.S. Pat. No. 7,170,823 ("Medical dispenser, a blister card for use in the dispenser and a method of dispensing medical doses"); U.S. Pat. No. 7,117,653 ("Flavoring system and method"); U.S. Pat. No. 7,086,269 ("Apparatus and method for testing seed singulation of a seed meter"); U.S. Pat. No. 7,027,935 ("Sample dispensing apparatus and automatic analyzer using the same"); U.S. Pat. No. 6,998,230 ("Array fabrication with drop detection").

Operation 2913 describes receiving a wireless signal via a device in external contact with a portion of an individual from within the portion of the individual (e.g. wireless receiver 2176 receiving one or more wireless signals as described herein via a handheld instrument 1350, belt, watch, headset, skin-adhesive patch 163, or other body contact device 2175 from within a digestive tract or other portion 1115 of a subject 382, 912, 1112, 1282 as described herein). This can occur, for example, in a context in which a detection module 162, sensor 1229, or other logic in the device performs one or more operation(s) of 10-16; in which the device is held in the subject's hand or affixed to the subject 382 (on the subject's skin 1326, e.g.); and in which an implanted or ingested item transmitted a wireless signal 1034, 1230 (a digital message, e.g.).

In light of teachings herein, numerous existing techniques may be applied for configuring structures effective for positioning a device in external contact with a subject as described herein without undue experimentation. See, e.g., U.S. Pat. No. 7,951,080 ("On-body medical device securement"); U.S. Pat. No. 7,976,480 ("Wearable auscultation system and method"); U.S. Pat. No. 7,942,827 ("Minimally invasive allergy testing system"); U.S. Pat. No. 7,744,640 ("Thermal treatment garment and method of thermally treating body portions"); U.S. Pat. No. 7,697,966 ("Noninvasive targeting system method and apparatus"); U.S. Pat. No. 7,625,117 ("Bandage with sensors"); U.S. Pat. No. 7,507,207 ("Portable biological information monitor apparatus and information management apparatus"); U.S. Pat. No. 7,378,975 ("Method and apparatus for mitigating the risk of pressure sores"); U.S. Pat. No. 7,319,639 ("Acoustic concealed item detector"); U.S. Pat. No. 7,674,231 ("Wearable pulse wave velocity blood pressure sensor and methods of calibration thereof"); U.S. Pat. No. 7,869,853 ("Analyte monitoring device and methods of use").

With reference again to flow 2900 of FIG. 29 and to other flows described above, one or more operations of 21-26 may each (optionally) include or relate to one or more instances of operation 2992, operation 2995, operation 2997, or operation 2998 as described below. Such a "utility" operation may be carried out, for example, by application or decision logic (implemented in one or more primary components 221-226 or distillation units 460 or other data handling units responsive to one or more preparatory operations, e.g.) configured to implement or communicate one or more outputs of 251-256 or other useful results described herein.

Operation 2992 describes signaling a regimen compliance data distillation by identifying a data distillation protocol (e.g. one or more processors 470 executing or otherwise invoking a special-purpose filter 471 such as a module for determining whether one or more components of raw data 410 are too large by applying one or more size thresholds 564). This can occur, for example, in a context in which a sender or recipient of record 488 recognizes that one or more components of raw data 410 may be unsuitably large for archiving or transmission; in which one or more instances of distillation modules 430 perform one or more operation(s) of 21-26; in which technician 361 has configured filter 471 to recognize at least some data 425 as being compatible with significant digital compression (lossy image compression or non-uniform sampling and interpolation, e.g.); and in which technician 361 recognizes a need to implement a data distillation protocol 658 combining a maximum size threshold 562 (imposed upon one or more instances of record 488 containing too-voluminous raw data 410, e.g.) even while usually leaving a remainder of the components of raw data 410 intact. Alternatively or additionally, such data distillation protocols may be used (by one or more processors 470, e.g.) to generate data distillations 450 indicative of regimen compliance or noncompliance as described herein.

In light of teachings herein, numerous existing techniques may be applied for configuring special-purpose circuitry or other structures effective for implementing and delegating data distillation tasks as described herein without undue experimentation. See, e.g., U.S. Pat. No. 7,991,628 ("Generating output data based on patient monitoring"); U.S. Pat. No. 7,987,720 ("Ultrasonic sensing array system and method"); U.S. Pat. No. 7,967,759 ("Endoscopic system with integrated patient respiratory status indicator"); U.S. Pat. No. 7,957,781 ("Method and circuit for storing and providing historical physiological data"); U.S. Pat. No. 6,539,101 ("Method for identity verification"); U.S. Pat. No. 7,983,817 ("Method and arrangement for obtaining information about vehicle occupants"); U.S. Pat. No. 7,920,907 ("Analyte monitoring system and method"); U.S. Pat. No. 7,494,470 ("Analysis of metabolic gases by an implantable cardiac device for the assessment of cardiac output"); U.S. Pat. No. 7,220,240 ("System and method for adaptive drug delivery"); U.S. Pat. No. 6,416,471 ("Portable remote patient telemonitoring system"); U.S. Pat. No. 7,564,990 ("Imaging system and method for physical feature analysis"); U.S. Pat. No. 7,840,269 ("Analysis of eating habits"); U.S. Pat. No. 7,747,454 ("System and method for real time management of a drug regimen"); U.S. Pat. No. 7,970,470 ("Diagnosis and/or therapy using blood chemistry/expired gas parameter analysis"); U.S. Pat. No. 7,783,442 ("System and methods for calibrating physiological characteristic sensors"); U.S. Pat. No. 7,890,295 ("Real time self-adjusting calibration algorithm").

In some variants, for example, one or more distillation modules 430 may perform operation 2992 in performing a triage operation. In a context in which distillation module 434 is unable to determine automatically whether sequential image data 424 contains an indication of ingestion 445, for example, or in which distillation module 435 is unable to resolve a presence/absence of some event indication 440 in sensor output or other raw data 426, such distillation modules may (optionally) be configured to respond to such indeterminacy by implementing a contingent evaluation request protocol 482 such as by transmitting a message 483 to a technician 361 (via response unit 355, e.g.) tasked with resolving such indeterminacy. Such an invocation may likewise include transmitting the relevant image data 424 or other raw data 410 (with pointer data 444 signaling the time or location of anomalous data with human-executable instructions 478, e.g.) and a time after which a description of the anomalous data will be finalized (as "unresolved," e.g.). In some contexts, for example, such instructions may identify a type of review (a category designation or detailed analysis, e.g.) for a human analyst to apply. This can occur, for example, in a context in which a technician 361 who receives the message 483 has proprietary or other noteworthy skills or tools (one or more specialized distillation modules 436 in a remote instance of response unit 355, for example, suitable for cost-effective implementation as an emergency call center or other specialty service). In some contexts, for example, a government or other service provider 310 who suspects that widespread noncompliance with a legally imposed regimen (forbidding a use of a controlled substance, e.g.) is occurring in a population of subjects who share one or more common demographic attributes 750 (having an area code 753 of "303" or a vehicle registration address in Denver County, e.g.) may provide specific human-readable instructions 478 selectively (in an automatic conditional alert message 483 to an investigator or consultant, e.g.) and optionally articulating qualitative or novel criteria 624 (for investigating some class of program participants' compliance-indicative data for suspicious circumstances, e.g.). Alternatively or additionally, such instructions 478 may be useful in a context in which no available device can readily apply one or more criteria as described herein to images 632 or other raw data 410 and in which a remote application of compliance-related criteria would be more effective for programmatic human review (by a marketing specialist or other technician 361, e.g.) than for a fully automated implementation.

Operation 2995 describes signaling a regimen compliance data distillation by transmitting the regimen compliance data distillation (e.g. processor 470 executing a systematic archiving protocol 485 implemented as a sequence of instructions for transmitting a compliance determination 447, an at-least-generally negative indication 689 of compliance, a link or other pointer 679 to one or more components of raw data 410 of potential relevance to a future determination of regimen compliance or noncompliance, or some other data distillation across network 340 to a remote delivery unit 325 suitable for archiving). This can occur, for example, in a context in which such raw data components include one or more measurements 665 or auditory data 653 indicating that a capsule was apparently not ingested (and was instead flushed or left in a bottle, e.g.); in which such systematic archiving protocol 485 includes one or more instructions 478 executable by processor 470; in which a portion of raw data 410 is included as a part of the data distillation 450; and in which a control module 115, 880, 1220 implements a distillation or other data handling unit 610 as described below.

In light of teachings herein, numerous existing techniques may be applied for configuring special-purpose circuitry or other structures effective for transmitting therapeutic compliance information remotely across a communication medium as described herein without undue experimentation. See, e.g., U.S. Pat. No. 7,504,954 ("Radio frequency identification pharmaceutical tracking system and method"); U.S. Pat. No. 7,395,214 ("Apparatus, device and method for prescribing, administering and monitoring a treatment regimen for a patient"); U.S. Pat. No. 7,375,640 ("System, method and implementation for increasing a likelihood of improved hand hygiene in a desirably sanitary environment"); U.S. Pat. No. 7,369,919 ("Medication adherence system"); U.S. Pat. No. 7,295,890 ("Prescription drug compliance monitoring system"); U.S. Pat. No. 7,086,399 ("Apparatus for delivery of humidified gases therapy, associated methods and analysis tools"); U.S. Pat. No. 6,980,958 ("Apparatus and methods for monitoring and modifying anticoagulation therapy of remotely located patients"); U.S. Pat. No. 6,973,371 ("Unit dose compliance monitoring and reporting device and system").

Operation 2997 describes obtaining a regimen compliance data distillation by causing an application of one or more auditory data distillation criteria (e.g. auditory data distillation module 431 and systematic archiving protocol 485 jointly cropping a silent interval or other conspicuously irrelevant portion from auditory data 421 in record 488). This can occur, for example, in a context in which one or more sensors in, on, or near a regimen subscriber or other subject 382, 912, 1282, 1112 detect raw auditory data 421; in which auditory data distillation module 431 preferentially retains a frequency-domain portion of the data near a human vocal range (between 30 and 300 Hertz, e.g.) or a portion in temporal proximity to a recognizable swallowing sound 441 in the auditory data 421; in which a plurality of distillation modules 430 jointly perform one or more operation(s) of 21-26; and in which some of the output from auditory data distillation module 431 is routed through circuitry implementing systematic archiving protocol 485. Alternatively or additionally, auditory data distillation module 431 may be configured as a software program for speech recognition that selectively removes time intervals of recognizable speech as auditory data 421 passes to become a part of record 488.

Operation 2998 describes obtaining a regimen compliance data distillation by causing an application of one or more sensor measurement thresholds (e.g. measurement data distillation module 432 generating a regimen compliance determination 686 or other generally positive indication 687 if temperature sensor data 422, for several sequential thermal transitions 442 sampled each several seconds, indicates a temperature monotonically approaching 37° C. so as to indicate close and constant proximity with a human body). This can occur, for example, in a context in which one or more reliable indications of an ingestion or application of a sensor-bearing device (in the form of a capsule, patch, or other material administration product 150 as described herein, e.g.) signifies regimen compliance; and in which processor 655 executes or otherwise invokes one or more distillation modules 430 to perform one or more operation(s) of 21-26. Alternatively or additionally, an invocation module 780 may (optionally) perform operation 2996 by triggering a measurement data distillation module 432 (remotely across network 340, e.g.) configured to apply one or more other thresholds 562 (by passing one or more prolixity determinants 760, protocol identifiers 774, or other such parameters 777, e.g.). This can occur, for example, in a context (1) in which a distillation unit 460 or interaction unit 375 includes or otherwise couples with linking module 790 that includes a control module 880, 1220 or other module configured to perform one or more operation(s) of 21-26, (2) in which service provider 310 has deemed one or more such comparative evaluation criteria 613 sufficient to establish a positive indication 687 relating to regimen compliance; and (3) in which a distillation module 432 responds to such invocation by performing another instance of operation 2996. In some variants, moreover, data handling unit 610 may be configured to provide a help function or other supplemental guidance 2297 associating a qualifiedly positive indication 687 of regimen compliance or a qualifiedly negative indication 682 (signifying a trend toward or other foreseeability of regimen noncompliance, e.g.).

With reference now to flow 3000 of FIG. 30 and to other flows described above, one or more operations of 10-16 may each (optionally) include or relate to one or more instances of operation 3012, operation 3014, or operation 3018 as described below. Such a "preparatory" operation may be carried out, for example, by one or more distillation units or other detection logic (implemented in one or more application modules 110 or components 210-216 or interaction units 375, e.g.) configured to invoke, modulate, or otherwise influence one or more other components described herein.

Operation 3012 describes retrieving event data relating to an individual (e.g. one or more inquiry modules 2223 requesting a direct event indication 440, timing data 537 or other event-indicative data 2162 that a database 2181 associates with a subscriber number, patient name and birthdate, or other one or more parameters 777 effective for identifying a subject 382, 912, 1082, 1112). This can occur, for example, in a context in which one or more detection devices, processors 115, 470, or other components 210-216 are configured to perform one or more operations 10-16 as described above, and in which response module 2250 includes such inquiry module(s) and invokes it/them with one or more such parameters 777. In some variants, for example, one or more implementation outputs 251-256 may include a response to such retrieval (or lack thereof) from a remote source (server 294, e.g.). Alternatively or additionally, operations (21-26) as described herein may respond directly to indications of ingestion 445, 2445 or inhalation or other such regimen-specific event indications 571-573 that may be associated with an individual.

In light of teachings herein, numerous existing techniques may be applied for configuring special-purpose circuitry or other structures effective for requesting or otherwise receiving demographic attributes, event data, or other data via an interface about patients or other subjects as described herein without undue experimentation. See, e.g., U.S. Pat. No. 7,258,666 ("System and methods for monitoring a patient's heart condition"); U.S. Pat. No. 6,968,375 ("Networked system for interactive communication and remote monitoring of individuals"); U.S. Pat. No. 6,926,668 ("System and method for analyzing normalized patient voice feedback in an automated collection and analysis patient care system"); U.S. Pat. No. 6,893,396 ("Wireless internet bio-telemetry monitoring system and interface"); U.S. Pat. No. 6,755,783 ("Apparatus and method for two-way communication in a device for monitoring and communicating wellness parameters of ambulatory patients"); U.S. Pat. No. 6,478,737 ("System and method for analyzing normalized patient voice feedback an automated collection and analysis patient care system"); U.S. Pat. No. 6,168,563 ("Remote health monitoring and maintenance system").

Operation 3014 describes indicating a data distillation protocol at least partly based on a demographic attribute of a subpopulation (e.g. one or more inquiry modules 2224 nominating one or more distillation modules 430 via response unit 355 for a technician 361 or agent 362 to confirm or select among, the nomination depending upon an age 751, ethnicity 752, or area code 753 effectively identifying a group of people that includes a particular subject 382 of interest). This can occur, for example, in a context in which server 294 has a medical history or service directory associating the individual with the demographic attribute(s), in which service provider 310 has specified a protocol 512 for monitoring or data distillation (for heightened scrutiny, e.g.) that depends upon such demographic attributes 750, and in which response module 2250 has authorized access to a private data resource (a medical history of subject 382, e.g.) or other access to a public data resource (a service directory listing subject 382, e.g.). Alternatively or additionally, inquiry module 2224 may perform operation 3014 by transmitting an audible, text, or other message 483 to a material provider 381 or subject 382, for example, configuring interaction unit 375 for use by subject 382 to include one or more implementations 201-206 as described herein. In some contexts, inquiry module 2224 may be configured to request other human input (by conferencing in or texting a translator or other agent 362, e.g.) as a conditional response to indeterminate input (speech or text not understood by the device, e.g.) for gathering data about subject 382 (via a bot, e.g.) upon which a configuration of interaction unit 375 depends. Alternatively or additionally, a regimen compliance status or other data distillation 450 may be obtained by applying one or more default criteria or default distillation modules 430 (invoked as a preliminary result or in the event of a lack of response to such inquiry, e.g.) as described herein.

Operation 3018 describes transmitting an inquiry to an individual (e.g. one or more inquiry modules 2225 transmitting audible or text data 231, 233, 235, 237, 239, 241 via an output device 276 to a service provider 310, care provider 382, or other recipient 322). This can occur, for example, in a context in which the inquiry concerns a subject's preferences 2221 or other attributes 2222 that are not readily available; in which service provider 310 has specified a regimen that includes an expressed dependence upon such attribute(s); in which response module 2250 is implemented in one or more control units 305, delivery units 325, or interaction units 375; and in which service provider 310 would not otherwise be able to equip a regimen with such contingent features via control unit 305. In some variants it may be convenient for an executive with a large client list to provide each client with an interaction unit 375 or other interface 270 each configured to ask the client (subject 382, e.g.) whether a regimen 781, 782 should be adjusted, for example, in response to one or more negative indications 689 (indicative of noncompliance, e.g.). In some variants inquiry module 2225 may provide a default response if no data 425 from a corresponding input device 178, 278 or otherwise from the individual is recognized within a prescribed interval (a few seconds, minutes, or hours, e.g.). Moreover inquiry module 2225 may be configured to perform operation 3018 again in response to some clients' responsive inputs (expressing a quizzical tone of voice or other device-detectable manifestation of a client inquiry, e.g.), such as by transmitting a query or problem report (audio clip 641 of the client, e.g.) to a call center or other agent 362.

Operation 3091 describes determining whether an individual is apparently compliant with a regimen targeting a portion of the individual (e.g. one or more logic modules 510 implementing an evaluation protocol 511 pursuant to a regimen 782 targeting a disorder of a digestive tract of a given subject 382). This can occur, for example, in a context in which a doctor or other service provider 310 has initially defined the regimen 782 (by recommending a nutraceutical or pharmaceutical effective for treating acid reflux with a dosage and frequency, e.g.) that is later enhanced (by technician 361 or configuration module 795, e.g.) by the inclusion of a monitoring or evaluation protocol 511. Alternatively or additionally, such a regimen may include one or more of an antiviral material component 522 or other antibiotic material component, a nitric-oxide-donor material component 525, an antihypertensive material component 531, a statin-containing material component 532, or other material components 534. In some variants, moreover, regimen 782 may be configured to include a daily monitoring component 796 that tracks whether one or more prescribed dosages were apparently (ingested or otherwise) administered daily. In some contexts, such timing data 537, 538 (even alone) can be useful (to a doctor or other care provider 383, e.g.) to inform further diagnoses or recommendations.

In light of teachings herein, numerous existing techniques may be applied for configuring special-purpose circuitry or other structures effective for using measurement data to determine compliance with medicinal or other programs targeting "a portion of" an individual as described herein without undue experimentation. See, e.g., U.S. Pat. No. 7,504,954 ("Radio frequency identification pharmaceutical tracking system and method"); U.S. Pat. No. 7,395,214 ("Apparatus, device and method for prescribing, administering and monitoring a treatment regimen for a patient"); U.S. Pat. No. 7,375,640 ("System, method and implementation for increasing a likelihood of improved hand hygiene in a desirably sanitary environment"); U.S. Pat. No. 7,369,919 ("Medication adherence system"); U.S. Pat. No. 7,295,890 ("Prescription drug compliance monitoring system"); U.S. Pat. No. 7,166,063 ("Brace compliance monitor"); U.S. Pat. No. 7,086,399 ("Apparatus for delivery of humidified gases therapy, associated methods and analysis tools"); U.S. Pat. No. 6,980,958 ("Apparatus and methods for monitoring and modifying anticoagulation therapy of remotely located patients"); U.S. Pat. No. 6,973,371 ("Unit dose compliance monitoring and reporting device and system"); U.S. Pat. No. 6,926,667 ("Patient compliance monitor"); U.S. Pat. No. 6,645,142 ("Glucose monitoring instrument having network connectivity"); U.S. Pat. No. 6,494,579 ("Eye self-test device"); U.S. Pat. No. 6,151,586 ("Computerized reward system for encouraging participation in a health management program").

Operation 3095 describes determining whether a therapy is apparently having a specific effect (e.g. one or more image recognition modules 2258 comparing successive images 143, 144 of a body part of subject 382 to determine whether the later image 144 indicates an improvement (reduced inflammation or rash, e.g.). This can occur, for example, in a context in which a specialist or other service provider 310 configures an interface 189 to define a threshold 771 or other filter 472 to designate the specific effect (improvement, e.g.) toward which a therapeutic or observation regimen is targeted. Alternatively or additionally, the service provider 310 may include human-executable instructions 478 in the regimen, by which a technician 361 will generate pointer data 444 or other summary data 446 that a specialist can later validate. This can occur, for example, in a context in which a parent or other care provider 383 near subject 382 is not trained to understand such specific instructive content 475 and in which such specialized monitoring would therefore be impractical.

In light of teachings herein, numerous existing techniques may be applied for configuring special-purpose circuitry or other structures effective for implementing a measurement criterion or other determination indicative of whether a bioactive material or other therapy is apparently having any effect. See, e.g., U.S. Pat. No. 7,185,650 ("Systems and methods for determining a minimum effective dose of an inhaled drug for an individual patient at a given time"); U.S. Pat. No. 7,138,240 ("Methods of assaying receptor activity"); U.S. Pat. No. 7,003,346 ("Method for illness and disease determination and management"); U.S. Pat. No. 6,942,619 ("Ultrasound radiation device"); U.S. Pat. No. 6,881,192 ("Measurement of sleep apnea duration and evaluation of response therapies using duration metrics"); U.S. Pat. No. 6,659,959 ("Catheter with physiological sensor"); U.S. Pat. No. 6,613,573 ("Method and apparatus for monitoring anti-platelet agents"); U.S. Pat. No. 6,581,607 ("Method and system for use in treating a patient with a biological substance to optimize therapy and prevent an adverse response"); U.S. Pat. No. 6,581,606 ("Method, apparatus and system for use in treating patient with a drug having an antineoplastic effect to optimize therapy and prevent an adverse drug response"); U.S. Pat. No. 6,575,169 ("Method and apparatus for use in treating a patient with any drug to optimize therapy and prevent an adverse drug"); U.S. Pat. No. 6,347,239 ("Method of evaluating the efficacy of drug on brain nerve cells"); U.S. Pat. No. 6,329,153 ("Method for evaluating immunosuppressive regimens"); U.S. Pat. No. 6,007,986 ("Methods for anti-addictive narcotic analgesic activity screening").

Operation 3096 describes applying a provider-specified criterion to device-detectable health-indicative data (e.g. a processor 655 or hardware-implemented distillation protocol 657 applying one or more evaluation criteria 614 or other distillation criteria 621 defined by a service provider 310 or material provider 381 to chemical sensor data 423 or other raw data 410). This can occur, for example, in a context in which such sensor data includes a pH or concentration measurement deemed acceptable (by chemical data distillation module 433, e.g.) if it falls inside of a threshold 771 minimum or maximum specified by the provider. Alternatively or additionally, periodic samplings 674 or therapeutic event pointers 678 may be compliant if they are sufficiently frequent (having a frequency higher than a threshold 771 of a provider-specified monitoring regimen, e.g.).

In light of teachings herein, numerous existing techniques may be applied for configuring special-purpose circuitry or other structures effective for applying various provider-specified criteria (relating to counts or dosages provided by a physician or other service provider 310, e.g.) to device-detectable health-indicative data (for determining success, eligibility, or some other threshold event, e.g.) as described herein without undue experimentation. See, e.g., U.S. Pat. No. 7,488,291 ("Methods for detecting and monitoring sleep disordered breathing using an implantable medical device"); U.S. Pat. No. 7,487,774 ("Adaptive patient trigger threshold detection"); U.S. Pat. No. 7,465,551 ("Method of determining cytokine dosage for improving myelosuppressive state"); U.S. Pat. No. 7,366,571 ("Neurostimulator with activation based on changes in body temperature"); U.S. Pat. No. 7,246,619 ("Snore detecting method and apparatus"); U.S. Pat. No. 7,223,246 ("Diagnosis of the presence of cochlear hydrops using observed auditory brainstem responses"); U.S. Pat. No.

7,177,684 ("Activity monitor and six-minute walk test for depression and CHF patients"); U.S. Pat. No. 7,132,238 ("Method of determining a chemotherapeutic regimen based on ERCC1 expression"); U.S. Pat. No. 7,107,095 ("Device for and method of rapid noninvasive measurement of parameters of diastolic function of left ventricle and automated evaluation of the measured profile of left ventricular function at rest and with exercise"); U.S. Pat. No. 7,054,688 ("Heart stimulator with evoked response detector and an arrangement for determining the stimulation threshold"); U.S. Pat. No. 7,047,083 ("Method and apparatus for identifying lead-related conditions using lead impedance measurements"); U.S. Pat. No. 6,988,498 ("Administration of CPAP treatment pressure in presence of apnea"); U.S. Pat. No. 6,978,177 ("Method and apparatus for using atrial discrimination algorithms to determine optimal pacing therapy and therapy timing"); U.S. Pat. No. 6,671,548 ("Implantable stimulation device and method for discrimination atrial and ventricular arrhythmias"); U.S. Pat. No. 6,336,048 ("Implantable active medical device enslaved to at least one physiological parameter").

Operation 3097 describes signaling an identifier of a capsule (e.g. recording system 2230 generating one or more data records 2235 each associating a serial number or other capsule identifier 2236 with a manufacturing lot number, ingestion or other event data, medication content, dosage, or other related data 2237 from or about a specific capsule 491). This can occur, for example, in a context in which distillation unit 460 includes or otherwise interacts with a response module 2250, in which several self-identifying pills are provided to subject 382, and in which subject 382 is directly or indirectly available frequently enough to permit monitoring as described herein.

With reference again to flow 3000 of FIG. 30 and to other flows described above, one or more operations of 21-26 may each (optionally) include or relate to one or more instances of operation 3091, operation 3095, operation 3096, or operation 3097 as described below. Such a "utility" operation may be carried out, for example, by application or decision logic (implemented in one or more primary components 221-226 or distillation units 460 or other data handling units responsive to one or more preparatory operations, e.g.) configured to implement or communicate one or more outputs of 251-256 or other useful results described herein.

In light of teachings herein, numerous existing techniques may be applied for configuring special-purpose circuitry or other structures effective for recognizing trends and other quantitative measurement comparisons as described herein without undue experimentation. See, e.g., U.S. Pat. No. 7,485,095 ("Measurement and analysis of trends in physiological and/or health data"); U.S. Pat. No. 7,297,119 ("Sleep apnea risk evaluation"); U.S. Pat. No. 7,187,960 ("Apparatus and method for measuring biologic parameters"); U.S. Pat. No. 7,460,899 ("Apparatus and method for monitoring heart rate variability"); U.S. Pat. No. 7,914,468 ("Systems and methods for monitoring and modifying behavior"); U.S. Pat. No. 7,819,311 ("Multispectral biometric sensor"); U.S. Pat. No. 7,674,231 ("Wearable pulse wave velocity blood pressure sensor and methods of calibration thereof"); U.S. Pat. No. 7,983,759 ("Advanced patient management for reporting multiple health-related parameters"); U.S. Pat. No. 7,959,568 ("Advanced patient management for identifying, displaying and assisting with correlating health-related data"); U.S. Pat. No. 7,911,348 ("Methods for refining patient, staff and visitor profiles used in monitoring quality and performance at a healthcare facility"); U.S. Pat. No. 7,894,849 ("Mobile personal services platform for providing feedback"); U.S. Pat. No. 7,825,815 ("Apparatus, systems, and methods for gathering and processing biometric and biomechanical data"); U.S. Pat. No. 7,806,852 ("Method and apparatus for patient-controlled medical therapeutics"); U.S. Pat. No. 7,870,249 ("Networked system for interactive communication and remote monitoring of individuals").

In light of teachings herein, numerous existing techniques may be applied for configuring special-purpose circuitry or other structures effective for recognizing and manipulating portions of audio signals and audible events as described herein without undue experimentation. See, e.g., U.S. Pat. No. 7,940,914 ("Detecting emotion in voice signals in a call center"); U.S. Pat. No. 7,881,934 ("Method and system for adjusting the voice prompt of an interactive system based upon the user's state"); U.S. Pat. No. 7,822,192 ("Sound event processing with echo analysis"); U.S. Pat. No. 7,809,574 ("Word recognition using choice lists"); U.S. Pat. No. 7,707,037 ("Archiving of surveillance data"); U.S. Pat. No. 6,731,307 ("User interface/entertainment device that simulates personal interaction and responds to user's mental state and/or personality"); U.S. Pat. No. 6,728,679 ("Self-updating user interface/entertainment device that simulates personal interaction"); U.S. Pat. No. 7,668,710 ("Determining voice recognition accuracy in a voice recognition system"); U.S. Pat. No. 7,577,569 ("Combined speech recognition and text-to-speech generation"); U.S. Pat. No. 7,467,089 ("Combined speech and handwriting recognition"); U.S. Pat. No. 7,103,542 ("Automatically improving a voice recognition system"); U.S. Pat. No. 6,282,549 ("Indexing of media content on a network"); U.S. Pat. No. 7,987,280 ("System and method for locating and capturing desired media content from media broadcasts"); U.S. Pat. No. 7,914,442 ("Endoscopic smart probe and method"); U.S. Pat. No. 7,188,767 ("Physical condition or environmental threat detection appliance system"); U.S. Pat. No. 6,971,993 ("Method for utilizing oral movement and related events"); U.S. Pat. No. 7,983,933 ("Patient monitoring via image capture").

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES 1. (Independent) A system comprising:
circuitry for deciding whether to obtain one or more images of a region responsively to whether a wireless signal has been received from a device in the region; and
circuitry for signaling a data distillation indicative of a regimen compliance status responsively to whether the wireless signal has been received from the device in the region.

2. The system of any of the above SYSTEM CLAUSES in which the circuitry for deciding whether to obtain one or more images of a region responsively to whether a wireless signal has been received from a device in the region comprises:
circuitry for conditioning an output upon receiving radio-frequency energy, the wireless signal including the radio-frequency energy, the output being an image capture command signal manifesting a decision to obtain the one or more images of the region.

3. The system of any of the above SYSTEM CLAUSES in which the circuitry for deciding whether to obtain one or more images of a region responsively to whether a wireless signal has been received from a device in the region comprises:
circuitry for signaling a passive wireless transponder in a capsule, the device being the capsule.

4. The system of any of the above SYSTEM CLAUSES in which the circuitry for deciding whether to obtain one or more images of a region responsively to whether a wireless signal has been received from a device in the region comprises:
circuitry for conditioning an output upon a presence of or an absence of an indication of contraband, the contraband being detectable by the device and within the one or more images of the region.

5. The system of any of the above SYSTEM CLAUSES in which the circuitry for deciding whether to obtain one or more images of a region responsively to whether a wireless signal has been received from a device in the region comprises:
circuitry for obtaining an indication of an inhalation of a bioactive material, the device configured to contain the bioactive material, the wireless signal indicating the inhalation of the bioactive material.

6. The system of any of the above SYSTEM CLAUSES in which the circuitry for deciding whether to obtain one or more images of a region responsively to whether a wireless signal has been received from a device in the region comprises:
circuitry for obtaining an indication of when at least a portion of a vessel moved, the vessel being the device, the wireless signal indicating when at least a portion of the vessel moved.

7. The system of any of the above SYSTEM CLAUSES in which the circuitry for deciding whether to obtain one or more images of a region responsively to whether a wireless signal has been received from a device in the region comprises:
circuitry for detecting whether data from one or more sensors indicate an actuation of a portion of a dispensing device, at least one of the one or more sensors being an optical sensor configured to obtain the one or more images of the region, the dispensing device being the device in the region, at least one of the one or more images of the region being an image of the dispensing device, a component of the data distillation indicative of the regimen compliance status resulting from an image processing protocol being applied to the image of the dispensing device responsively to whether the wireless signal has been received from the device in the region.

8. The system of any of the above SYSTEM CLAUSES in which the circuitry for deciding whether to obtain one or more images of a region responsively to whether a wireless signal has been received from a device in the region comprises:

circuitry for retrieving event data relating to an individual, the device being associated with the event data relating to the individual, the wireless signal identifying the device.

9. The system of any of the above SYSTEM CLAUSES in which the circuitry for deciding whether to obtain one or more images of a region responsively to whether a wireless signal has been received from a device in the region comprises:

circuitry for indicating a data distillation protocol at least partly based on a demographic attribute of a subpopulation, the wireless signal identifying the specific individual.

10. The system of any of the above SYSTEM CLAUSES, further comprising:

circuitry for detecting a device associated with an individual, the device in the region being the device associated with the individual.

11. The system of any of the above SYSTEM CLAUSES, further comprising:

circuitry for transmitting an identifier of a particular capsule, the wireless signal containing the identifier of the particular capsule, the device being or configured to contain the particular capsule.

12. The system of any of the above SYSTEM CLAUSES, further comprising:

circuitry for obtaining an indication whether a vessel has been ingested, the vessel being the device, the region being within a fixture that contains the vessel, the indication that the vessel has been ingested being that the wireless signal has been received from the device in the region.

13. The system of any of the above SYSTEM CLAUSES, further comprising:

circuitry for obtaining an indication whether a vessel has been ingested, the vessel being the device, the region being within a digestive tract that contains the vessel, the indication that the vessel has been ingested being that the wireless signal has been received from the device in the region.

14. The system of any of the above SYSTEM CLAUSES, further comprising:

circuitry for obtaining a test result of a sample extracted from an individual, the device being configured to extract the sample from the individual.

15. The system of any of the above SYSTEM CLAUSES, further comprising:

circuitry for obtaining a test result of a sample extracted from an individual, the device being a sample tester, the sample tester being configured to generate the test result by testing the sample extracted from the individual.

16. The system of any of the above SYSTEM CLAUSES, further comprising:

circuitry for causing wireless signal transmission circuitry in situ to initiate a wireless transmission in response to an indication of ingestion by transmitting an interrogation signal into the region, a digestive tract including the region, the device including the wireless signal transmission circuitry, the device being configured to initiate the wireless transmission in response to the interrogation signal if the device manifests the indication of ingestion and if the device is in the region.

17. The system of any of the above SYSTEM CLAUSES in which the circuitry for signaling a data distillation indicative of a regimen compliance status responsively to whether the wireless signal has been received from the device in the region comprises:

circuitry for conditioning a regimen noncompliance determination upon a determination that a wireless signal in a first frequency range below a reference frequency coincided with a presence of a wireless signal in a second frequency range above the reference frequency in a vicinity of a capsule, the device being the capsule, the region being the vicinity of the capsule, the data distillation conditionally indicating a result of the regimen noncompliance determination.

18. The system of any of the above SYSTEM CLAUSES in which the circuitry for signaling a data distillation indicative of a regimen compliance status responsively to whether the wireless signal has been received from the device in the region comprises:

circuitry for conditioning a compliance-positive indication upon a determination that a wireless signal in a first frequency range below a reference frequency coincided with an absence of a wireless signal in a second frequency range above the reference frequency in a vicinity of a capsule, the device being the capsule, the region being the vicinity of the capsule, the data distillation conditionally indicating a result of the compliance-positive indication.

19. The system of any of the above SYSTEM CLAUSES in which the circuitry for signaling a data distillation indicative of a regimen compliance status responsively to whether the wireless signal has been received from the device in the region comprises:

circuitry for conditioning a regimen compliance determination upon a first compliance-positive indication and upon a second compliance-positive indication, the data distillation indicating a result of the regimen compliance determination.

20. The system of any of the above SYSTEM CLAUSES in which the circuitry for signaling a data distillation indicative of a regimen compliance status responsively to whether the wireless signal has been received from the device in the region comprises:

circuitry for conditioning a regimen noncompliance determination upon a first compliance-negative indication and upon a second compliance-negative indication, the data distillation indicating a result of the regimen noncompliance determination.

21. The system of any of the above SYSTEM CLAUSES in which the circuitry for signaling a data distillation indicative of a regimen compliance status responsively to whether the wireless signal has been received from the device in the region comprises:

circuitry for conditioning whether a message is sent upon whether a temperature exceeds a threshold, the temperature being at the device, the device being supportable by a human being, the threshold being above 37° C. by at most a few degrees, the message conditionally being sent if the data distillation indicative of the regimen compliance status indicates that the temperature exceeds the threshold.

22. The system of any of the above SYSTEM CLAUSES in which the circuitry for signaling a data distillation indicative of a regimen compliance status responsively to whether the wireless signal has been received from the device in the region comprises:

circuitry for conditioning whether a message is sent upon whether a temperature exceeds a threshold, the temperature being at the device, the device including a temperature sensor, whether the message is sent being a component of the data distillation indicative of the regimen compliance status.

23. The system of any of the above SYSTEM CLAUSES in which the circuitry for signaling a data distillation indicative of a regimen compliance status responsively to whether the wireless signal has been received from the device in the region comprises:

circuitry for causing a door to become locked or unlocked, the data distillation indicative of the regimen compliance status including an electromechanical control signal configured to control a lock of the door.

24. The system of any of the above SYSTEM CLAUSES in which the circuitry for signaling a data distillation indicative of a regimen compliance status responsively to whether the wireless signal has been received from the device in the region comprises:

circuitry for deciding whether a status of an individual has apparently changed, the device configured to be supported by the individual, the status of the individual including the regimen compliance status, the data distillation being signaled responsively to whether the wireless signal has been received from the device in the region.

25. The system of any of the above SYSTEM CLAUSES in which the circuitry for signaling a data distillation indicative of a regimen compliance status responsively to whether the wireless signal has been received from the device in the region comprises:

circuitry for distilling historical data indicative of or contraindicative of a health status transition apparently relating to an infection in an individual, the data distillation indicative of the regimen compliance status resulting from distilling the historical data indicative of or contraindicative of a health status transition apparently relating to an infection in the individual responsively to whether the wireless signal has been received from the device in the region, the health status transition apparently relating to the infection in the individual being a health status improvement.

26. The system of any of the above SYSTEM CLAUSES in which the circuitry for signaling a data distillation indicative of a regimen compliance status responsively to whether the wireless signal has been received from the device in the region comprises:

circuitry for distilling historical data indicative of or contraindicative of a health status transition apparently relating to an infection in an individual, the data distillation indicative of the regimen compliance status resulting from distilling the historical data indicative of or contraindicative of a health status transition apparently relating to an infection in the individual responsively to whether the wireless signal has been received from the device in the region, the health status transition apparently relating to the infection in the individual being a health status deterioration.

27. The system of any of the above SYSTEM CLAUSES in which the circuitry for signaling a data distillation indicative of a regimen compliance status responsively to whether the wireless signal has been received from the device in the region comprises:

circuitry for distilling historical data indicative of or contraindicative of a health status transition apparently relating to cardiovascular disease in an individual, the data distillation indicative of the regimen compliance status resulting from distilling the historical data indicative of or contraindicative of a health status transition apparently relating to cardiovascular disease in the individual responsively to whether the wireless signal has been received from the device in the region, the health status transition apparently relating to cardiovascular disease in the individual being at least one of a health status improvement or a health status deterioration.

circuitry for transmitting a regimen compliance determination as an actuation signal, the data distillation including the actuation signal conditionally in response to the regimen compliance determination.

28. The system of any of the above SYSTEM CLAUSES in which the circuitry for signaling a data distillation indicative of a regimen compliance status responsively to whether the wireless signal has been received from the device in the region comprises:

circuitry for determining whether an event occurred within a normal interval of time, the data distillation indicative of the regimen compliance status conditionally including a compliance-negative indication if the indication of the abnormally late order for the therapeutic component is obtained.

29. The system of any of the above SYSTEM CLAUSES in which the circuitry for signaling a data distillation indicative of a regimen compliance status responsively to whether the wireless signal has been received from the device in the region comprises:

circuitry for obtaining an indication of whether an individual remains enrolled in a program requiring a therapeutic regimen, the data distillation indicative of the regimen compliance status resulting from an application of a distillation protocol specified by the program requiring the therapeutic regimen.

30. The system of any of the above SYSTEM CLAUSES in which the circuitry for signaling a data distillation indicative of a regimen compliance status responsively to whether the wireless signal has been received from the device in the region comprises:

circuitry for signaling a regimen compliance data distillation by identifying a data distillation protocol, the data distillation indicative of the regimen compliance status being the regimen compliance data distillation, the data distillation protocol being a component of a user-specified monitoring regimen.

31. The system of any of the above SYSTEM CLAUSES in which the circuitry for signaling a data distillation indicative of a regimen compliance status responsively to whether the wireless signal has been received from the device in the region comprises:

circuitry for signaling a regimen compliance data distillation by identifying a data distillation protocol, the data distillation indicative of the regimen compliance status being the regimen compliance data distillation, the data distillation protocol being selected in response to a type of data received in the wireless signal.

32. The system of any of the above SYSTEM CLAUSES in which the circuitry for signaling a data distillation indicative of a regimen compliance status responsively to whether the wireless signal has been received from the device in the region comprises:

circuitry for signaling a regimen compliance data distillation by transmitting the regimen compliance data distillation responsively to whether the wireless signal has been received from the device in the region, the regimen compliance data distillation being the data distillation indicative of the regimen compliance status.

33. The system of any of the above SYSTEM CLAUSES in which the circuitry for signaling a data distillation indicative of a regimen compliance status responsively to whether the wireless signal has been received from the device in the region comprises:

circuitry for obtaining a regimen compliance data distillation by causing an application of one or more sensor measurement thresholds, at least one of the one or more sensor measurement thresholds being configured to determine whether any sensor data from the region is apparently useless, the application of the one or more sensor measurement thresholds causing the regimen compliance data distillation selectively to exclude a portion of the sensor data from the region if the portion of the sensor data is apparently useless.

34. The system of any of the above SYSTEM CLAUSES in which the circuitry for signaling a data distillation indicative of a regimen compliance status responsively to whether the wireless signal has been received from the device in the region comprises:

circuitry for obtaining a regimen compliance data distillation by causing an application of one or more sensor measurement thresholds, at least one of the one or more sensor measurement thresholds being configured to determine whether any sensor data from the region indicates a health status change, the application of the one or more sensor measurement thresholds causing the regimen compliance data distillation selectively to include a portion of the sensor data from the region if the portion of the sensor data indicates a health status change.

35. The system of any of the above SYSTEM CLAUSES in which the circuitry for signaling a data distillation indicative of a regimen compliance status responsively to whether the wireless signal has been received from the device in the region comprises:

circuitry for obtaining a regimen compliance data distillation by causing an application of one or more sensor measurement thresholds to sensor data from the region.

36. The system of any of the above SYSTEM CLAUSES in which the circuitry for signaling a data distillation indicative of a regimen compliance status responsively to whether the wireless signal has been received from the device in the region comprises:

circuitry for obtaining a regimen compliance data distillation by causing an application of one or more auditory data distillation criteria, at least one of the one or more auditory distillation criteria being configured to determine whether auditory data from the region includes a compliance-positive indication, the compliance-positive indication being at least one of a swallowing sound or a vocalized assertion.

37. The system of any of the above SYSTEM CLAUSES in which the circuitry for signaling a data distillation indicative of a regimen compliance status responsively to whether the wireless signal has been received from the device in the region comprises:

circuitry for obtaining a regimen compliance data distillation by causing an application of one or more auditory data distillation criteria to auditory data from the region.

38. The system of any of the above SYSTEM CLAUSES in which the circuitry for signaling a data distillation indicative of a regimen compliance status responsively to whether the wireless signal has been received from the device in the region comprises:

circuitry for determining whether an individual is apparently compliant with a regimen targeting a portion of the individual, the individual being apparently compliant if the data distillation indicative of the regimen compliance status does not include a compliance-negative indication, the region intersecting the portion of the individual.

39. The system of any of the above SYSTEM CLAUSES in which the circuitry for signaling a data distillation indicative of a regimen compliance status responsively to whether the wireless signal has been received from the device in the region comprises:

circuitry for determining whether an individual is apparently compliant with a regimen targeting a portion of the individual, the individual being apparently compliant if the data distillation indicative of the regimen compliance status indicates a health status improvement, the region intersecting the portion of the individual.

40. The system of any of the above SYSTEM CLAUSES in which the circuitry for signaling a data distillation indicative of a regimen compliance status responsively to whether the wireless signal has been received from the device in the region comprises:

circuitry for determining whether an individual is apparently compliant with a regimen targeting a portion of the individual, the individual being apparently compliant if the data distillation indicative of the regimen compliance status includes a normalcy indication, the region intersecting the portion of the individual.

41. The system of any of the above SYSTEM CLAUSES in which the circuitry for signaling a data distillation indicative of a regimen compliance status responsively to whether the wireless signal has been received from the device in the region comprises:

circuitry for determining whether an individual is apparently compliant with a regimen targeting a portion of the individual, the region intersecting the portion of the individual.

42. The system of any of the above SYSTEM CLAUSES in which the circuitry for signaling a data distillation indicative of a regimen compliance status responsively to whether the wireless signal has been received from the device in the region comprises:

circuitry for determining whether a therapy is apparently having a specific effect, the data distillation indicative of the regimen compliance status being a determination of whether the therapy is apparently having the specific effect, the specific effect being at least one of a health status improvement or a health status deterioration.

43. The system of any of the above SYSTEM CLAUSES in which the circuitry for signaling a data distillation indicative of a regimen compliance status responsively to whether the wireless signal has been received from the device in the region comprises:

circuitry for applying a provider-specified criterion to device-detectable health-indicative data, the device-detectable health-indicative data including a component of the wireless signal, the provider-specified criterion signaling a data distillation protocol configured to extract the component of the wireless signal from the device-detectable health-indicative data.

44. The system of any of the above SYSTEM CLAUSES in which the circuitry for signaling a data distillation indicative of a regimen compliance status responsively to whether the wireless signal has been received from the device in the region comprises:

circuitry for applying a provider-specified criterion to device-detectable health-indicative data, the device-detectable health-indicative data including a manifestation of whether the wireless signal has been received, the provider-specified criterion signaling a data distillation protocol configured to extract the manifestation of whether the wireless signal has been received from the device-detectable health-indicative data.

45. The system of any of the above SYSTEM CLAUSES in which the circuitry for signaling a data distillation indicative of a regimen compliance status responsively to whether the wireless signal has been received from the device in the region comprises:

circuitry for applying a provider-specified criterion to device-detectable health-indicative data, the provider-specified criterion signaling a data distillation protocol, the device-detectable health-indicative data including a component of the wireless signal.

46. The system of any of the above SYSTEM CLAUSES in which the circuitry for signaling a data distillation indicative of a regimen compliance status responsively to whether the wireless signal has been received from the device in the region comprises:

circuitry for signaling an identifier of a capsule, the data distillation indicative of the regimen compliance status including the identifier of the capsule, the capsule being the device, the wireless signal being received from the region, the wireless signal effectively distinguishing the capsule from another capsule.

47. (Independent) A method comprising:

deciding whether to obtain one or more images of a region responsively to whether a wireless signal has been received from a device in the region; and invoking circuitry for signaling a data distillation indicative of a regimen compliance status responsively to whether the wireless signal has been received from the device in the region.

48. The method of any of the above METHOD CLAUSES in which the deciding whether to obtain one or more images of a region responsively to whether a wireless signal has been received from a device in the region comprises:

conditioning an output upon receiving radio-frequency energy, the wireless signal including the radio-frequency energy, the output being an image capture command signal manifesting a decision to obtain the one or more images of the region.

49. The method of any of the above METHOD CLAUSES in which the deciding whether to obtain one or more images of a region responsively to whether a wireless signal has been received from a device in the region comprises:

signaling a passive wireless transponder in a capsule, the device being the capsule.

50. The method of any of the above METHOD CLAUSES in which the deciding whether to obtain one or more images of a region responsively to whether a wireless signal has been received from a device in the region comprises:

conditioning an output upon a presence of or an absence of an indication of contraband, the contraband being detectable by the device and within the one or more images of the region.

51. The method of any of the above METHOD CLAUSES in which the deciding whether to obtain one or more images of a region responsively to whether a wireless signal has been received from a device in the region comprises:

obtaining an indication of an inhalation of a bioactive material, the device configured to contain the bioactive material, the wireless signal indicating the inhalation of the bioactive material.

52. The method of any of the above METHOD CLAUSES in which the deciding whether to obtain one or more images of a region responsively to whether a wireless signal has been received from a device in the region comprises:

obtaining an indication of when at least a portion of a vessel moved, the vessel being the device, the wireless signal indicating when at least a portion of the vessel moved.

53. The method of any of the above METHOD CLAUSES in which the deciding whether to obtain one or more images of a region responsively to whether a wireless signal has been received from a device in the region comprises:

retrieving event data relating to an individual, the device being associated with the event data relating to the individual, the wireless signal identifying the device.

54. The method of any of the above METHOD CLAUSES in which the deciding whether to obtain one or more images of a region responsively to whether a wireless signal has been received from a device in the region comprises:

indicating a data distillation protocol at least partly based on a demographic attribute of a subpopulation, the wireless signal identifying the specific individual.

55. The method of any of the above METHOD CLAUSES, further comprising:

detecting a device associated with an individual, the device in the region being the device associated with the individual.

56. The method of any of the above METHOD CLAUSES, further comprising:

transmitting an identifier of a particular capsule, the wireless signal containing the identifier of the particular capsule, the device being or configured to contain the particular capsule.

57. The method of any of the above METHOD CLAUSES, further comprising:

obtaining an indication whether a vessel has been ingested, the vessel being the device, the region being within a fixture that contains the vessel, the indication that the vessel has been ingested being that the wireless signal has been received from the device in the region.

58. The method of any of the above METHOD CLAUSES, further comprising:

obtaining an indication whether a vessel has been ingested, the vessel being the device, the region being within a digestive tract that contains the vessel, the indication that the vessel has been ingested being that the wireless signal has been received from the device in the region.

59. The method of any of the above METHOD CLAUSES, further comprising:

obtaining a test result of a sample extracted from an individual, the device being configured to extract the sample from the individual.

60. The method of any of the above METHOD CLAUSES, further comprising:

causing wireless signal transmission circuitry in situ to initiate a wireless transmission in response to an indication of ingestion by transmitting an interrogation signal into the region, a digestive tract including the region, the device including the wireless signal transmission circuitry, the device being configured to initiate the wireless transmission in response to the interrogation signal if the device manifests the indication of ingestion and if the device is in the region.

61. The method of any of the above METHOD CLAUSES in which the invoking circuitry for signaling a data distillation indicative of a regimen compliance status responsively to whether the wireless signal has been received from the device in the region comprises:

invoking circuitry for conditioning a regimen noncompliance determination upon a determination that a wireless signal in a first frequency range below a reference frequency coincided with a presence of a wireless signal in a second frequency range above the reference frequency in a vicinity of a capsule, the device being the capsule, the region being the vicinity of the capsule, the data distillation conditionally indicating a result of the regimen noncompliance determination.

62. The method of any of the above METHOD CLAUSES in which the invoking circuitry for signaling a data distillation indicative of a regimen compliance status responsively to whether the wireless signal has been received from the device in the region comprises:

invoking circuitry for conditioning a regimen compliance determination upon a first compliance-positive indication and upon a second compliance-positive indication, the data distillation indicating a result of the regimen compliance determination.

63. The method of any of the above METHOD CLAUSES in which the invoking circuitry for signaling a data distillation indicative of a regimen compliance status responsively to whether the wireless signal has been received from the device in the region comprises:
invoking circuitry for conditioning a regimen noncompliance determination upon a first compliance-negative indication and upon a second compliance-negative indication, the data distillation indicating a result of the regimen noncompliance determination.

64. The method of any of the above METHOD CLAUSES in which the invoking circuitry for signaling a data distillation indicative of a regimen compliance status responsively to whether the wireless signal has been received from the device in the region comprises:
invoking circuitry for conditioning whether a message is sent upon whether a temperature exceeds a threshold, the temperature being at the device, the device being supportable by a human being, the threshold being above 37° C. by at most a few degrees, the message conditionally being sent if the data distillation indicative of the regimen compliance status indicates that the temperature exceeds the threshold.

65. The method of any of the above METHOD CLAUSES in which the invoking circuitry for signaling a data distillation indicative of a regimen compliance status responsively to whether the wireless signal has been received from the device in the region comprises:
invoking circuitry for conditioning whether a message is sent upon whether a temperature exceeds a threshold, the temperature being at the device, the device including a temperature sensor, whether the message is sent being a component of the data distillation indicative of the regimen compliance status.

66. The method of any of the above METHOD CLAUSES in which the invoking circuitry for signaling a data distillation indicative of a regimen compliance status responsively to whether the wireless signal has been received from the device in the region comprises:
invoking circuitry for causing a door to become locked or unlocked, the data distillation indicative of the regimen compliance status including an electromechanical control signal configured to control a lock of the door.

67. The method of any of the above METHOD CLAUSES in which the invoking circuitry for signaling a data distillation indicative of a regimen compliance status responsively to whether the wireless signal has been received from the device in the region comprises:
invoking circuitry for deciding whether a status of an individual has apparently changed, the device configured to be supported by the individual, the status of the individual including the regimen compliance status, the data distillation being signaled responsively to whether the wireless signal has been received from the device in the region.

68. The method of any of the above METHOD CLAUSES in which the invoking circuitry for signaling a data distillation indicative of a regimen compliance status responsively to whether the wireless signal has been received from the device in the region comprises:
invoking circuitry for distilling historical data indicative of or contraindicative of a health status transition apparently relating to an infection in an individual, the data distillation indicative of the regimen compliance status resulting from distilling the historical data indicative of or contraindicative of a health status transition apparently relating to an infection in the individual responsively to whether the wireless signal has been received from the device in the region, the health status transition apparently relating to the infection in the individual being a health status improvement.

69. The method of any of the above METHOD CLAUSES in which the invoking circuitry for signaling a data distillation indicative of a regimen compliance status responsively to whether the wireless signal has been received from the device in the region comprises:
invoking circuitry for distilling historical data indicative of or contraindicative of a health status transition apparently relating to cardiovascular disease in an individual, the data distillation indicative of the regimen compliance status resulting from distilling the historical data indicative of or contraindicative of a health status transition apparently relating to cardiovascular disease in the individual responsively to whether the wireless signal has been received from the device in the region, the health status transition apparently relating to cardiovascular disease in the individual being at least one of a health status improvement or a health status deterioration.
invoking circuitry for transmitting a regimen compliance determination as an actuation signal, the data distillation including the actuation signal conditionally in response to the regimen compliance determination.

70. The method of any of the above METHOD CLAUSES in which the invoking circuitry for signaling a data distillation indicative of a regimen compliance status responsively to whether the wireless signal has been received from the device in the region comprises:
invoking circuitry for determining whether an event occurred within a normal interval of time, the data distillation indicative of the regimen compliance status conditionally including a compliance-negative indication if the indication of the abnormally late order for the therapeutic component is obtained.

71. The method of any of the above METHOD CLAUSES in which the invoking circuitry for signaling a data distillation indicative of a regimen compliance status responsively to whether the wireless signal has been received from the device in the region comprises:
invoking circuitry for obtaining an indication of whether an individual remains enrolled in a program requiring a therapeutic regimen, the data distillation indicative of the regimen compliance status resulting from an application of a distillation protocol specified by the program requiring the therapeutic regimen.

72. The method of any of the above METHOD CLAUSES in which the invoking circuitry for signaling a data distillation indicative of a regimen compliance status responsively to whether the wireless signal has been received from the device in the region comprises:
invoking circuitry for signaling a regimen compliance data distillation by identifying a data distillation protocol, the data distillation indicative of the regimen compliance status being the regimen compliance data distillation, the data distillation protocol being a component of a user-specified monitoring regimen.

73. The method of any of the above METHOD CLAUSES in which the invoking circuitry for signaling a data distillation indicative of a regimen compliance status responsively to whether the wireless signal has been received from the device in the region comprises:
invoking circuitry for signaling a regimen compliance data distillation by identifying a data distillation protocol, the data distillation indicative of the regimen compliance status being the regimen compliance data distillation, the data distillation protocol being selected in response to a type of data received in the wireless signal.

74. The method of any of the above METHOD CLAUSES in which the invoking circuitry for signaling a data distillation indicative of a regimen compliance status responsively to whether the wireless signal has been received from the device in the region comprises:

invoking circuitry for signaling a regimen compliance data distillation by transmitting the regimen compliance data distillation responsively to whether the wireless signal has been received from the device in the region, the regimen compliance data distillation being the data distillation indicative of the regimen compliance status.

75. The method of any of the above METHOD CLAUSES in which the invoking circuitry for signaling a data distillation indicative of a regimen compliance status responsively to whether the wireless signal has been received from the device in the region comprises:

invoking circuitry for obtaining a regimen compliance data distillation by causing an application of one or more sensor measurement thresholds, at least one of the one or more sensor measurement thresholds being configured to determine whether any sensor data from the region is apparently useless, the application of the one or more sensor measurement thresholds causing the regimen compliance data distillation selectively to exclude a portion of the sensor data from the region if the portion of the sensor data is apparently useless.

76. The method of any of the above METHOD CLAUSES in which the invoking circuitry for signaling a data distillation indicative of a regimen compliance status responsively to whether the wireless signal has been received from the device in the region comprises:

invoking circuitry for obtaining a regimen compliance data distillation by causing an application of one or more sensor measurement thresholds to sensor data from the region.

77. The method of any of the above METHOD CLAUSES in which the invoking circuitry for signaling a data distillation indicative of a regimen compliance status responsively to whether the wireless signal has been received from the device in the region comprises:

invoking circuitry for obtaining a regimen compliance data distillation by causing an application of one or more auditory data distillation criteria, at least one of the one or more auditory distillation criteria being configured to determine whether auditory data from the region includes a compliance-positive indication, the compliance-positive indication being at least one of a swallowing sound or a vocalized assertion.

78. The method of any of the above METHOD CLAUSES in which the invoking circuitry for signaling a data distillation indicative of a regimen compliance status responsively to whether the wireless signal has been received from the device in the region comprises:

invoking circuitry for obtaining a regimen compliance data distillation by causing an application of one or more auditory data distillation criteria to auditory data from the region.

79. The method of any of the above METHOD CLAUSES in which the invoking circuitry for signaling a data distillation indicative of a regimen compliance status responsively to whether the wireless signal has been received from the device in the region comprises:

invoking circuitry for determining whether an individual is apparently compliant with a regimen targeting a portion of the individual, the individual being apparently compliant if the data distillation indicative of the regimen compliance status does not include a compliance-negative indication, the region intersecting the portion of the individual.

80. The method of any of the above METHOD CLAUSES in which the invoking circuitry for signaling a data distillation indicative of a regimen compliance status responsively to whether the wireless signal has been received from the device in the region comprises:

invoking circuitry for determining whether an individual is apparently compliant with a regimen targeting a portion of the individual, the individual being apparently compliant if the data distillation indicative of the regimen compliance status indicates a health status improvement, the region intersecting the portion of the individual.

81. The method of any of the above METHOD CLAUSES in which the invoking circuitry for signaling a data distillation indicative of a regimen compliance status responsively to whether the wireless signal has been received from the device in the region comprises:

invoking circuitry for determining whether an individual is apparently compliant with a regimen targeting a portion of the individual, the individual being apparently compliant if the data distillation indicative of the regimen compliance status includes a normalcy indication, the region intersecting the portion of the individual.

82. The method of any of the above METHOD CLAUSES in which the invoking circuitry for signaling a data distillation indicative of a regimen compliance status responsively to whether the wireless signal has been received from the device in the region comprises:

invoking circuitry for determining whether an individual is apparently compliant with a regimen targeting a portion of the individual, the region intersecting the portion of the individual.

83. The method of any of the above METHOD CLAUSES in which the invoking circuitry for signaling a data distillation indicative of a regimen compliance status responsively to whether the wireless signal has been received from the device in the region comprises:

invoking circuitry for determining whether a therapy is apparently having a specific effect, the data distillation indicative of the regimen compliance status being a determination of whether the therapy is apparently having the specific effect, the specific effect being at least one of a health status improvement or a health status deterioration.

84. The method of any of the above METHOD CLAUSES in which the invoking circuitry for signaling a data distillation indicative of a regimen compliance status responsively to whether the wireless signal has been received from the device in the region comprises:

invoking circuitry for applying a provider-specified criterion to device-detectable health-indicative data, the device-detectable health-indicative data including a component of the wireless signal, the provider-specified criterion signaling a data distillation protocol configured to extract the component of the wireless signal from the device-detectable health-indicative data.

85. The method of any of the above METHOD CLAUSES in which the invoking circuitry for signaling a data distillation indicative of a regimen compliance status responsively to whether the wireless signal has been received from the device in the region comprises:

invoking circuitry for applying a provider-specified criterion to device-detectable health-indicative data, the device-detectable health-indicative data including a manifestation of whether the wireless signal has been received, the provider-specified criterion signaling a data distillation protocol configured to extract the manifestation of whether the wireless signal has been received from the device-detectable health-indicative data.

86. The method of any of the above METHOD CLAUSES in which the invoking circuitry for signaling a data distillation indicative of a regimen compliance status responsively to whether the wireless signal has been received from the device in the region comprises:

invoking circuitry for applying a provider-specified criterion to device-detectable health-indicative data, the provider-specified criterion signaling a data distillation protocol, the device-detectable health-indicative data including a component of the wireless signal.

87. (Independent) A method comprising:

detecting a first indication whether a first device has been ingested in content of a signal from the first device;

detecting an apparent presence of or absence of a first device at a toilet as a second indication whether the first device has been ingested; and signaling a data distillation indicative of a regimen compliance status partly based on the first indication whether the first device has been ingested in the content of the signal from the first device and partly based on the apparent presence of or absence of the first device at the toilet as the second indication whether the first device has been ingested.

88. The method of CLAUSE 87, further comprising:

performing the operation(s) of any one or more of the above METHOD CLAUSES that depend from METHOD CLAUSE 47.

89. (Independent) A method comprising:

determining whether a presence of a wireless signal in a first frequency range below a threshold frequency occurred contemporaneously with an absence of a wireless signal in a second frequency range above the threshold frequency; and indicating a regimen compliance status of a subject in response to the circuitry for determining whether a presence of a wireless signal in a first frequency range below a threshold frequency occurred contemporaneously with an absence of a wireless signal in a second frequency range above the threshold frequency.

90. The method of CLAUSE 89, further comprising:

performing the operation(s) of any one or more of the above METHOD CLAUSES that depend from METHOD CLAUSE 47.

91. (Independent) A method comprising:

generating a device-detectable wireless transmission; and causing the wireless signal transmission circuitry in situ to initiate a wireless transmission detectable by an ex situ device in response to a material-selective in situ detection of a biological material.

92. The method of CLAUSE 91, further comprising:

performing the operation(s) of any one or more of the above METHOD CLAUSES that depend from METHOD CLAUSE 47.

93. (Independent) A method comprising:

obtaining first data indicating that at least a portion of a container moved, the first data signaling that a therapeutic material has been administered to a portion of a subject; and signaling second data corroborating or contraindicating that the therapeutic material has been administered to the portion of the subject responsive to the first data indicating that at least the portion of the container moved.

94. The method of CLAUSE 93, further comprising:

performing the operation(s) of any one or more of the above METHOD CLAUSES that depend from METHOD CLAUSE 47.

95. (Independent) A method comprising:

obtaining an indication whether a vessel has been ingested by a subject; and signaling a decision whether to actuate a mechanical component outside the subject responsive to the indication whether the vessel has been ingested by the subject.

96. The method of CLAUSE 95, further comprising:

performing the operation(s) of any one or more of the above METHOD CLAUSES that depend from METHOD CLAUSE 47.

97. (Independent) A system comprising:

means for performing the operation(s) of any one or more of the above METHOD CLAUSES.

98. (Independent) An article of manufacture comprising:

one or more physical media configured to bear a device-detectable implementation of a method including at least deciding whether to obtain one or more images of a region responsively to whether a wireless signal has been received from a device in the region; and signaling a data distillation indicative of a regimen compliance status responsively to whether the wireless signal has been received from the device in the region.

99. The article of manufacture of CLAUSE 98 in which a portion of the one or more physical media comprises:

one or more signal-bearing media configured to transmit one or more instructions for performing the operation(s) of any one or more of the above METHOD CLAUSES.

100. (Independent) An article of manufacture comprising:

one or more physical media bearing a device-detectable output indicating an occurrence of deciding whether to obtain one or more images of a region responsively to whether a wireless signal has been received from a device in the region; and signaling a data distillation indicative of a regimen compliance status responsively to whether the wireless signal has been received from the device in the region.

101. The article of manufacture of CLAUSE 100 in which a portion of the one or more physical media comprises:

one or more physical media bearing a device-detectable output indicating an occurrence of the operation(s) of any one or more of the above METHOD CLAUSES.

102. The article of manufacture of CLAUSE 100 in which at least one of the one or more physical media comprises:

one or more signal-bearing media bearing at least one signal from an implementation having at least circuitry for signaling a data distillation indicative of a regimen compliance status responsively to whether the wireless signal has been received from the device in the region.

All of the patents and other publications referred to above are incorporated herein by reference generally—including those identified in relation to particular new applications of existing techniques—to the extent not inconsistent herewith. While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A system comprising:

circuitry configured to decide whether or not to obtain one or more images of a region responsively to whether or not a first wireless signal has been received from a device in the region; and circuitry configured to signal a data distillation indicative of a regimen compliance status responsively to whether or not the first wireless signal has been received from the device in the region in which the circuitry configured to signal the data distillation indicative of the regimen compliance status responsively to whether or not the first wireless signal has been received from the device in the region comprises:
- circuitry configured to condition a regimen noncompliance determination upon a determination that a presence of a second wireless signal from a capsule in a first frequency range below a reference frequency coincided with a presence of a third wireless signal in a second frequency range above the reference frequency from the capsule, the device being the capsule, the region being a vicinity of the capsule, the data distillation conditionally indicating a result of the regimen noncompliance determination;
- circuitry configured to condition a regimen noncompliance determination upon a first compliance-negative indication and upon a second compliance-negative indication, the data distillation indicating a result of the regimen noncompliance determination; and
- circuitry configured to cause a door to become locked or unlocked, the data distillation indicative of the regimen compliance status including an electromechanical control signal configured to control a lock of the door.

2. The system of claim 1 in which the circuitry configured to decide whether or not to obtain one or more images of the region responsively to whether or not the first wireless signal has been received from the device in the region comprises:
- circuitry configured to condition an output upon a presence of or an absence of an indication of contraband, the contraband being detectable by the device and within the one or more images of the region.

3. The system of claim 1 in which the circuitry configured to signal the data distillation indicative of the regimen compliance status responsively to whether or not the wireless signal has been received from the device in the region comprises:
- circuitry configured to condition a regimen compliance determination upon a first compliance-positive indication and upon a second compliance-positive indication, the data distillation indicating a result of the regimen compliance determination.

4. The system of claim 1 in which the circuitry configured to signal the data distillation indicative of the regimen compliance status responsively to whether or not the first wireless signal has been received from the device in the region comprises:
- circuitry configured to condition whether or not a message is sent upon whether or not a temperature exceeds a threshold, the temperature being at the device, the device including a temperature sensor, whether or not the message is sent being a component of the data distillation indicative of the regimen compliance status.

5. The system of claim 1 in which the circuitry configured to signal the data distillation indicative of the regimen compliance status responsively to whether or not the first wireless signal has been received from the device in the region comprises:
- circuitry configured to decide whether or not a status of an individual has changed, the device configured to be supported by the individual, the status of the individual including the regimen compliance status, the data distillation being signaled responsively to whether or not the first wireless signal has been received from the device in the region.

6. The system of claim 1 in which the circuitry configured to signal the data distillation indicative of the regimen compliance status responsively to whether or not the first wireless signal has been received from the device in the region comprises:
- circuitry configured to distill historical data indicative of or contraindicative of a health status transition relating to an infection in an individual, the data distillation indicative of the regimen compliance status resulting from distilling the historical data indicative of or contraindicative of a health status transition relating to an infection in the individual responsively to whether or not the wireless signal has been received from the device in the region, the health status transition relating to the infection in the individual being a health status improvement.

7. The system of claim 1 in which the circuitry configured to signal the data distillation indicative of the regimen compliance status responsively to whether or not the first wireless signal has been received from the device in the region comprises:
- circuitry configured to obtain an indication of whether or not an individual remains enrolled in a program requiring a therapeutic regimen, the data distillation indicative of the regimen compliance status resulting from an application of a distillation protocol specified by the program requiring the therapeutic regimen.

8. The system of claim 1 in which the circuitry configured to signal the data distillation indicative of the regimen compliance status responsively to whether or not the first wireless signal has been received from the device in the region comprises:
- circuitry configured to signal a regimen compliance data distillation by identifying a data distillation protocol, the data distillation indicative of the regimen compliance status being the regimen compliance data distillation, the data distillation protocol being selected in response to a type of data received in the wireless signal.

9. The system of claim 1 in which the circuitry configured to signal the data distillation indicative of the regimen compliance status responsively to whether or not the first wireless signal has been received from the device in the region comprises:
- circuitry configured to obtain a regimen compliance data distillation by causing an application of one or more auditory data distillation criteria, at least one of the one or more auditory distillation criteria being configured to determine whether or not auditory data from the region includes a compliance-positive indication, the compliance-positive indication being at least one of a swallowing sound or a vocalized assertion.

10. The system of claim 1 in which the circuitry configured to signal the data distillation indicative of the regimen compliance status responsively to whether or not the first wireless signal has been received from the device in the region comprises:
- circuitry configured to obtain a regimen compliance data distillation by causing an application of one or more auditory data distillation criteria to auditory data from the region, the data distillation indicative of the regimen compliance status being the regimen compliance data distillation.

11. The system of claim 1 in which the circuitry configured to signal the data distillation indicative of the regimen compliance status responsively to whether or not the first wireless signal has been received from the device in the region comprises:

circuitry configured to determine whether or not an individual is compliant with a regimen targeting a portion of the individual, the individual being compliant if the data distillation indicative of the regimen compliance status includes a normalcy indication, the region intersecting the portion of the individual.

12. The system of claim 1 in which the circuitry configured to signal the data distillation indicative of the regimen compliance status responsively to whether or not the first wireless signal has been received from the device in the region comprises:

circuitry configured to determine whether or not a therapy is having a specific effect, the data distillation indicative of the regimen compliance status being a determination of whether or not the therapy is having the specific effect, the specific effect being at least one of a health status improvement or a health status deterioration.

13. A system comprising:

circuitry configured to decide whether or not to obtain one or more images of a region responsively to whether or not a first wireless signal has been received from a device in the region; and circuitry configured to signal a data distillation indicative of a regimen compliance status responsively to whether or not the first wireless signal has been received from the device in the region in which the circuitry configured to signal the data distillation indicative of the regimen compliance status responsively to whether or not the first wireless signal has been received from the device in the region comprises:

circuitry configured to condition a regimen compliance determination upon a first compliance positive indication and upon a second compliance positive indication, the data distillation indicating a result of the regimen compliance determination;

circuitry configured to condition whether or not a message is sent upon whether or not a temperature exceeds a threshold, the temperature being at the device, the device including a temperature sensor, the device being an ingested capsule, whether or not the message is sent being a component of the data distillation indicative of the regimen compliance status; and circuitry configured to distill historical data indicative of or contraindicative of a health status transition relating to an infection in an individual, the data distillation indicative of the regimen compliance status resulting from distilling the historical data indicative of or contraindicative of a health status transition relating to an infection in the individual responsively to whether or not the first wireless signal has been received from the device in the region, the health status transition relating to the infection in the individual being a health status improvement or being a health status deterioration.

14. The system of claim 13 in which the circuitry configured to decide whether or not to obtain one or more images of the region responsively to whether or not the first wireless signal has been received from the device in the region comprises:

circuitry configured to condition an output upon receiving radio-frequency energy, the first wireless signal including the radio-frequency energy, the output being an image capture command signal manifesting a decision to obtain the one or more images of the region.

15. The system of claim 13 in which the circuitry configured to decide whether or not to obtain one or more images of the region responsively to whether or not the first wireless signal has been received from the device in the region comprises:

circuitry configured to signal a passive wireless transponder in a capsule, the device being the capsule.

16. The system of claim 13 in which the circuitry configured to decide whether or not to obtain one or more images of the region responsively to whether or not the first wireless signal has been received from the device in the region comprises:

circuitry configured to obtain an indication of an inhalation of a bioactive material, the device configured to contain the bioactive material, the first wireless signal indicating the inhalation of the bioactive material.

17. The system of claim 13, further comprising:

circuitry configured to obtain a test result of a sample extracted from an individual, the device being a sample tester, the sample tester being configured to generate the test result by testing the sample extracted from the individual.

18. The system of claim 13 in which the circuitry configured to signal the data distillation indicative of the regimen compliance status responsively to whether or not the first wireless signal has been received from the device in the region comprises:

circuitry configured to condition a regimen noncompliance determination upon a determination that a presence of a second wireless signal from a capsule in a first frequency range below a reference frequency coincided with a presence of a third wireless signal in a second frequency range above the reference frequency from the capsule, the device being the capsule, the region being a vicinity of the capsule, the data distillation conditionally indicating a result of the regimen noncompliance determination.

19. The system of claim 13 in which the circuitry configured to signal the data distillation indicative of the regimen compliance status responsively to whether or not the first wireless signal has been received from the device in the region comprises:

circuitry configured to condition a regimen noncompliance determination upon a first compliance-negative indication and upon a second compliance-negative indication, the data distillation indicating a result of the regimen noncompliance determination.

20. The system of claim 13 in which the circuitry configured to signal the data distillation indicative of the regimen compliance status responsively to whether or not the first wireless signal has been received from the device in the region comprises:

circuitry configured to cause a door to become locked or unlocked, the data distillation indicative of the regimen compliance status including an electromechanical control signal configured to control a lock of the door.

21. The system of claim 13 in which the circuitry configured to signal the data distillation indicative of the regimen compliance status responsively to whether or not the first wireless signal has been received from the device in the region comprises:

circuitry configured to transmit a regimen compliance determination as an actuation signal, the data distillation including the actuation signal conditionally in response to the regimen compliance determination.

22. The system of claim 13 in which the circuitry configured to signal the data distillation indicative of the regimen compliance status responsively to whether or not the first wireless signal has been received from the device in the region comprises:
    circuitry configured to signal an identifier of a capsule, the data distillation indicative of the regimen compliance status including the identifier of the capsule, the capsule being the device, the first wireless signal being received from the region, the first wireless signal effectively distinguishing the capsule from another capsule.

23. The system of claim 13 in which the circuitry configured to signal the data distillation indicative of the regimen compliance status responsively to whether or not the first wireless signal has been received from the device in the region comprises:
    circuitry configured to signal a regimen compliance data distillation by identifying a data distillation protocol, the data distillation indicative of the regimen compliance status being the regimen compliance data distillation, the data distillation protocol being selected in response to a type of data received in the wireless signal.

24. The system of claim 13 in which the circuitry configured to signal the data distillation indicative of the regimen compliance status responsively to whether or not the first wireless signal has been received from the device in the region comprises:
    circuitry configured to obtain a regimen compliance data distillation by causing an application of one or more auditory data distillation criteria, at least one of the one or more auditory distillation criteria being configured to determine whether or not auditory data from the region includes a compliance-positive indication, the compliance-positive indication being at least one of a swallowing sound or a vocalized assertion.

25. The system of claim 13 in which the circuitry configured to signal the data distillation indicative of the regimen compliance status responsively to whether or not the first wireless signal has been received from the device in the region comprises:
    circuitry configured to obtain a regimen compliance data distillation by causing an application of one or more auditory data distillation criteria to auditory data from the region, the data distillation indicative of the regimen compliance status being the regimen compliance data distillation.

26. The system of claim 13 in which the circuitry configured to signal the data distillation indicative of the regimen compliance status responsively to whether or not the first wireless signal has been received from the device in the region comprises:
    circuitry configured to determine whether or not the individual is compliant with a regimen targeting a portion of the individual, the individual being compliant if the data distillation indicative of the regimen compliance status does not include a compliance-negative indication, the region intersecting the portion of the individual.

27. The system of claim 13 in which the circuitry configured to signal the data distillation indicative of the regimen compliance status responsively to whether or not the first wireless signal has been received from the device in the region comprises:
    circuitry configured to determine whether or not the individual is compliant with a regimen targeting a portion of the individual, the individual being compliant if the data distillation indicative of the regimen compliance status indicates a health status improvement, the region intersecting the portion of the individual.

28. The system of claim 13 in which the circuitry configured to signal the data distillation indicative of the regimen compliance status responsively to whether or not the first wireless signal has been received from the device in the region comprises:
    circuitry configured to determine whether or not the individual is compliant with a regimen targeting a portion of the individual, the individual being compliant if the data distillation indicative of the regimen compliance status includes a normalcy indication, the region intersecting the portion of the individual.

29. The system of claim 13 in which the circuitry configured to decide whether or not to obtain one or more images of the region responsively to whether or not the first wireless signal has been received from the device in the region comprises:
    circuitry configured to condition an output upon a presence of or an absence of an indication of contraband, the contraband being detectable by the device and within the one or more images of the region.

30. A system comprising:
    circuitry configured to decide whether or not to obtain one or more images of a region responsively to whether or not a first wireless signal has been received from a device in the region; and
    circuitry configured to signal a data distillation indicative of a regimen compliance status responsively to whether or not the first wireless signal has been received from the device in the region in which the circuitry configured to signal the data distillation indicative of the regimen compliance status responsively to whether or not the first wireless signal has been received from the device in the region comprises:
        circuitry configured to condition a regimen noncompliance determination upon a determination that a presence of a second wireless signal from a capsule in a first frequency range below a reference frequency coincided with a presence of a third wireless signal in a second frequency range above the reference frequency from the capsule, the device being the capsule, the region being a vicinity of the capsule, the data distillation conditionally indicating a result of the regimen noncompliance determination;
        circuitry configured to condition a regimen compliance determination upon a first compliance positive indication and upon a second compliance positive indication, the data distillation indicating a result of the regimen compliance determination; and
        circuitry configured to cause a door to become locked or unlocked, the data distillation indicative of the regimen compliance status including an electromechanical control signal configured to control a lock of the door.

31. The system of claim 30 in which the circuitry configured to signal the data distillation indicative of the regimen compliance status responsively to whether or not the first wireless signal has been received from the device in the region comprises:
    circuitry configured to determine whether or not an individual is compliant with a regimen targeting a portion of the individual, the individual being compliant if the data distillation indicative of the regimen compliance status does not include a compliance-negative indication, the region intersecting the portion of the individual.

32. The system of claim 30 in which the circuitry configured to decide whether or not to obtain one or more images of the region responsively to whether or not the first wireless signal has been received from the device in the region comprises:
 circuitry configured to condition an output upon a presence of or an absence of an indication of contraband, the contraband being detectable by the device and within the one or more images of the region.

33. The system of claim 30 in which the circuitry configured to signal the data distillation indicative of the regimen compliance status responsively to whether or not the first wireless signal has been received from the device in the region comprises:
 circuitry configured to condition whether or not a message is sent upon whether or not a temperature exceeds a threshold, the temperature being at the device, the device including a temperature sensor, whether or not the message is sent being a component of the data distillation indicative of the regimen compliance status.

34. The system of claim 30 in which the circuitry configured to signal the data distillation indicative of the regimen compliance status responsively to whether or not the first wireless signal has been received from the device in the region comprises:
 circuitry configured to decide whether or not a status of an individual has changed, the device configured to be supported by the individual, the status of the individual including the regimen compliance status, the data distillation being signaled responsively to whether or not the first wireless signal has been received from the device in the region.

35. The system of claim 30 in which the circuitry configured to signal the data distillation indicative of the regimen compliance status responsively to whether or not the first wireless signal has been received from the device in the region comprises:
 circuitry configured to distill historical data indicative of or contraindicative of a health status transition relating to an infection in an individual, the data distillation indicative of the regimen compliance status resulting from distilling the historical data indicative of or contraindicative of a health status transition relating to an infection in the individual responsively to whether or not the first wireless signal has been received from the device in the region, the health status transition relating to the infection in the individual being a health status improvement.

36. The system of claim 30 in which the circuitry configured to signal the data distillation indicative of the regimen compliance status responsively to whether or not the first wireless signal has been received from the device in the region comprises:
 circuitry configured to distill historical data indicative of or contraindicative of a health status transition relating to an infection in an individual, the data distillation indicative of the regimen compliance status resulting from distilling the historical data indicative of or contraindicative of a health status transition relating to an infection in the individual responsively to whether or not the first wireless signal has been received from the device in the region, the health status transition relating to the infection in the individual being a health status deterioration.

37. The system of claim 30 in which the circuitry configured to signal the data distillation indicative of the regimen compliance status responsively to whether or not the first wireless signal has been received from the device in the region comprises:
 circuitry configured to obtain an indication of whether or not an individual remains enrolled in a program requiring a therapeutic regimen, the data distillation indicative of the regimen compliance status resulting from an application of a distillation protocol specified by the program requiring the therapeutic regimen.

38. The system of claim 30 in which the circuitry configured to signal the data distillation indicative of the regimen compliance status responsively to whether or not the first wireless signal has been received from the device in the region comprises:
 circuitry configured to signal a regimen compliance data distillation by identifying a data distillation protocol, the data distillation indicative of the regimen compliance status being the regimen compliance data distillation, the data distillation protocol being selected in response to a type of data received in the first wireless signal.

39. The system of claim 30 in which the circuitry configured to signal the data distillation indicative of the regimen compliance status responsively to whether or not the first wireless signal has been received from the device in the region comprises:
 circuitry configured to obtain a regimen compliance data distillation by causing an application of one or more auditory data distillation criteria, at least one of the one or more auditory distillation criteria being configured to determine whether or not auditory data from the region includes a compliance-positive indication, the compliance-positive indication being at least one of a swallowing sound or a vocalized assertion.

40. The system of claim 30 in which the circuitry configured to signal the data distillation indicative of the regimen compliance status responsively to whether or not the first wireless signal has been received from the device in the region comprises:
 circuitry configured to obtain a regimen compliance data distillation by causing an application of one or more auditory data distillation criteria to auditory data from the region, the data distillation indicative of the regimen compliance status being the regimen compliance data distillation.

41. The system of claim 30 in which the circuitry configured to signal the data distillation indicative of the regimen compliance status responsively to whether or not the first wireless signal has been received from the device in the region comprises:
 circuitry configured to determine whether or not an individual is compliant with a regimen targeting a portion of the individual, the individual being compliant if the data distillation indicative of the regimen compliance status indicates a health status improvement, the region intersecting the portion of the individual.

42. The system of claim 30 in which the circuitry configured to signal the data distillation indicative of the regimen compliance status responsively to whether or not the first wireless signal has been received from the device in the region comprises:
 circuitry configured to determine whether or not an individual is compliant with a regimen targeting a portion of the individual, the individual being compliant if the data distillation indicative of the regimen compliance status includes a normalcy indication, the region intersecting the portion of the individual.

43. The system of claim 30 in which the circuitry configured to signal the data distillation indicative of the regimen compliance status responsively to whether or not the first wireless signal has been received from the device in the region comprises:
    circuitry configured to determine whether or not a therapy is having a specific effect, the data distillation indicative of the regimen compliance status being a determination of whether or not the therapy is having the specific effect, the specific effect being at least one of a health status improvement or a health status deterioration.

\* \* \* \* \*